(12) United States Patent
Snutch et al.

(10) Patent No.: US 7,297,504 B1
(45) Date of Patent: Nov. 20, 2007

(54) METHODS FOR IDENTIFYING AGONISTS AND ANTAGONISTS OF HUMAN T-TYPE CALCIUM CHANNELS

(75) Inventors: Terry P. Snutch, Vancouver (CA); David L. Baillie, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 514 days.

(21) Appl. No.: 09/346,794

(22) Filed: Jul. 2, 1999

Related U.S. Application Data

(63) Continuation-in-part of application No. 09/030,482, filed on Feb. 25, 1998, now abandoned.

(60) Provisional application No. 60/039,204, filed on Feb. 28, 1997.

(51) Int. Cl.
*G01N 33/53* (2006.01)
*C12Q 1/68* (2006.01)

(52) U.S. Cl. .................. 435/7.21; 435/69.1; 435/252.3; 435/320.1; 435/375; 435/325; 530/350; 536/23.1

(58) Field of Classification Search .................. 435/7.2, 435/69.1, 7.1, 6, 7, 7.21, 172.3, 235.1, 320.1, 435/325; 536/23.1, 24.3; 530/300, 350
See application file for complete search history.

(56) References Cited

U.S. PATENT DOCUMENTS

| | | | |
|---|---|---|---|
| 5,386,025 A | 1/1995 | Jay et al. .................... | 536/23.5 |
| 5,401,629 A | 3/1995 | Harpold et al. | |
| 5,429,921 A * | 7/1995 | Harpold et al. ................. | 435/4 |
| 5,688,938 A * | 11/1997 | Brown et al. .............. | 536/23.5 |
| 5,804,436 A * | 9/1998 | Okun et al. .............. | 435/286.1 |
| 5,837,479 A | 11/1998 | Young et al. | |
| 6,309,858 B1 | 10/2001 | Dietrich et al. ............ | 435/69.1 |
| 6,358,706 B1 | 3/2002 | Dubin et al. ............... | 435/69.1 |
| 6,528,630 B1 | 3/2003 | Williams et al. ........... | 536/23.1 |
| 2003/0125269 A1 | 7/2003 | Li ............................... | 514/44 |

FOREIGN PATENT DOCUMENTS

| | | |
|---|---|---|
| WO | WO 95/04144 | 2/1995 |
| WO | WO 96/39512 | 12/1996 |
| WO | WO 98/38301 | 9/1998 |
| WO | WO 99/28342 | 6/1999 |
| WO | WO 99/29847 | 6/1999 |
| WO | WO 00/7044 | 11/2000 |
| WO | WO 01/19845 | 3/2001 |

OTHER PUBLICATIONS

Williams et al, Structure and Functional Expression of Alpha1, Alpha2, and Beta Subunits of a Novel Human Neuronal Calcium Channel Subtype, Jan. 1992, Neuron, vol. 8, pp. 71-64.*

Sylvia et al, Low-voltage-activated T-type Ca2+ Channels, Feb. 1997, TIPS, vol. 18, pp. 37-42.*

Bork et al. Predicting Functions From Protein Sequences-Where Are The Bottlenecks, 1998, Nature Genetics, vol. 18, pp. 313-318.*

Karp et al., Editorial, Bioinformatics, 1998, vol. 14, No. 9, pp. 753-754.*

Bork et al., Sequences and Topolgy Deriving biological Knowlwdge from genomic sequences, 1998, current Opinion in structural Biology, vol. 8, pp. 331-332.*

Perez-Reyes, E., et al, "Molecular characterization of a neuronal low-voltage-activated T-type calcium channel", Nature 391:896-900, Feb. 26, 1998.

Cribbs, L.L., et al, "Cloning and Characterization of alpha-1H From Human Heart, a Member of the T-Type Ca2+ Channel Gene Family", Circ. Res. 83:103-109, Jul. 13, 1998.

Williams, M.E., et al, "Structure and Functional Characterization of a Novel Human Low-Voltage Activated Calcium Channel", J. Neurochem. 72(2):791-799, 1999.

Lee, J-H., et al, "Cloning and Expression of a Novel Member of the Low Voltage-Activated T-Type Calcium Channel Family", J. Neurosci, 19(6):1912-1921, Mar. 15, 1999.

Trofatter, J.A., et al, "An Expression-independent Catalog of Genes from Human Chromosome 22", Genome Res. 5(3):214-224, Oct. 1995, United States, XP002069420.

Trofatter, J.A., et al., "An Expression-independent Catalog of Genes from Human Chromosome 22", Genome Research 5(3):214-224, Oct. 1995.

Stratagene catalog (1991) p. 66.

Brizzard and Chubet, Current Protocols in Neuroscience (1997) 5.8.1-5.8.10.

Pubmed search results for "t-type calcium channel Parkinson's" and "t-type calcium channel schizophrenia", accessed Sep. 27, 2005.

Partial European Search Report for EP 06 11 5615, mailed on Feb. 27, 2007, 4 pages.

Mittman et al., Neuroscience Letters (1999) 274(3):143-146.

* cited by examiner

*Primary Examiner*—Christine J. Saoud
*Assistant Examiner*—Nirmal S. Basi
(74) *Attorney, Agent, or Firm*—Morrison & Foerster LLP

(57) ABSTRACT

Sequences and partial sequences for three types of mammalian (human and rat) sequences identified) T-type calcium channel subunits which we have labeled as the $\alpha_{1G}$, $\alpha_{1H}$ and $\alpha_{1I}$ subunits are provided. Knowledge of the sequence of these calcium channel permits the localization and recovery of the complete sequence from human cells, and the development of cell lines which express the novel calcium channels of the invention. These cells may be used for identifying compounds capable of acting as agonists or antagonists to the calcium channels.

4 Claims, 4 Drawing Sheets

$\alpha_{1I}$
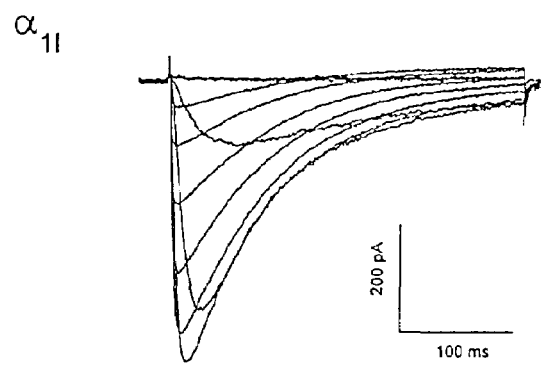 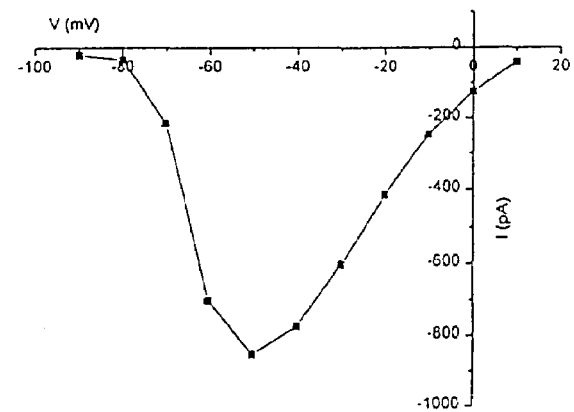
Fig. 2A                              Fig. 2 B

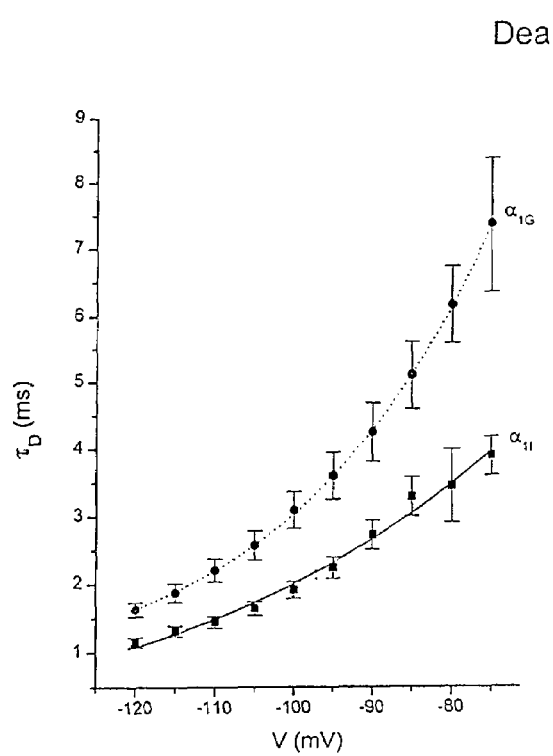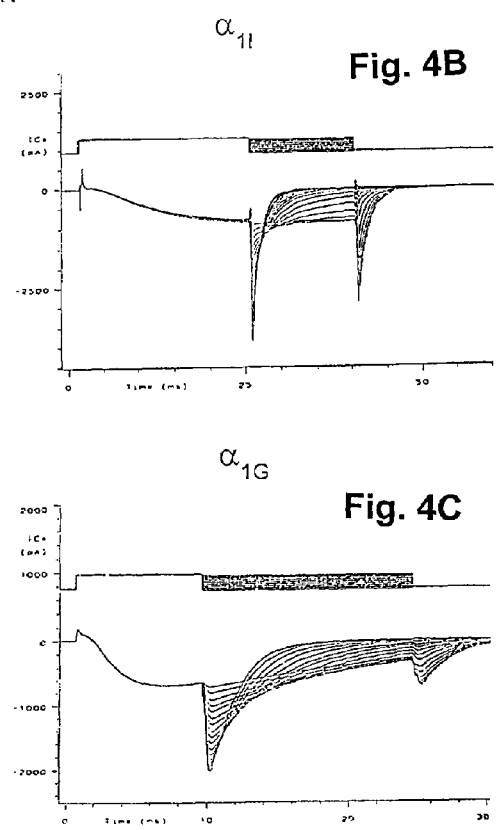
Fig. 4A
Fig. 4B
Fig. 4C

METHODS FOR IDENTIFYING AGONISTS AND ANTAGONISTS OF HUMAN T-TYPE CALCIUM CHANNELS

This application is a continuation-in-part of U.S. patent application Ser. No. 09/030,482, filed Feb. 25, 1998 now abandoned, which is a 111(a) application claiming priority from U.S. Provisional Application No. 60/039,204, filed Feb. 28, 1997, both of which are incorporated herein by reference.

TECHNICAL FIELD

The present invention relates to novel mammalian (including human) calcium channel compositions, and to the expression of these compositions in cell lines for use in evaluating calcium channel function and the behavior of compositions which modulate calcium channel function.

BACKGROUND OF THE INVENTION

The rapid entry of calcium into cells is mediated by a class of proteins called voltage-gated calcium channels. Calcium channels are a heterogeneous class of molecules that respond to depolarization by opening a calcium-selective pore through the plasma membrane. The entry of calcium into cells mediates a wide variety of cellular and physiological responses including excitation-contraction coupling, hormone secretion and gene expression. In neurons, calcium entry directly affects membrane potential and contributes to electrical properties such as excitability, repetitive firing patterns and pacemaker activity. Miller, R. J. (1987) "Multiple calcium channels and neuronal function." *Science* 235:46-52. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter. Calcium entry also plays a role in neurite outgrowth and growth cone migration in developing neurons and has been implicated in long-term changes in neuronal activity.

In addition to the variety of normal physiological functions mediated by calcium channels, they are also implicated in a number of human disorders. Recently, mutations identified in human and mouse calcium channel genes have been found to account for several disorders including, familial hemiplegic migraine, episodic ataxia type 2, cerebellar ataxia, absence epilepsy and seizures. Fletcher, et al. (1996) "Absence epilepsy in tottering mutant mice is associated with calcium channel defects." *Cell* 87:607-617; Burgess, et al. (1997) "Mutation of the Ca2+ channel β subunit gene Cchb4 is associated with ataxia and seizures in the lethargic (lh) mouse." *Cell* 88:385-392; Ophoff, et al. (1996) "Familial hemiplegic migraine and episodic ataxia type-2 are caused by mutations in the Ca2+ channel gene CACNL1A4." *Cell* 87:543-552; Zhuchenko, O. et al. (1997) "Autosomal dominant cerebellar ataxia (SCA6) associated with the small polyglutamine expansions in the α1A-voltage-dependent calcium channel." *Nature Genetics* 15:62-69.

The clinical treatment of some disorders have been aided by the development of therapeutic calcium channel antagonists. Janis, et al. (1991) in *Calcium Channels: Their Properties, Functions, Regulation and Clinical Relevance*. CRC Press, London.

Native calcium channels have been classified by their electrophysiological and pharmacological properties as T, L, N, P and Q types (for reviews see McCleskey, et al. (1991) "Functional properties of voltage-dependent calcium channels." *Curr. Topics Membr.* 39: 295-326, and Dunlap, et al. (1995) "Exocytotic $Ca^{2+}$ channels in mammalian central neurons." *Trends Neurosci.* 18:89-98.). T-type (or low voltage-activated) channels describe a broad class of molecules that activate at negative potentials and are highly sensitive to changes in resting potential. The L, N, P and Q-type channels activate at more positive potentials and display diverse kinetics and voltage-dependent properties. There is some overlap in biophysical properties of the high voltage-activated channels, consequently pharmacological profiles are useful to further distinguish them. L-type channels are sensitive to dihydropyridine (DHP) agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated Ca channel (Q-type) has been described, although whether the Q- and P-type channels are distinct molecular entities is controversial (Sather et al. (1993) "Distinctive biophysical and pharmacological properties of class A (B1) calcium channel α1 subunits." *Neuron* 11:291-303; Stea, et al. (1994) "Localization and functional properties of a rat brain α1A calcium channel reflect similarities to neuronal Q- and P-type channels." *Proc Natl Acad Sci (USA)* 91: 10576-10580.). Several types of calcium conductances do not fall neatly into any of the above categories and there is variability of properties even within a category suggesting that additional calcium channels subtypes remain to be classified.

Biochemical analyses show that neuronal high-threshold calcium channels are heterooligomeric complexes consisting of three distinct subunits ($α_1$, $α_2δ$ and $β$)(reviewed by De Waard, et al. (1997) in *Ion Channels*, Volume 4, edited by Narahashi, T. Plenum Press, New York). The $α_1$ subunit is the major pore-forming subunit and contains the voltage sensor and binding sites for calcium channel antagonists. The mainly extracellular $α_2$ is disulphide-linked to the transmembrane $δ$ subunit and both are derived from the same gene and are proteolytically cleaved in vivo. The $β$ subunit is a non-glycosylated, hydrophilic protein with a high affinity of brining to a cytoplasmic region of the $α_1$ subunit. A fourth subunit, $γ$, is unique to L-type Ca channels expressed in skeletal muscle T-tubules. The isolation and characterization of γ-subunit-encoding cDNA is described in U.S. Pat. No. 5,386,025 which is incorporated herein by reference.

Molecular cloning has revealed the cDNA and corresponding amino acid sequences of six different types of $α_1$ subunits ($α_{1A}$, $α_{1B}$, $α_{1C}$, $α_{1D}$, $α_{1E}$ and $α_{1S}$) and four types of $β$ subunits ($β_1$, $β_2$, $β_3$ and $β_4$)(reviewed in Stea, A., Soong, T. W. and Snutch, T. P. (1994) "Voltage-gated calcium channels." in *Handbook of Receptors and Channels*. Edited by R. A. North, CRC Press.) PCT Patent Publication WO 95/04144, which is incorporated herein by reference, discloses the sequence and expression of $\alpha_{1E}$ calcium channel subunits.

The different classes of α1 and β subunits have been identified in different animals including, rat, rabbit and human and share a significant degree of amino acid conservation across species (for examples see: Castellano, et al. (1993) "Cloning and expression of a third calcium channel β subunit." *J. Biol. Chem.* 268: 3450-3455; Castellano, et al. (1993) "Cloning and expression of a neuronal calcium channel β subunit." *J. Biol. Chem.* 268: 12359-12366; Dubel, et al. (1992). "Molecular cloning of the $\alpha_1$ subunit of an ω-conotoxin-sensitive calcium channel." *Proc. Natl. Acad. Sci. (USA)* 89: 5058-5062; Fujita, et al. (1993) "Primary structure and functional expression of the ω-conotoxin-sensitive N-type calcium channel from rabbit brain." *Neuron* 10: 585-598; Mikami, et al. (1989). "Primary structure and functional expression of the cardiac dihydropyridine-sensitive calcium channel." *Nature* 340: 230-233; Mori, et al. (1991) "Primary structure and functional expression from complementary DNA of a brain calcium channel." *Nature* 350: 398-402; Perez-Reyes, et al. (1992). "Cloning and expression of a cardiac/brain β subunit of the L-type calcium channel." *J. Biol. Chem.* 267: 1792-1797; Pragnell, et al. (1991). "Cloning and tissue-specific expression of the brain calcium channel β-subunit." *FEBS Lett.* 291: 253-258; Snutch, et al. (1991) "Distinct calcium channels are generated by alternative splicing and are differentially expressed in the mammalian CNS." *Neuron* 7: 45-57; Soong, et al. (1993) "Structure and functional expression of a member of the low voltage-activated calcium channel family." *Science* 260: 1133-1136; Tomlinson, et al. (1993) "Functional properties of a neuronal class C L-type channel." *Neuropharmacology* 32: 1117-1126; Williams, et al. (1992) "Structure and functional expression of α1, α2, and β subunits of a novel human neuronal calcium channel subtype." *Neuron* 8: 71-84; Williams et al. (1992) "Structure and functional expression of an ω-conotoxin-sensitive human N-type calcium channel." *Science* 257: 389-395.

In some expression systems the $\alpha_1$ subunits alone can form functional calcium channels although their electrophysiological and pharmacological properties can be differentially modulated by coexpression with any of the four β subunits. Until recently, the reported modulatory affects of β subunit coexpression were to mainly alter kinetic and voltage-dependent properties. More recently it has been shown that β subunits also play crucial roles in modulating channel activity by protein kinase A, protein kinase C and direct G-protein interaction. (Bourinet, et al. (1994) "Voltage-dependent facilitation of a neuronal α1C L-type calcium channel." *EMBO J.* 13: 5032-5039; Stea, et al. (1995) "Determinants of PKC-dependent modulation of a family of nuronal calcium channels." *Neuron* 15:929-940; Bourinet, et al. (1996) "Determinants of the G-protein-dependent opioid mdoulation of neuronal calcium channels." *Proc. Natl. Acad. Sci. (USA)* 93: 1486-1491.)

The electrophysiological and pharmacological properties of the calcium channels cloned to date can be summarized as shown in Table 1. While the cloned $\alpha_1$ subunits identified to date correspond to several of the calcium channels found in cells, they do not account for all types of calcium conductances described in native cells. For example, they do not account for the various properties described for the heterogenous family described as T-type calcium channels. Furthermore, they do not account for novel calcium channels described in cerebellar granule cells or other types of cells. (Forti, et al (1993) "Functional diversity of L-type calcium channels in rat cerebellar neurons." *Neuron* 10: 437-450; Tottene, et al. (1996). "Functional diversity of P-type and R-type calcium channels in rat cerebellar neurons." *J. Neurosci.* 16: 6353-6363).

Because of the importance of calcium channels in cellular metabolism and human disease, it would be desirable to identify the remaining classes of $\alpha_1$ subunits, and to develop expression systems for these subunits which would permit the study and characterization of these calcium channels, including the study of pharmacological modulators of calcium channel function. Thus, it is an object of the present invention to provide heretofor undisclosed calcium channels having novel $\alpha_1$ subunits, including cell lines expressing these

TABLE 1

|  | ω-conotoxin GVIA | 1,4-dihydropyridines | cadmium | ω-agatoxin IVA | ω-conotoxin MVIIC | native $Ca^{2+}$ channel type |
|---|---|---|---|---|---|---|
| $\alpha_{1A}$ | — | — | ✓ | ✓ | ✓ | P/Q-type |
| $\alpha_{1B}$ | ✓ | — | ✓ | — | ✓ | N-type |
| $\alpha_{1C}$ | — | ✓ | ✓ | — | — | L-type |
| $\alpha_{1D}$ | — | ✓ | ✓ | — | — | L-type |
| $\alpha_{1E}$ | — | — | ✓ | — | — | novel |
| $\alpha_{1S}$ | — | ✓ | ✓ | — | — | L-type | new calcium channels. It is a further object of the present invention to provide a method for testing these novel calcium channels using such cell lines.

SUMMARY OF THE INVENTION

The present invention provides sequences for a novel mammalian calcium channel subunits of T-type calcium channels, which we have labeled as $\alpha_{1G}$, $\alpha_{1H}$ and $\alpha_{1I}$ subunits. Knowledge of the sequences of these calcium channel subunits may be used in the development of probes for mapping the distribution and expression of the subunits in target tissues. In addition, these subunits, either alone or assembled with other proteins, can produce functional calcium channels, which can be evaluated in model cell lines to determine the properties of the channels containing the subunits of the invention. These cell lines can be used to evaluate the affects of pharmaceuticals and/or toxic substances on calcium channels incorporating $\alpha_{1G}$, $\alpha_{1H}$ and $\alpha_{1I}$ subunits.

BRIEF DESCRIPTION OF THE DRAWINGS

FIGS. 2A and B show a comparison of the waveforms and current voltage relationship for $\alpha_{1I}$ calcium channels.

FIGS. 4A-C show a comparison of the inactivation kinetics of the $\alpha_{1G}$ and $\alpha_{1I}$ calcium channels.

DETAILED DESCRIPTION OF THE INVENTION

Figure 1A:
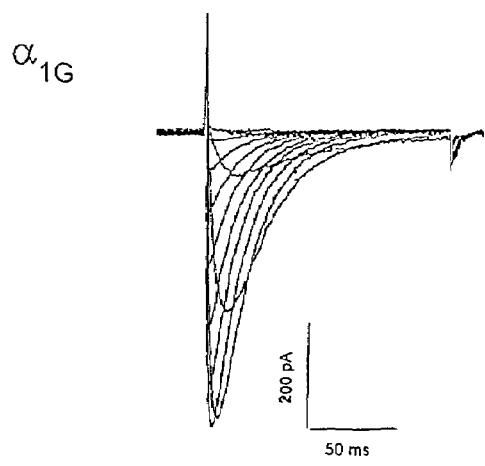
FIGS. 1A and B show a comparison of the waveforms and current voltage relationship for $\alpha_{1G}$.

The present invention includes the following aspects for which protection is sought:

(a) novel mammalian (including human) calcium channel subunits and DNA sequences encoding such subunits. Specifically, the invention encompasses an at least partially purified DNA molecule comprising a sequence of nucleotides that encodes an α subunit of a T-type calcium channel, and such α subunit per se. It will be appreciated that polymorphic variations may be made or may exist in the DNA of some individuals leading to minor deviations in the DNA or amino acid sequences from those shown which do not lead to any substantial alteration in the function of the calcium channel. Such variations, including variations which lead to substitutions of amino acids having similar properties are considered to be within the scope of the present invention. Thus, in one embodiment, the present application claims DNA molecules which encode $\alpha_1$ subunits of mammalian T-type calcium channels, and which hybridize under conditions of medium (or higher) hybridization stringency with one or another of the specific sequences disclosed in this application. This level of hybridization stringency is generally sufficient given the length of the sequences involved to permit recovery of the subunits within the scope of the invention from mammalian DNA libraries.

(b) polynucleotide sequences useful as probes in screening human cDNA libraries for genes encoding these novel calcium channel subunits. These probes can also be used in histological assay to determine the tissue distribution of the novel calcium channel subunits.

(c) at least partially purified $\alpha_1$ subunits and related peptides for mammalian T-type calcium channels. These proteins and peptides can be used to generate polyclonal or monoclonal antibodies to determine the cellular and subcellular distribution of T-type calcium channel subunits.

(d) eukaryotic cell lines expressing the novel calcium channel subunits. These cell lines can be used to evaluate compounds as pharmacological modifiers of the function of the novel calcium channel subunits.

(e) a method for evaluating compounds as pharmacological modifiers of the function of the novel calcium channel subunits using the cell lines expressing those subunits alone or in combination with other calcium channel subunits.

Further, since defects in the novel calcium channel subunits may be associated with a human genetic disease including, but not limited to; epilepsy, migraine, ataxia, schizophrenia, hypertension, arrhythmia, angina, depression, small lung carcinoma, Lambert-Eaton syndrome and Parkinson's disease; characterization of such associations and ultimately diagnosis of associated diseases can be carried out with probes which bind to the wild-type or defective forms of the novel calcium channels.

As used in this specification and claims of this application, the term "T-type calcium channel" refers to a voltage-gated calcium channel having a low activation voltage, generally less than −50 mV, and most commonly less than −60 mV. T-type calcium channels also exhibit comparatively negative steady-state inactivation properties and slow deactivation kinetics. The terms "$\alpha_1$ subunit" or "$\alpha_1$ calcium channel" refer to a protein subunit of a calcium channel which is responsible for pore formation and contains the voltage sensor and binding sites for calcium channel agonists and antagonists. Such subunits may be independently functional as calcium channels or may require the presence of other subunit types for complete functionality.

As used in the specification and claims of this application, the phrase "at least partially purified" refers to DNA or protein preparations in the which the specific molecule has been separated from adjacent cellular components and molecules with which it occurs in the natural state, either by virtue of performing a physical separation process or by virtue of making the DNA or protein molecule in a non-natural environment in the first place. The term encompasses cDNA molecules and expression vectors.

In accordance with the present invention, we have identified mammalian DNA sequences which code for novel T-type calcium channel $\alpha_1$ subunits. These subunits are believed to represent new types of $\alpha_1$ subunits of mammalian voltage-dependent calcium channels which have been designated as types $\alpha_{1G}$, $\alpha_{1H}$ and $\alpha_{1I}$.

The novel $\alpha_1$ subunits of the invention were identified by screening the *C. elegans* genomic DNA sequence data base for sequences homologous to previously identified mammalian calcium channel $\alpha_1$ subunits. Specifically, the following twelve mammalian $\alpha_1$ subunit sequences were used to screen the *C. elegans* genomic data bank:

| | |
|---|---|
| rat brain $\alpha_{1A}$:<br>GTCAAAACTC AGGCCTTCTA CTGG | SEQ ID. No. 1 |
| rat brain $\alpha_{1A}$:<br>AACGTGTTCT TGGCTATCGC GGTG | SEQ ID. No. 2 |
| rat brain $\alpha_{1B}$:<br>GTGAAAGCAC AGAGCTTCTA CTGG | SEQ ID. No. 3 |
| rat brain $\alpha_{1B}$:<br>AACGTTTTCT TGGCCATTGC TGTG | SEQ ID. No. 4 |
| rat brain $\alpha_{1C}$:<br>GTTAAATCCA ACGTCTTCTA CTGG | SEQ ID. No. 5 |
| rat brain $\alpha_{1C}$:<br>AATGTGTTCT TGGCCATTGC GGTG | SEQ ID. No. 6 |
| rat brain $\alpha_{1D}$:<br>GTGAAGTCTG TCACGTTTTA CTGG | SEQ ID. No. 7 |
| rat brain $\alpha_{1D}$:<br>AAGCTCTTCT TGGCCATTGC TGTA | SEQ ID. No. 8 |

-continued

```
rat brain α1E:                         SEQ ID. No. 9
GTCAAGTCGC AAGTGTTCTA CTGG rat brain α1E:                         SEQ ID. No. 10
AATGTATTCT TGGCTATCGC TGTG rat brain consensus #1:                SEQ ID. No. 11
ATCTAYGCYR TSATYGGSAT G rat brain consensus #2:                SEQ ID. No. 12
ATGGACAAYT TYGASTAYTC
```

This search identified four distinct *C. elegans* cosmids that contain open reading frames (coding regions) that exhibit homology to mammalian calcium channel $\alpha_1$ subunits:

cosmid and reading frame T02C5.5
cosmid and reading frame C48A7.1
cosmid and reading frame C54D2.5
cosmid and reading frame C27F2.3

Examination of the four *C. elegans* cosmid sequences by phylogeny analysis shows that two of these, T02C5.5 and C48A7.1, correspond closely with previously identified mammalian $\alpha_1$ subunits. T02C5.5 appears to be an ancestral member related to the mammalian $\alpha_{1A}$, $\alpha_{1B}$ and $\alpha_{1E}$ subunits. C48A7.1 appears to be an ancestral member related to the mammalian L-type channels encoded by $\alpha_{1C}$, $\alpha_{1D}$ and $\alpha_{1S}$. In contrast, the *C. elegans* cosmids C54D2.5 and C27F2.3 identify novel types of calcium channel $\alpha_1$ subunits distinct from the other mammalian subtypes.

Mammalian counterparts of the *C. elegans* calcium channel $\alpha_1$ subunit encoded by C54D2.5 were identified by screening of the GenBank expressed sequence tag (EST) data bank. This analysis identified a total of 13 mammalian sequences that exhibit some degree of DNA sequence and amino acid identity to C54D2.5, of which 8 are human sequences. (Table 2) Some of these sequences appear unlikely to encode novel calcium channel subunits because they either exhibit a significant degree of homology to previously identified mammalian $\alpha_1$ subunits (for example, clones H06096 and H14053) or exhibit homology in a region not considered to be diagnostic of calcium channel $\alpha_1$ subunits specifically as opposed to other types of ion channel molecules in general (for example, clone D20469). One of the five remaining sequences was evaluated and appears to encode a sodium channel. Four sequences (H55225, H55617, H55223, and H55544), however, encode what are believed to be previously unidentified calcium channel $\alpha_1$ subunits. For these subunits, the amino acid sequences closely match that of known calcium channel subunits in conserved regions but are sufficiently different to indicate that they do not encode previously identified mammalian calcium channel $\alpha_1$ subunits, $\alpha_{1A}$, $\alpha_{1B}$, $\alpha_{1C}$, $\alpha_{1D}$, $\alpha_{1E}$, or $\alpha_{1S}$. The expected amino acid sequence closely matches but is not identical to amino acid sequences in these known calcium channel subunits.

TABLE 2

Query = C54D2.5 CE02562 CALCIUM CHANNEL ALPHA-1 SUBUNIT LG:6
Database: Non-redundant Database of GenBank EST Division 824,500 sequences; 302,742,428 total letter

| Sequences producing High-scoring Segment Pairs: | | Frame | Score | P(N) |
|---|---|---|---|---|
| gb \| AA183990 \| AA183990 | ms53e02.r1 Life Tech mouse embry . . . | +1 | 108 | 1.8e-24 |
| gb \| H55225 \| H55225 | CHR220164 *Homo sapiens* genomic c . . . | +1 | 136 | 2.5e-10 |
| dbj \| D68412 \| CELK131B1F | *C. elegans* cDNA clone yk131b1:5 . . . | +3 | 117 | 1.7e-06 |
| gb \| R75128 \| R75128 | MDB1075 Mouse brain, Stratagene . . . | +3 | 113 | 7.2e-06 |
| gb \| H55617 \| H55617 | CHR220556 *Homo sapiens* genomic c . . . | +2 | 102 | 2.8e-05 |
| emb \| F07776 \| HSC2HD061 | *H. sapiens* partial cDNA sequence . . . | +3 | 100 | 0.00057 |
| gb \| W76774 \| W76774 | me84e08.r1 Soares mouse embryo N . . . | +2 | 98 | 0.0012 |
| gb \| H06096 \| H06096 | yl77e01.r1 *Homo sapiens* cDNA clo . . . | +3 | 98 | 0.0015 |
| gb \| H14053 \| H14053 | ym65d10.r1 *Homo sapiens* cDNA clo . . . | +2 | 91 | 0.0036 |
| gb \| H55223 \| H55223 | CHR220162 Homo sapiens genomic c . . . | +2 | 87 | 0.0039 |
| dbj \| D35703 \| CELK024D9F | *C. elegans* cDNA clone yk24d9 : 5' . . . | +3 | 74 | 0.046 |
| dbj \| D20469 \| HUMGS01443 | Human HL60 3' directed MboI cDNA, . . . | −2 | 66 | 0.91 |
| gb \| H55544 \| H55544 | CHR220483 *Homo sapiens* genomic c . . . | +1 | 65 | 0.98 |

The four sequences (H55225, H55617, H55223, and H55544) are found on human chromosome 22, and are now believed to all be part of the same gene encoding the novel human calcium channel subunit $\alpha_{1T}$.

The sequences of the four selected sequences and the references from which they are taken are given as follows:

| H55225 | SOURCE | human clone = C22_207 primer = T3 library = Chromosome 22 exon |
|---|---|---|

Trofatter, et al., *Genome Res.* 5(3): 214-224 (1995)
    SEQ ID No. 13

```
  1 GTGATCACTC TGGAAGGCTG GGTGGAGATC ATGTACTACG TGATGGATGC TCACTCCTTC
 61 TACAACTTCA TCTACTTCAT CCTGCTTATC ATACCCCTCT TGCCTTGCAC CCCATATGGT
121 CTTCCCAGAG TGAGCTCATC CACCTCGTCA TGCCTGACTC GACGTTCA
```

| H55617 | SOURCE | human clone = C22_757 primer = T3 library = Chromosome 22 exon |
|---|---|---|

Trofatter, et al., *Genome Res.* 5 (3): 214-224 (1995)

SEQ ID No. 14

```
  1 GATGGTCGAG TACTCCCTGG ACCTTCAGAA CATCAACCTG TCAGCCATCC GCACCGTGCG
 61 CGTCCTGAGG CCCCTCAAAG CCATCAACCG CGTGCCCA
```

| H55223 | SOURCE | human clone = C22_204 primer = T3 library = Chromosome 22 exon |
|---|---|---|

Trofatter, et al., *Genome Res.* 5 (3): 214-224 (1995)

SEQ ID No. 15

```
  1 CATGCTGGTG ATCCTGCTGA ACTGCGTGAC ACTTGGCATG TACCAGCCGT GCGACGACAT
 61 GGACTGCCTG TCCGACCGCT GCAAGATCCT GCAG
```

| H55544 | SOURCE | human clone = C22_651 primer = T3 library = Chromosome 22 exon |
|---|---|---|

Trofatter, et al., *Genome Res.* 5 (3): 214-224 (1995)

SEQ ID No. 16

```
  1 GTATCTCTGG TTACTTTAGT AGCCAACACT CTTGGCTACT CAGACCTTGG TCCCATTAAA
 61 TCCCTGCGAA CCTTGAGAGC ACTAAGACCT CTAAGAGCTT TGTCTAGATT TGAAGGAATG
121 AGG
```

A search of the Sanger Genome Sequencing Center (Cambridge, U.K.) and the Washington University Genome Sequencing Center (St. Louis, Mo.) sequences in progress revealed a Bacterial Artificial Chromosome (BAC) sequence (bK206c7) that contained matches to the *C. elegans* cosmid open reading frame, C54D2.5, and to the four human chromosome 22 ESTs, H55225, H55617, H55223, H55544. The *C. elegans* C54D2.5 cosmid sequence and the human EST sequences were then used to compare the translation of the bK206c7 BAC genomic sequence in all 6 reading frames. The analysis was performed using the graphical program Dotter (Eric Sohnhammer, NCBI). The analysis revealed a series of potential coding regions on one strand of the bK206c7 BAC sequence. These were subsequently translated in all 3 reading frames and the potential splice junction identified. The translated sequence of this longer DNA fragment which is part of the human $\alpha_{1I}$ subunit gene is given by SEQ ID Nos. 17 and 18.

Using the sequence information from the four EST's, a full length gene can be recovered using any of several techniques. Polynucleotide probes having a sequence which corresponds to or hybridizes with the EST sequences or a distinctive portion thereof (for example oligonucleotide probes having a length of 18 to 100 nucleotides) can be used to probe a human cDNA library for identification of the full length DNA encoding the $\alpha_{1I}$ subunits. The process of identifying cDNAs of interest using defined probes is well known in the art and is, for example, described in International Patent Publication No. WO95/04144, which is incorporated herein by reference. This process generally involves screening bacterial hosts (e.g. *E. coli*) harboring the library plasmids or infected with recombinant lambda phage with labeled probes, e.g. radiolabeled with $^{32}P$, and selection of colonies or phage which bind the labeled probe. Each selected colony or phage is grown up, and the plasmids are recovered. Human cDNAs are recovered from the plasmids by restriction digestion, or can be amplified, for example by PCR. The recovered cDNA can be sequenced, and the position of the calcium channel subunit-encoding region further refined, although neither process is not necessary to the further use of the cDNA to produce cell lines expressing the novel calcium channel subunits.

Longer portions of DNA-encoding the novel calcium channel subunits of the invention can also be recovered by PCR cloning techniques using primers corresponding to or based upon the EST sequences. Using this technique to identify relevant sequences within a human brain total RNA preparation confirmed that the novel $\alpha_{1I}$ calcium channel subunit is present in human brain. Subcloning of the 567 nt PCR product (Seq. ID No. 19, amino acids Seq. ID No. 20) and subsequent sequencing thereof showed that this product corresponds to the derived sequence form the bK206c7 BAC genomic sequence, the nucleotide sequence of which is given as SEQ ID No. 17 (amino acid sequence Seq. ID No. 18). The same experiment was performed using a rat brain RNA preparation and resulted in recovery of a substantially identical PCR product. (SEQ ID No. 21). The protein encoded by the rat PCR product (SEQ ID No. 22) is 96% identical to the human PCR product (Seq. ID No. 20).

These sequences, which encode a partial subunit can be used as a basis for constructing full length human or rat $\alpha_{1I}$ clones. Briefly, the subcloned $\alpha_{1I}$ PCR product is radiolabeled by random hexamer priming according to standard methods (See, Sambrook, J., Fritsch, E. F. and Maniatis, T. (1989) *Molecular Cloning, A Laboratory Manual*. Cold Spring Harbor Press) and used to screen commercial human brain cDNA libraries (Stratagene, La Jolla, Calif.). The screening of cDNA libraries follows standard methods and includes such protocols as infecting bacteria with recombinant lambda phage, immobilizing lambda DNA to nitrocellulose filters and screening under medium hybridization stringency conditions with radiolabeled probe. cDNA clones homologous to the probe are identified by autoradiography. Positive clones are purified by sequential rounds of screening.

Following this protocol, most purified cDNA's are likely to be partial sequence clones due the nature of the cDNA library synthesis. Full length clones are constructed from cDNA's which overlap in DNA sequence. Restriction enzyme sites which overlap between cDNAs are used to ligate the individual cDNA's to generate a full-length cDNA. For subsequent heterologous expression, the full-length cDNA is subcloned directly into an appropriate vertebrate expression vector, such as pcDNA-3 (Invitrogen, San Diego, Calif.) in which expression of the cDNA is under the control of a promoter such as the CMV major intermediate early promoter/enhancer. Other suitable expression vectors include, for example, pMT2, pRC/CMV, pcDNA3.1, and pCEP4.

Following these protocols, as described more fully in Example 4, full length mammalian $\alpha_{1G}$, $\alpha_{1H}$ and $\alpha_{1I}$ calcium channel subunit cDNAs were isolated by using the 567 base pair human fragment (Seq. ID No. 19) to screen a rat brain cDNA library. Sequencing of the recovered sequences identified the three distinct classes of calcium channel subunits which have been demoninated herein as $\alpha_{1G}$, $\alpha_{1H}$ and $\alpha_{1I}$ subunits. For each class of subunit, complete sequencing of the largest cDNA confirmed that it represented only a portion of the predicted calcium channel coding region. Complete sequences for the three new subunits were obtained by rescreening the rat brain cDNA library with probes derived from the partial length cDNAs to obtain overlapping segments. These segments were combined to form a complete gene by restriction digestion and ligation. The complete cDNA sequences of the rat $\alpha_{1G}$, $\alpha_{1H}$ and $\alpha_{1I}$ subunits are given by Sequence ID Nos. 23, 25 and 27, respectively. Corresponding amino acid sequences are given by Sequence ID Nos. 24, 26 and 28. The same techniques are employed to recover human sequences by screening of a human or other mammalian library. Thus, for example, partial length human sequences for $\alpha_{1G}$ and $\alpha_{1H}$ T-type calcium channels have been recovered using the same probe (Seq. ID NO. 19) and the full length rat $\alpha_{1I}$ cDNA (Seq. ID. No. 27) has been used to recover a partial length DNA encoding a human $\alpha_{1I}$ T-type calcium channel. The DNA and amino acid sequences for these partial length human calcium channels are given by Seq. ID Nos. 30-35.

Once the full length cDNA is cloned into an expression vector, the vector is then transfected into a host cell for expression. Suitable host cells include *Xenopus oocytes* or mammalian cells such as human embryonic kidney cells as described in International Patent Publication No. WO 96/39512 which is incorporated herein by reference and Ltk cells as described in U.S. Pat. No. 5,386,025 which is incorporated herein by reference. Transfection into host cells may be accomplished by microinjection, lipofection, glycerol shock, electroporation calcium phosphate or particle-mediated gene transfer. The vector may also be transfected into host cells to provide coexpression of the novel $\alpha_1$ subunits with a $\beta$ and/or an $\alpha_2\delta$ subunit.

To confirm that the three full length cDNAs (sequence ID Nos. 23, 25 and 27) encoded function calcium channels, the $\alpha_{1G}$ and $\alpha_{1I}$ cDNAs were transiently transfected into human embryonic kidney cells and evaluated using electrophysiological recording techniques. As described in more detail in Example 5 below, and as illustrated in FIGS. 1-4), the results are consistent with a role of these subunits in native T-type channels in nerve, muscle and endocrine cells.

The resulting cell lines expressing functional calcium channels including the novel $\alpha_1$ subunits of the invention can be used test compounds for pharmacological activity with respect to these calcium channels. Thus, the cell lines are useful for screening compounds for pharmaceutical utility. Such screening can be carried out using several available methods for evaluation of the interaction, if any, between the test compound and the calcium channel. One such method involves the binding of the radiolabeled agents that interact with the calcium channel and subsequent analysis of equilibrium binding measurements including but not limited to, on rates, off rates, $K_d$ values and competitive binding by other methods. Another such method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes the loading the cell lines with a fluorescent dye sensitive to intracellular calcium concentration and subsequent examination of the effects of compounds on the ability of depolarization by potassium chloride or other means to alter intracellular calcium levels. Compounds to be tested as agonists or antagonists of the novel $\alpha_{1I}$ calcium channel subunits are combined with cells that are stably or transiently transformed with a DNA sequence encoding the $\alpha_{1G}$, $\alpha_{1H}$ and $\alpha_{1I}$ calcium channel subunits of the invention and monitored using one of these techniques.

DNA fragments with sequences given by SEQ ID Nos. 13-17 and 19, or polynucleotides with the complete coding sequences as given by Sequence ID Nos. 23, 25 and 27 or distinctive portions thereof which do not exhibit non-discriminatory levels of homology with other types of calcium channel subunits may also be used for mapping the distribution of $\alpha_{1G}$, $\alpha_{1H}$ and $\alpha_{1I}$ calcium channel subunits within a tissue sample. This method follows normal histological procedures using a nucleic acid probe, and generally involves the steps of exposing the tissue to a reagent comprising a directly or indirectly detectable label coupled to a selected DNA fragment, and detecting reagent that has bound to the tissue. Suitable labels include fluorescent labels, enzyme labels, chromophores and radio-labels.

EXAMPLE 1

In order to isolate novel human calcium channel $\alpha_1$ subunits using standard molecular cloning protocols, synthetic DNA probes are prepared, radiolabeled with $^{32}P$ and utilized to screen human cDNA libraries commercially available in lambda phage vectors (Stratagene, La Jolla, Calif.) based on the human DNA sequences for H55225, H55617, H55223, and H55544. DNA fragments with the sequence of sequence ID Nos 17 and 19 may also be used for this purpose. Positive phage are purified through several rounds of screening involving immobilizing the phage DNA on nitrocellulose filters, hybridizing with the radiolabeled probe, washing off of excess probe and then selection of clones by autoradiography. Clones identified by this approach are expected to be partial length clones due to the nature of cDNA library synthesis and several rounds of screening for each calcium channel type may be necessary to obtain full-length clones.

To characterize the clones, double stranded plasmid DNA is prepared from the identified clones and the sequences are determining using $^{35}$S dATP, Sequenase and standard gel electrophoresis methods. Regions of similarity and regions of overlap are determined by comparison of each cDNA sequence.

Full-length clones are constructed by ligating overlapping cDNA fragments together at common restriction enzyme sites. The full-length clones are subsequently inserted into vectors suitable for expression in vertebrate cells (e.g. pMT2, pRC/CMV, pcDNA3.1, pCEP4, pREP7) by ligation into restriction sites in the vector polylinker region which is downstream of the promoter used to direct cDNA expression.

DNA encoding the novel calcium channels can be stably or transiently introduced into eukaryotic cells (e.g. human embryonic kidney, mouse L cells, chinese hamster ovary, etc) by any number of available standard methods. Stable transfection is achieved by growing the cells under conditions that promote growth of cells expressing a marker gene which is contained in the expression vector (e.g. dihydrofolate reductase, thymidine kinase, or the like). The heterlogous DNA encoding the human calcium channel may be integrated into the genome or may be maintained as an episomal element.

Expression of the human calcium channel in transfected cells may monitored by any number of techniques, including Northern blot for RNA analysis, Southern blot for cDNA detection, electrophysiological assay for calcium channel function, the binding of radiolabeled agents thought to interact with the calcium channel, and fluorescent assay of dyes sensitive to intracellular calcium concentration.

EXAMPLE 2

Heterologous Expression of Mammalian $\alpha_{1I}$ Calcium Channels in Cells

A. Transient Transfection in Mammalian Cells

Host cells, such as human embryonic kidney cells, HEK 293 (ATCC# CRL 1573) are grown in standard DMEM medium supplemented with 2 mM glutamine and 10% fetal bovine serum. HEK 293 cells are transfected by a standard calcium-phosphate-DNA co-precipitation method using a full-length mammalian $\alpha_{1I}$ calcium channel cDNA (for example, Seq. ID No. 27) in a vertebrate expression vector (for example see Current protocols in Molecular Biology). The $\alpha_{1I}$ calcium channel cDNA may be transfected alone or in combination with other cloned subunits for mammalian calcium channels, such as $\alpha 2\delta$ and $\beta$ subunits, and also with clones for marker proteins such the jellyfish green fluorescent protein.

Electrophysiological Recording: After an incubation period of from 24 to 72 hrs the culture medium is removed and replaced with external recording solution (see below). Whole cell patch clamp experiments are performed using an Axopatch 200B amplifier (Axon Instruments, Burlingame, Calif.) linked to an IBM compatible personal computer equipped with pCLAMP software. Microelectrodes are filled with 3 M CsCl and have typical resistances from 0.5 to 2.5 MΩ. The external recording solution is 20 mM BaCl$_2$, 1 mM MgCl$_2$, 10 mM HEPES, 40 mM TEAC1, 10 mM Glucose, 65 mM CsCl, (pH 7.2). The internal pipette solution is 105 mM CsCl, 25 mM TEAC1, 1 mM CaCl$_2$, 11 mM EGTA, 10 mM HEPES (pH 7.2). Currents are typically elicited from a holding potential of −100 mV to various test potentials. Data are filtered at 1 kHz and recorded directly on the harddrive of a personal computer. Leak subtraction is carried out on-line using a standard P/5 protocol. Currents are analyzed using pCLAMP versions 5.5 and 6.0. Macroscopic current-voltage relations are fitted with the equation $I=\{1/(1+\exp(-(V_m-V_h)/S\}\times G-(V_m-E_{rev})$, where $V_m$ is the test potential, $V_h$ is the voltage at which half of the channels are activated, and S reflects the steepness of the activation curve and is an indication of the effective gating charge movement. Inactivation curves are normalized to 1 and fitted with $I=(1/1+\exp((V_m-V_h)/S)$ with $V_m$ being the holding potential. Single channel recordings are performed in the cell-attached mode with the following pipette solution (in mM): 100 BaCl$_2$, 10 HEPES, pH 7.4 and bath solution: 100 KCl, 10 EGTA, 2 MgCl$_2$, 10 HEPES, pH 7.4.

B. Transient Transfection in *Xenopus Oocytes*

Stage V and VI *Xenopus oocytes* are prepared as described by Dascal et al (1986), Expression and modulation of voltage-gated calcium channels after RNA injection into *Xenopus oocytes*. Science 231:1147-1150. After enzymatic dissociation with collagenase, oocytes nuclei are microinjected with the human $\alpha_{1I}$ calcium channel cDNA expression vector construct (approximately 10 ng DNA per nucleus) using a Drummond nanojet apparatus. The $\alpha_{1I}$ calcium channel may be injected alone, or in combination with other mammalian calcium channel subunit cDNAs, such as the $\alpha 2$-$\delta$ and $\beta 1b$ subunits. After incubation from 48 to 96 hrs macroscopic currents are recorded using a standard two microelectrode voltage-clamp (Axoclamp 2A, Axon Instruments, Burlingame, Calif.) in a bathing medium containing (in mM): 40 Ba(OH)$_2$, 25 TEA-OH, 25 NaOH, 2 CsOH, 5 HEPES (pH titrated to 7.3 with methan-sulfonic acid). Pipettes of typical resistance ranging from 0.5 to 1.5 mΩ are filled with 2.8M CsCl, 0.2M CsOH, 10 mM HEPES, 10 mM BAPTA free acid. Endogenous Ca (and Ba)-activated C1 currents are suppressed by systematically injecting 10-30 nl of a solution containing 100 mM BAPTA-free acid, 10 mM HEPES (pH titrated to 7.2 with CsOH) using a third pipette connected to a pneumatic injector. Leak currents and capacitive transients are subtracted using a standard P/5 procedure.

EXAMPLE 3

Construction of Stable Cell Lines Expressing Mammalian $\alpha_{1I}$ Calcium Channels Mammalian cells lines stably expressing human $\alpha_{II}$ calcium channels are constructed by transfecting the $\alpha_{1I}$ calcium channel cDNA into mammalian cells such as HEK 293 and selecting for antibiotic resistance encoded for by an expression vector. Briefly, a full-length mammalian $\alpha_{1I}$ calcium channel cDNA (for example Seq. ID NO. 27) subcloned into a vertebrate expression vector with a selectable marker, such as the pcDNA3 (InvitronGen, San Diego, Calif.), is transfected into HEK 293 cells by calcium phosphate coprecipitation or lipofection or electroporation or other method according to well known procedures (Methods in Enzymology, Volume 185, Gene Expression Technology (1990) Edited by Goeddel, D. V.). The $\alpha_{1I}$ calcium channel may be transfected alone, or in combination with other mammalian calcium channel subunit cDNAs, such as the α2-δ and β1b subunits, either in a similar expression vector or other type of vector using different selectable markers. After incubation for 2 days in nonselective conditions, the medium is supplemented with Genetics (G418) at a concentration of between 600 to 800 ug/ml. After 3 to 4 weeks in this medium, cells which are resistant to G418 are visible and can be cloned as isolated colonies using standard cloning rings. After growing up each isolated colony to confluency to establish cell lines, the expression of $\alpha_{1I}$ calcium channels can be determined at with standard gene expression methods such as Northern blotting, RNase protection and reverse-transcriptase PCR.

The functional detection of $\alpha_{1I}$ calcium channels in stably transfected cells can be examined electrophysiologically, such as by whole patch clamp or single channel analysis (see above). Other means of detecting functional calcium channels include the use of radiolabeled $^{45}Ca$ uptake, fluorescence spectroscopy using calcium sensitive dyes such as FURA-2, and the binding or displacement of radiolabeled ligands that interact with the calcium channel.

EXAMPLE 4

In order to recover full-length mammalian sequences for novel calcium channels, the 567 base pair partial length human brain $\alpha_{f1}$ cDNA was gel-purified, radio-labeled with $^{32}P$ dATP and dCTP by random printing (Feinberg et al., 1983, *Anal. Biochem.* 132: 6-13) and used to screen a rat brain cDNA library constructed in the phase vector Lambda Zapp II. (Snutch et al., 1990, *Proc Natl Acad Sci (USA)* 87:3391-3395). Screening was carried out at 62° C. in 5×SSPE (1×SSPE=0.18 m NaCl; 1 mM EDTA; 10 mM sodium phosphate, pH=7.4 0.3% SDS, 0.2 mg/ml denatured salmon sperm DNA). Filters were washed at 62° C. in 0.2×SSPE/0.1% SDS. After three rounds of screening and plaque purification, positive phages were transformed into Bluescript phagemids (Stratagene, La Jolla, Calif.) by in vivo excision.

Double stranded DNA sequences on the recombinant phagemids was performed using a modified dideoxynucleotide protocol (Biggin et al., 1983, *Proc Natl Acad Sci (USA)* 80:3963-3965) and Sequenase version 2.1 (United States Biochemical Corp.). DNA sequencing identified three distinct classes of calcium channel $\alpha_1$ subunits: designated as $\alpha_{1G}$, $\alpha_{1H}$ and $\alpha_{1I}$ calcium channel subunits.

For each class of calcium channel $\alpha_1$ subunit, the largest cDNA was completely sequenced and determined to represent only a portion of the predicted calcium channel coding region. In order to isolate the remaining portions of $\alpha_{1G}$ and $\alpha_{1I}$ calcium channel subunits, the $\alpha_{1G}$ clone was digested with HindIII and SpeI. The resulting 540 base pair fragment was gel purified, radiolabeled with $^{32}P$ dATP and dCTP by random priming and used to rescreen the rat brain cDNA library as described above. The sequence of the 540 base pair $\alpha_{1G}$ screening probe used is given by Seq. ID NO. 29. Other sequences spanning regions of distinctiveness within the sequences for the subunits could also be employed.

Double-stranded DNA sequencing of the purified recombinant phagemids showed that additional $\alpha_{1G}$, $\alpha_{1H}$ and $\alpha_{1I}$ calcium channel subunit cDNAs overlapped with the original partial length cDNA and together encoded complete protein coding regions as well as portions of their respective 5' and 3' non-coding untranslated regions.

To recover further human sequences for the novel $\alpha_{1G}$ and $\alpha_{1H}$ calcium channels, the 567 base pair partial lengths human brain $\alpha_{1I}$ cDNA (Seq. 19) was radio-labelled with $^{32}P$ dATP and dCTP by random priming and used to screen a commercial human thalamus cDNA library (Clontech). Hybridization was performed overnight at 65° C. in 6×SSPE; 0.3% SDS; 5×Denhardt's. Filters were washed at 65° C. in 0.1×SSPE/0.3% SDS. After four rounds of screening and plaque purification, positive phages were selected, DNA prepared and the insert cDNA excised form the lambda vector by digestion with Eco R1 restriction enzyme. The excised cDNA was subcloned into the plasmid Bluescript KS (Stratagene, La Jolla, Calif.) and the DNA sequence determined using a modified dideoxynucleotide protocol and Sequenase version 2.1. The partial length $\alpha_{1G}$ cDNA isolated consisted of 2212 base pairs of which 279 base pairs were 5' noncoding and 1,933 base pairs were coding region representing 644 amino acids (Seq. ID Nos. 30, 31). The partial $\alpha_{1H}$ cDNA isolated consisted of 1,608 base pairs of which 53 base pairs were 5' noncoding and 1,555 were coding region representing 518 amino acids (Seq. ID Nos. 32, 33).

To recover further human sequences for the novel $\alpha_{1I}$ calcium channel, the full-length rat brain α1I cDNA (Seq. 27) was radio-labelled $^{32}P$ dATP and dCTP by random priming and used to screen a commercial human hippocampus cDNA library (Stratagene). Hybridization was performed overnight at 65° C. in 6×SSPE; 0.3% SDS; 5×Denhardt's. Filters were washed at 65° C. in 0.1×SSPE/0.3% SDS. After four rounds of screening and plaque purification, positive phages were transformed into Bluescript phagemids (Stratagene, LA Jolla, Calif.) by in vitro excision. The excised cDNA DNA sequence was determined using a modified dideoxynucleotide protocol and Sequenase version 2.1. The partial $\alpha_{1I}$ cDNA isolated consisted of 1,080 base pairs of coding region representing 360 amino acids (Seq. ID Nos. 34, 35).

EXAMPLE 5

Double-stranded DNA sequencing of the purified recombinant phagemids showed that additional $\alpha_{1G}$ and $\alpha_{1I}$ calcium channel cDNAs overlapped with the original partial length cDNAs and together encoded complete protein encoding regions as well as portions of their respective 5' and 3' non-coding untranslated regions. (Seq. ID Nos. 23 and 27, respectively) In addition to the $\alpha_{1G}$ and $\alpha_{1I}$ calcium channel classes, DNA sequencing of the recombinant phagemids also identified a third class of calcium channel $\alpha_1$ subunit: designated as the $\alpha_{1H}$ calcium channel subunit. The partial length $\alpha_{1H}$ calcium channel cDNAs overlapped and together encoded a complete $\alpha_{1H}$ coding region as well as portions of the 5' and 3' untranslated regions (Seq. ID No. 25).

Electrophysiological studies were performed on transiently-transfected human embryonic kidney cells (HEK-tsa201) prepared using the general protocol of Example 2. Transfection was carried out by standard calcium phosphate precipitation. (Okayama et al., 1991, *Methods in Molec. Biol.*, Vol. 7, ed. Murray, E. J.). For maintenance, HEK-tsa201 cells were cultured until approximately 70% confluent, the media removed and cells dispersed with trypsin and gentle trituration. Cells were then diluted 1:10 in culture medium (10% FBS, DMEM plus L-glutamine, pen-strp) warmed to 37° C. and plated onto tissue culture dishes. For transient transfection, 0.5 mM $CaCl_2$ was mixed with a total of 20 μg of DNA (consisting of 3 μg of either rat brain $\alpha_{1G}$ and $\alpha_{1I}$ calcium channel cDNA, 2 μg of CD8 plasmid marker, and 15 μg of Bluescript plasmid carrier DNA). The DNA mixture was mixed thoroughly and then slowly added dropwise to 0.5 ml of 2 times HeBS (274 mM NaCl, 20 mM D-glucose, 10 mM KCl, 1.4 mM $Na_2HPO_4$, 40 mM Hepes (pH=7.05). After incubation at room temperature for 20 min, 100 µl of the DNA mixture was slowly added to each dish of HEK-tsa201 cells and then incubated at 37° C. for 24 to 48 hours in a tissue culture incubator (5% $CO_2$).

Positive transfectant cells were identified visually by addition of 1 µl of mouse CD8 (Lyt2) Dynabeads directly to the recording solution and gentle swirling to mix. Whole cell patch clamp readings were carried out with an Axopatch 200A amplifier (Axon Instruments) as described previously. (Zamponi et al., 1997, *Nature* 385: 442-446). The external recording solution was 2 mM $CaCl_2$, 10 mM HEPES, 40 mM TEA-Cl, 10 mM glucose, 92 mM CsCl, pH=7.2 with TEA-hydroxide. The internal pipette solution was 105 mM CsCl, 25 mM TEA-Cl, 1 mM $CaCl_2$, 11 mM EGTA, 10 mM HEPES, pH 7.2 with NaOH.

For determination of current-voltage (1-V) relationships, cells were held at a resting potential of –100 mV and then stepped to various depolarizing test potentials. For steady-state inactivation, cells were held at various potentials for 20 sec. and currents recorded during a subsequent test pulse to the peak potential of the I-V. Leak currents and capacitative transients were subtracted using a P/5 procedure.

Figure 1B:
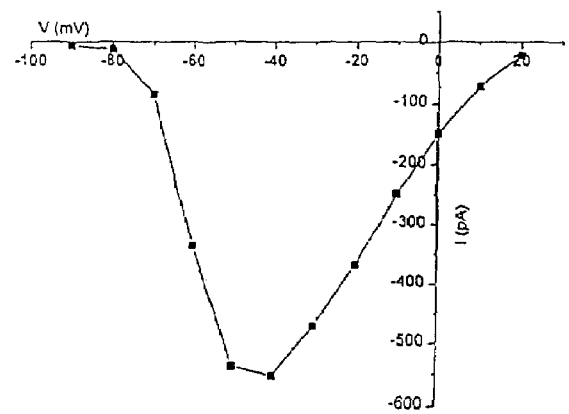

FIGS. 1-4 show the results obtained for HEK cells transfected with and expressing the cDNA of sequences ID Nos. 23 and 27, which correspond to the subunits designated as $\alpha_{1G}$ and $\alpha_{1I}$. FIGS. 1A and B and 2A and B shows a comparison of the waveforms and current-voltage relationship for the two channel subunit types. In the presence of recording solution containing 2 mM $Ca^{2+}$, both the $\alpha_{1G}$ and $\alpha_{1I}$ channel subunits exhibit activation properties consistent with native T-type calcium currents. FIGS. 1 A and 2A show the subunit calcium current from a cell held at –120 mV and depolarized to a series of test potentials. FIGS. 1B and 2B show the magnitude of the calcium current. From a holding potential of –110 mV, both channel first activate at approximately –70 mV and peak currents are obtained between –40 and –50 mV. Upon depolarization to various test potentials, the current waveforms of the $\alpha_{1G}$ and $\alpha_{1I}$ calcium channels exhibit an overlapping pattern characteristic of native T-type channels in nerve, muscle and endocrine cells.

Figure 3:
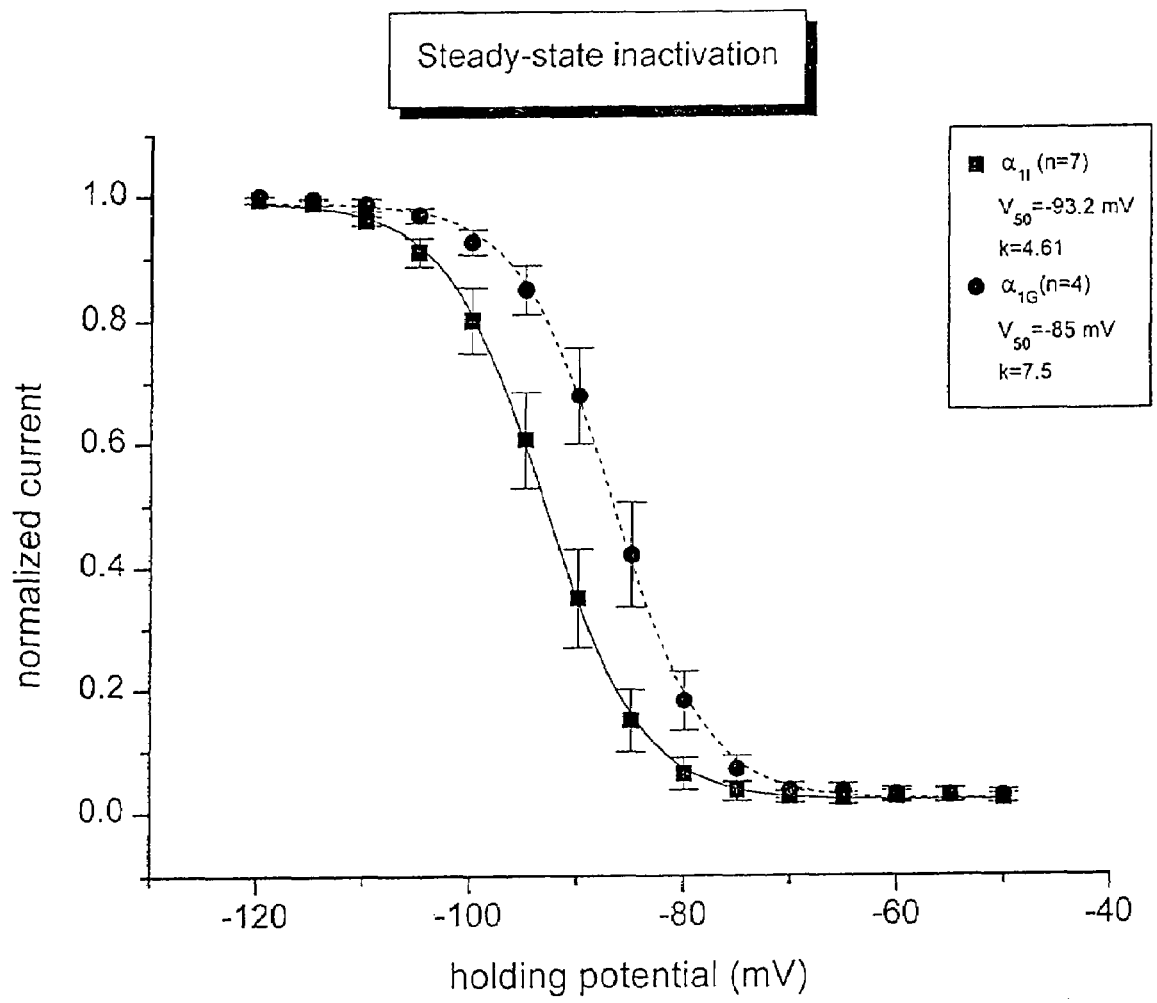
FIG. 3 shows a comparison of the steady state inactivation profiles of the $\alpha_{1G}$ and $\alpha_{1I}$ calcium channels.

FIG. 3 shows steady-state inactivation profiles for the $\alpha_{1G}$ and $\alpha_{1I}$ calcium channels in HEK 293 cells transiently transformed with full length cDNAs (SEQ ID Nos 23 or 27) for $\alpha_{1G}$ or $\alpha_{1I}$ subunits. Steady state inactivation properties were determined by stepping from –120 mV to prepulse holding potentials between –120 mV and –50 mV for 15 sec. prior to a test potential for –30 mV. The data are plotted as normalized whole cell current versus prepulse holding potential and show that $\alpha_{1G}$ exhibits a $V_{50}$ of approximately –85 mV and $\alpha_{1I}$ a $V_{50}$ of approximately –93 mV. Thus, consistent with native T-type calcium channels, both of the $\alpha_{1G}$ and $\alpha_{1I}$ calcium channels exhibit pronounced steady-state inactivation at negative potentials.

FIGS. 4A-C show a comparison of the voltage-dependent deactivation profiles of the $\alpha_{1G}$ and $\alpha_{1I}$ calcium channels. KEK 293 cells were transiently transfected with either an $\alpha_{1G}$ or $\alpha_{1I}$ subunit cDNA (Seq. ID No. 23 or 27). The deactivation properties of $\alpha_{1G}$ were determined by stepping from a holding potential of –100 mV to –40 mV for 9 msec, and then to potentials between –120 mV and –45 mV. The deactivation properties of $\alpha_{I1}$ were determined by stepping from a holding potential of –100 mV to –40 mV for 20 msec, and then to potentials between –120 mV and –45 mV. Both channels exhibit slow deactivation kinetics compared to typical high-threshold channels, and is consistent with the $\alpha_{1G}$ and $\alpha_{1I}$ subunits being subunits for T-type calcium channels.

---

What is claimed is:

1. A method to identify an antagonist of a T-type calcium channel which method comprises:
   a) contacting a recombinant cell expressing the $\alpha_1$ subunit of a heterologous T-type calcium channel with a known agonist of said T-type calcium channel;
   b) contacting said cell with a compound to be tested; and
   c) determining the ability of said compound to diminish the activation of said $\alpha_1$ subunit by said agonist;
   wherein said $\alpha_1$ subunit is functional as a T-type calcium ion channel and is encoded by the nucleotide sequence of SEQ ID NO: 23 and
   wherein said activating comprises enhancing the flow of calcium ions into said cell in the presence as compared to the absence of said agonist;
   whereby a compound which diminishes the activation of said $\alpha_1$ subunit by said agonist is identified as an antagonist.

2. The method of claim 1 wherein said activation is measured by measuring the current through the calcium channel before and after said contacting of said cell with said compound.

3. The method of claim 1 wherein said cell contains fluorescent dye sensitive to intracellular calcium concentration and said activation is determined by observing a change in the fluorescence of said dye when said contacting is performed.

4. A method to prescreen compounds as agonists or antagonists of T-type calcium ion channels by virtue of their ability to bind said T-type channels which method comprises:
   a) contacting a recombinant cell expressing the $\alpha_1$ subunit of a heterologous T-type calcium channel with a compound to be tested; and
   b) determining the ability of said compound to bind to said cell expressing said $\alpha_1$ subunit;
   wherein said binding is determined by observing competitive binding with a known agonist or antagonist of said channel,
   wherein said $\alpha_1$ subunit is functional as a T-type calcium ion channel and is encoded by the nucleotide sequence of SEQ ID NO: 23,
   whereby a compound which is determined to bind said cell is identified as a compound which will behave as either an agonist or antagonist of a T-type calcium channel.

* * * * *

SEQUENCE LISTING

<160> NUMBER OF SEQ ID NOS: 35

<210> SEQ ID NO 1
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 1
gtcaaaactc aggccttcta ctgg                                          24

<210> SEQ ID NO 2
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 2
aacgtgttct tggctatcgc ggtg                                          24

<210> SEQ ID NO 3
<211> LENGTH: 24
<212> TYPE: DNA

```
<213> ORGANISM: rat
<220> FEATURE:
<223> OTHER INFORMATION: oligonucleotide probe for locating calcium
      channel genes

<400> SEQUENCE: 3
gtgaaagcac agagcttcta ctgg                                      24

<210> SEQ ID NO 4
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 4
aacgttttct tggccattgc tgtg                                      24

<210> SEQ ID NO 5
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 5
gttaaatcca acgtcttcta ctgg                                      24

<210> SEQ ID NO 6
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 6
aatgtgttct tggccattgc ggtg                                      24

<210> SEQ ID NO 7
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 7
gtgaagtctg tcacgtttta ctgg                                      24

<210> SEQ ID NO 8
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 8
aagctcttct tggccattgc tgta                                      24

<210> SEQ ID NO 9
<211> LENGTH: 24
<212> TYPE: DNA
<213> ORGANISM: rat
```

```
<220> FEATURE:
<223> OTHER INFORMATION: oligonucleotide probe for locating calcium
      channel genes

<400> SEQUENCE: 9
gtcaagtcgc aagtgttcta ctgg                                           24

<210> SEQ ID NO 10
<211> LENGTH: 24
<212> TYPE: DNA
<213> ORGANISM: rat
<220> FEATURE:
<223> OTHER INFORMATION: oligonucleotide probe for locating calcium
      channel genes

<400> SEQUENCE: 10
aatgtattct tggctatcgc tgtg                                           24

<210> SEQ ID NO 11
<211> LENGTH: 21
<212> TYPE: DNA
<213> ORGANISM: rat
<220> FEATURE:
<223> OTHER INFORMATION: oligonucleotide probe for locating calcium
      channel genes

<400> SEQUENCE: 11
atctaygcyr tsatyggsat g                                              21

<210> SEQ ID NO 12
<211> LENGTH: 20
<212> TYPE: DNA
<213> ORGANISM: rat
<220> FEATURE:
<223> OTHER INFORMATION: oligonucleotide probe for locating calcium
      channel genes

<400> SEQUENCE: 12
atggacaayt tygastaytc                                                20

<210> SEQ ID NO 13
<211> LENGTH: 168
<212> TYPE: DNA
<213> ORGANISM: HUMAN
<220> FEATURE:
<223> OTHER INFORMATION: expressed sequence tag H55225

<400> SEQUENCE: 13
gtgatcactc tggaaggctg ggtggagatc atgtactacg tgatggatgc tcactccttc    60
tacaacttca tctacttcat cctgcttatc atacccctct tgccttgcac cccatatggt   120
cttcccagag tgagctcatc cacctcgtca tgcctgactc gacgttca                168

<210> SEQ ID NO 14
<211> LENGTH: 98
<212> TYPE: DNA
<213> ORGANISM: HUMAN
<220> FEATURE:
<223> OTHER INFORMATION: expressed sequence tag H55617

<400> SEQUENCE: 14
gatggtcgag tactccctgg accttcagaa catcaacctg tcagccatcc gcaccgtgcg    60
cgtcctgagg cccctcaaag ccatcaaccg cgtgccca                            98

<210> SEQ ID NO 15
```

```
<211> LENGTH: 94
<212> TYPE: DNA
<213> ORGANISM: HUMAN
<220> FEATURE:
<223> OTHER INFORMATION: expressed sequence tag H55223

<400> SEQUENCE: 15
catgctggtg atcctgctga actgcgtgac acttggcatg taccagccgt gcgacgacat    60
ggactgcctg tccgaccgct gcaagatcct gcag                                94

<210> SEQ ID NO 16
<211> LENGTH: 123
<212> TYPE: DNA
<213> ORGANISM: HUMAN
<220> FEATURE:
<223> OTHER INFORMATION: expressed sequence tag H55544

<400> SEQUENCE: 16
gtatctctgg ttactttagt agccaacact cttggctact cagaccttgg tcccattaaa    60
tccctgcgaa ccttgagagc actaagacct ctaagagctt tgtctagatt tgaaggaatg   120
agg                                                                 123

<210> SEQ ID NO 17
<211> LENGTH: 5562
<212> TYPE: DNA
<213> ORGANISM: HUMAN
<220> FEATURE:
<223> OTHER INFORMATION: human alpha-I partial sequence from BAC bK206c7

<400> SEQUENCE: 17 atgttttcg tctcagccaa tccctgggtg agtttcacca gttttgattt aaacgtggcc     60
aatatggaca acttcttcgc ccccgttttc accatgggca atattatac gcaaggcgac    120 aaggtgctga tgccgctggc gattcaggct ctgaaacagc tgatgttcaa attggtggcc   180
actgttgctc gaacacatgc tacaccgtca cacatcacgg gtggtcctgg aacagggatg   240
cacacgggca ccttccagga aggagctgag cctggttcat ctcagcaccc tgaggcacag   300
gccacgtata cagcagggtg cacccccagcc cccacgggcg atcccacctg ctgctttgtc   360
cttgacttgg tgtgcacgtg gtttgaatgt gtcagcatgc tggtgatcct gctgaactgc   420
gtgacacttg gcatgtacca gccgtgcgac gacatggact gcctgtccga ccgctgcaag   480
atcctgcagg tctttgatga cttcatcttt atcttctttg ccatggagat ggtgctcaag   540
atggtggccc tggggatttt tggcaagaag tgctacctcg ggacacatg gaaccgcctg    600 gatttcttca tcgtcatggc aggcaacatc aacctgtcag ccatccgcac cgtgcgcgtc   660
ctgaggcccc tcaaagccat caaccgcgtg cccagtatgc ggatcctggt gaacctgctc   720
ctggacacac tgcccatgct ggggaatgtc ctgctgctct gcttctttgt cttcttcatc   780 tttgcatca taggtgtgca gctctgggcg ggcctgctgc gtaaccgctg cttcctggag   840
gagaacttca ccatacaagg ggatgtggcc ttgccccat actaccagcc ggaggaggat    900
gatgagatgc ccttcatctg ctccctgtcg ggcgacaatg gataatggg ctgccatgag    960 atcccccgc tcaaggagca gggccgtgag tgctgcctgt ccaaggacga cgtctacgac   1020
tttggggcgg ggcgcaggga cctcaatgcc agcggcctct gtgtcaactg gaaccgttac   1080
tacaatgtgt gccgcacggg cagcgccaac ccccacaagg gtgccatcaa ctttgacaac   1140
atcggttatg cttggattgt catcttccag gtgatcactc tggaaggctg ggtggagatc   1200
atgtactacg tgatggatgc tcactccttc tacaacttca tctacttcat cctgctattc   1260
```

-continued

```
ataagtgagc tcatccacct cgtcatgcct gactgcagct tcagcacagc acagtcccca      1320
aaatgtcaag gtgattcact cccaggagtc gctgctgaat ccctgctgct gcgagactct      1380
agctcctcag tcatcactga tgaggctgca gccatggaga acctcctggc gggcacctcc      1440
aagggggatg aaagctatct gctcaggctg gccggcagcc aagttcactc ccaggctcag      1500
caaatgctgg ggaggggct gggccctgaa agcctggaaa ctggagagga gccccactcg       1560
tggagccctc gggccacaag gagatgggat ccccaatgcc aaccagggca gcctctcccc      1620
cttcatttca tgcaagcaca ggtgggctcc ttcttcatga tcaacctgtg cctcgttgtc      1680
atagcgaccc agttctcgga gaccaagcaa cgggagcacc ggctgatgct ggagcagcgg      1740
cagcgctacc tgtcctccag cacggtggcc agctacgccg agcctggcga ctgctacgag      1800
gagatcttcc agtatgtctg ccacatcctg cgcaaggcca agcgccgcgc cctgggcctc      1860
taccaggccc tgcagagccg cgcgccaggc ctgggcccgg aggccccggc ccccgccaaa      1920
cctgggcccc acgccaagga gccccggcac taccctctca cagtctggga atcgattctt      1980
gggaggcaag cagaagaatg cacgctcaga gctgccgccc accgtcctc gggtgccagc       2040 catccaggcg tgggctcgga ggaggcccca gagctgtgcc cgcaacatag ccccctggat      2100
gcgacgcccc acaccctggt gcagcccatc cccgccacgc tggcttccga tcccgccagc      2160
tgcccttgct gccagcatga ggacggccgg cggcctcgg gcctgggcag caccgactcg       2220
ggccaggagg gctcgggctc cgggagctcc gctggtggcg aggacgaggc ggatggggac      2280
ggggcccgga gcagcgagga cggagcctcc tcagaactgg ggaaggagga ggaggaggag      2340
gagcaggcgg atgggcggt ctggctgtgc ggggatgtgt ggcgggagac gcgagccaag       2400
ctgcgcggca tcgtggacag caagtacttc aaccgggga tcatgatggc catcctggtc       2460
aacaccgtca gcatgggcat cgagcaccac gagcaggcca gtgcagcgca gccgggccgg      2520
gcctgcggga gaggacaaaa tccagacctt tgcatgaccc tcaaggcccc ttgtctctgt      2580
cacaacgtcc cttcaccagg ccagggtgtc ctgtcccatc cagtgactcc accccataca      2640
gccccatggc gcatggagac aggaaagcag ggacacggat gtgaagaagg accaggacaa      2700
cgaagcagtg acatgtttgc cctggagatg atcctgaagc tggctgcatt tgggctcttc      2760
gactacctgc gtaaccccta caacatcttc gacagcatca ttgtcatcat cagcatctgg      2820
gagatcgtgg ggcaggcgga cggtgggctg tcggtgctgc ggaccttccg gctgctgcgc      2880
gtgctgaaac tggtgcgctt catgcctgcc ctgcggcgcc agctcgtggt gctcatgaag      2940
accatggaca acgtggccac cttctgcatg ctgctcatgc tcttcatctt catcttcagc      3000
atccttggga tgcatatttt tggctgcaag ttcagcctcc gcacggacac tggagacacg      3060
gtgcccgaca ggaagaactt cgactccctg ctgtgggcca tcgtcactgt gttccagatc      3120
ctcacccagg aggactggaa cgtcgttctc tacaatggca tggcctccac ttctccctgg      3180
gcctccctct actttgtcgc cctcatgacc ttcggcaact atgtgctctt caacctgctg      3240
gtggccatcc tggtgaggg cttccaggcg gaggtgactg tggtcttggc agaggaagca      3300
cccccacagg gcctgcgaaa gactgggcga gggagaggtg gcctggatgg gggagggctg      3360
caattcaaac ttctagcagg caacctatcc ctaaaggagg gggttgctga tgaggtgggt      3420
gacgccaatc gctcctactc ggacgaggac cagagctcat ccaacataga agagtttgat      3480
aagctccagg aaggcctgga cagcagcgga gatcccaagc tctgcccaat ccccatgacc      3540
cccaatgggc acctggaccc cagtctccca ctgggtgggc acctaggtcc tgctggggct      3600
```

```
gcgggacctg ccccccgact ctcactgcag ccggacccca tgctggtggc cctgggctcc    3660
cgaaagagca gcgtcatgtc tctagggagg atgagctatg accagcgctc cctggtgggt    3720
ggtcttagag ccacagcggg ggtgcaggct gcctttgggc acctggtgcc ccagccgtgg    3780
gtgtgcctgt ggggcgctga cccgaacggg aactccttcc agtccagctc ccggagctcc    3840
tactacgggc catggggccg cagcgcggcc tgggccagcc gtcgctccag ctggaacagc    3900
ctcaagcaca agccgccgtc ggcggagcat gagtccctgc tctctgcgga gcgcggcggc    3960
ggcgcccggg tctgcgaggt tgccgcggac gaggggccgc cgcgggccgc acccctgcac    4020
accccacacg cccaccacgt tcatcacggg ccccatctgg cgcaccgcca ccgccaccac    4080
cgccggacgc tgtccctcga acagggac tcggtggacc tggccgagct ggtgcccgcg    4140
gtgggcgccc accccgggc cgcctggagg gcggcaggcc cggcccccgg gcatgaggac    4200
tgcaatggca ggatgcccag catcgccaaa gacgtcttca ccaagatggg cgaccgcggg    4260
gatcgcgggg aggatgagga ggaaatcgac tacgtgagtg ggggcggggc cgaagggac    4320 ctgaccctgt gcttccgcgt ccgcaagatg atcgacgtct ataagcccga ctggtgcgag    4380
gtccgcgaag actggtctgt ctacctcttc tctcccgaga acaggctcag ggatctgggc    4440
tgggtaagcc tcgagtgcca gggaaaggtg ggtgacctcg tggtgtgggt gtatggtcag    4500
aggaggcagc gccagaccat tattgcccac aaactcttcg actacgtcgt cctggccttc    4560
atctttctca actgcatcac catcgccctg agcggcctc agatcgaggc cggcagcacc    4620
gaacgcatct ttctcaccgt gtccaactac atcttcacgg ccatcttcgt gggcgagatg    4680
acattgaagg tagtctcgct gggcctgtac ttcggcgagc aggcgtacct acgcagcagc    4740
tggaacgtgc tggatggctt tcttgtcttc gtgtccatca tcgacatcgt ggtgtccctg    4800
gcctcagccg ggggagccaa gatcttgggg gtcctccgag tcttgcggct cctgcgcacc    4860
ctacgccccc tgcgtgtcat cagccgggcg ccgggcctga agctggtggt ggagacactc    4920
atctcctccc tcaagcccat cggcaacatc gtgctcatct gctgtgcctt cttcatcatc    4980
tttggcatcc tggagtgca gctcttcaag ggcaagttct accactgtct gggcgtggac    5040
acccgcaaca tcaccaaccg ctcggactgc atggccgcca actaccgctg ggtccatcac    5100
aaatacaact tcgacaacct gggccaggct ctgatgtccc tctttgtcct ggcatccaag    5160
gatggttggg tgaacatcat gtacaatgga ctggatgctg ttgctgtgga ccagcagcct    5220
gtgaccaacc acaaccccctg gatgctgctg tacttcatct ccttcctgct catcgtcagc    5280
ttctttgtgc tcaacatgtt tgtgggtgtc gtggtggaga acttccacaa gtgccggcag    5340
caccaggagg ctgaagaggc acggcggcgt gaggagaagc ggctgcggcg cctggagaag    5400
aagcgccgga aggcccagcg gctgcccctac tatgccacct attgtcacac ccggctgctc    5460
atccactcca tgtgcaccag ccactacctg gacatcttca tcaccttcat catctgcctc    5520
aacgtggtca ccatgtcccct ggagcactac aatcagccca cg                      5562
```

<210> SEQ ID NO 18
<211> LENGTH: 1854
<212> TYPE: PRT
<213> ORGANISM: HUMAN
<220> FEATURE:
<223> OTHER INFORMATION: human alpha-I partial sequence from BAC bK206c7

<400> SEQUENCE: 18

```
Met Phe Phe Val Ser Ala Asn Pro Trp Val Ser Phe Thr Ser Phe Asp
 1               5                  10                  15
```

-continued

```
Leu Asn Val Ala Asn Met Asp Asn Phe Phe Ala Pro Val Phe Thr Met
         20                  25                  30
Gly Lys Tyr Tyr Thr Gln Gly Asp Lys Val Leu Met Pro Leu Ala Ile
         35                  40                  45
Gln Ala Leu Lys Gln Leu Met Phe Lys Leu Val Ala Thr Val Ala Arg
 50                  55                  60
Thr His Ala Thr Pro Ser His Ile Thr Gly Gly Pro Gly Thr Gly Met
 65                  70                  75                  80
His Thr Gly Thr Phe Gln Glu Gly Ala Glu Pro Gly Ser Ser Gln His
             85                  90                  95
Pro Glu Ala Gln Ala Thr Tyr Thr Ala Gly Cys Thr Pro Ala Pro Thr
            100                 105                 110
Gly Asp Pro Thr Cys Cys Phe Val Leu Asp Leu Val Cys Thr Trp Phe
            115                 120                 125
Glu Cys Val Ser Met Leu Val Ile Leu Leu Asn Cys Val Thr Leu Gly
130                 135                 140
Met Tyr Gln Pro Cys Asp Asp Met Asp Cys Leu Ser Asp Arg Cys Lys
145                 150                 155                 160
Ile Leu Gln Val Phe Asp Asp Phe Ile Phe Ile Phe Phe Ala Met Glu
                165                 170                 175
Met Val Leu Lys Met Val Ala Leu Gly Ile Phe Gly Lys Lys Cys Tyr
            180                 185                 190
Leu Gly Asp Thr Trp Asn Arg Leu Asp Phe Phe Ile Val Met Ala Gly
            195                 200                 205
Asn Ile Asn Leu Ser Ala Ile Arg Thr Val Arg Val Leu Arg Pro Leu
210                 215                 220
Lys Ala Ile Asn Arg Val Pro Ser Met Arg Ile Leu Val Asn Leu Leu
225                 230                 235                 240
Leu Asp Thr Leu Pro Met Leu Gly Asn Val Leu Leu Leu Cys Phe Phe
                245                 250                 255
Val Phe Phe Ile Phe Gly Ile Ile Gly Val Gln Leu Trp Ala Gly Leu
            260                 265                 270
Leu Arg Asn Arg Cys Phe Leu Glu Glu Asn Phe Thr Ile Gln Gly Asp
            275                 280                 285
Val Ala Leu Pro Pro Tyr Tyr Gln Pro Glu Glu Asp Asp Glu Met Pro
290                 295                 300
Phe Ile Cys Ser Leu Ser Gly Asp Asn Gly Ile Met Gly Cys His Glu
305                 310                 315                 320
Ile Pro Pro Leu Lys Glu Gln Gly Arg Glu Cys Cys Leu Ser Lys Asp
                325                 330                 335
Asp Val Tyr Asp Phe Gly Ala Gly Arg Gln Asp Leu Asn Ala Ser Gly
            340                 345                 350
Leu Cys Val Asn Trp Asn Arg Tyr Tyr Asn Val Cys Arg Thr Gly Ser
            355                 360                 365
Ala Asn Pro His Lys Gly Ala Ile Asn Phe Asp Asn Ile Gly Tyr Ala
370                 375                 380
Trp Ile Val Ile Phe Gln Val Ile Thr Leu Glu Gly Trp Val Glu Ile
385                 390                 395                 400
Met Tyr Tyr Val Met Asp Ala His Ser Phe Tyr Asn Phe Ile Tyr Phe
                405                 410                 415
Ile Leu Leu Ile Ile Ser Glu Leu Ile His Leu Val Met Pro Asp Cys
            420                 425                 430
Ser Phe Ser Thr Ala Gln Ser Pro Lys Cys Gln Gly Asp Ser Leu Pro
```

-continued

```
            435                 440                 445
Gly Val Ala Ala Glu Ser Leu Leu Arg Asp Ser Ser Ser Val
        450                 455                 460
Ile Thr Asp Glu Ala Ala Ala Met Glu Asn Leu Leu Ala Gly Thr Ser
465                 470                 475                 480
Lys Gly Asp Glu Ser Tyr Leu Leu Arg Leu Ala Gly Ser Gln Val His
                485                 490                 495
Ser Gln Ala Gln Gln Met Leu Gly Arg Gly Leu Gly Pro Glu Ser Leu
            500                 505                 510
Glu Thr Gly Glu Glu Pro His Ser Trp Ser Pro Arg Ala Thr Arg Arg
            515                 520                 525
Trp Asp Pro Gln Cys Gln Pro Gly Gln Pro Leu Pro Leu His Phe Met
530                 535                 540
Gln Ala Gln Val Gly Ser Phe Phe Met Ile Asn Leu Cys Leu Val Val
545                 550                 555                 560
Ile Ala Thr Gln Phe Ser Glu Thr Lys Gln Arg Glu His Arg Leu Met
                565                 570                 575
Leu Glu Gln Arg Gln Arg Tyr Leu Ser Ser Ser Thr Val Ala Ser Tyr
            580                 585                 590
Ala Glu Pro Gly Asp Cys Tyr Glu Glu Ile Phe Gln Tyr Val Cys His
            595                 600                 605
Ile Leu Arg Lys Ala Lys Arg Arg Ala Leu Gly Leu Tyr Gln Ala Leu
        610                 615                 620
Gln Ser Arg Arg Gln Ala Leu Gly Pro Glu Ala Pro Ala Pro Ala Lys
625                 630                 635                 640
Pro Gly Pro His Ala Lys Glu Pro Arg His Tyr Pro Leu Thr Val Trp
                645                 650                 655
Glu Ser Ile Leu Gly Arg Gln Ala Glu Glu Cys Thr Leu Arg Ala Ala
            660                 665                 670
Ala His Pro Ser Ser Gly Ala Ser His Pro Gly Val Gly Ser Glu Glu
        675                 680                 685
Ala Pro Glu Leu Cys Pro Gln His Ser Pro Leu Asp Ala Thr Pro His
        690                 695                 700
Thr Leu Val Gln Pro Ile Pro Ala Thr Leu Ala Ser Asp Pro Ala Ser
705                 710                 715                 720
Cys Pro Cys Cys Gln His Glu Asp Gly Arg Arg Pro Ser Gly Leu Gly
                725                 730                 735
Ser Thr Asp Ser Gly Gln Glu Gly Ser Gly Ser Ser Ala Gly
            740                 745                 750
Gly Glu Asp Glu Ala Asp Gly Asp Gly Ala Arg Ser Ser Glu Asp Gly
            755                 760                 765
Ala Ser Ser Glu Leu Gly Lys Glu Glu Glu Glu Glu Gln Ala Asp
        770                 775                 780
Gly Ala Val Trp Leu Cys Gly Asp Val Trp Arg Glu Thr Arg Ala Lys
785                 790                 795                 800
Leu Arg Gly Ile Val Asp Ser Lys Tyr Phe Asn Arg Gly Ile Met Met
                805                 810                 815
Ala Ile Leu Val Asn Thr Val Ser Met Gly Ile Glu His His Glu Gln
            820                 825                 830
Ala Ser Ala Ala Gln Pro Gly Arg Ala Cys Gly Arg Gly Gln Asn Pro
        835                 840                 845
Asp Leu Cys Met Thr Leu Lys Ala Pro Cys Leu Cys His Asn Val Pro
        850                 855                 860
```

-continued

Ser Pro Gly Gln Gly Val Leu Ser His Pro Val Thr Pro His Thr
865                 870                 875                 880

Ala Pro Trp Arg Met Glu Thr Gly Lys Gln Gly His Gly Cys Glu Glu
                885                 890                 895

Gly Pro Gly Gln Arg Ser Ser Asp Met Phe Ala Leu Glu Met Ile Leu
                900                 905                 910

Lys Leu Ala Ala Phe Gly Leu Phe Asp Tyr Leu Arg Asn Pro Tyr Asn
                915                 920                 925

Ile Phe Asp Ser Ile Ile Val Ile Ile Ser Ile Trp Glu Ile Val Gly
            930                 935                 940

Gln Ala Asp Gly Gly Leu Ser Val Leu Arg Thr Phe Arg Leu Leu Arg
945                 950                 955                 960

Val Leu Lys Leu Val Arg Phe Met Pro Ala Leu Arg Arg Gln Leu Val
                965                 970                 975

Val Leu Met Lys Thr Met Asp Asn Val Ala Thr Phe Cys Met Leu Leu
                980                 985                 990

Met Leu Phe Ile Phe Ile Phe Ser Ile Leu Gly Met His Ile Phe Gly
                995                 1000                1005

Cys Lys Phe Ser Leu Arg Thr Asp Thr Gly Asp Thr Val Pro Asp Arg
            1010                1015                1020

Lys Asn Phe Asp Ser Leu Leu Trp Ala Ile Val Thr Val Phe Gln Ile
1025                1030                1035                1040

Leu Thr Gln Glu Asp Trp Asn Val Val Leu Tyr Asn Gly Met Ala Ser
                1045                1050                1055

Thr Ser Pro Trp Ala Ser Leu Tyr Phe Val Ala Leu Met Thr Phe Gly
                1060                1065                1070

Asn Tyr Val Leu Phe Asn Leu Leu Val Ala Ile Leu Val Glu Gly Phe
            1075                1080                1085

Gln Ala Glu Val Thr Val Val Leu Ala Glu Glu Ala Pro Pro Gln Gly
            1090                1095                1100

Leu Arg Lys Thr Gly Arg Gly Arg Gly Gly Leu Asp Gly Gly Gly Leu
1105                1110                1115                1120

Gln Phe Lys Leu Leu Ala Gly Asn Leu Ser Leu Lys Glu Gly Val Ala
                1125                1130                1135

Asp Glu Val Gly Asp Ala Asn Arg Ser Tyr Ser Asp Glu Asp Gln Ser
            1140                1145                1150

Ser Ser Asn Ile Glu Glu Phe Asp Lys Leu Gln Glu Gly Leu Asp Ser
            1155                1160                1165

Ser Gly Asp Pro Lys Leu Cys Pro Ile Pro Met Thr Pro Asn Gly His
    1170                1175                1180

Leu Asp Pro Ser Leu Pro Leu Gly Gly His Leu Gly Pro Ala Gly Ala
1185                1190                1195                1200

Ala Gly Pro Ala Pro Arg Leu Ser Leu Gln Pro Asp Pro Met Leu Val
                1205                1210                1215

Ala Leu Gly Ser Arg Lys Ser Ser Val Met Ser Leu Gly Arg Met Ser
                1220                1225                1230

Tyr Asp Gln Arg Ser Leu Val Gly Gly Leu Arg Ala Thr Ala Gly Val
            1235                1240                1245

Gln Ala Ala Phe Gly His Leu Val Pro Gln Pro Trp Val Cys Leu Trp
    1250                1255                1260

Gly Ala Asp Pro Asn Gly Asn Ser Phe Gln Ser Ser Ser Arg Ser Ser
1265                1270                1275                1280

-continued

Tyr Tyr Gly Pro Trp Gly Arg Ser Ala Ala Trp Ala Ser Arg Arg Ser
            1285                1290                1295

Ser Trp Asn Ser Leu Lys His Lys Pro Pro Ser Ala Glu His Glu Ser
        1300                1305                1310

Leu Leu Ser Ala Glu Arg Gly Gly Gly Ala Arg Val Cys Glu Val Ala
    1315                1320                1325

Ala Asp Glu Gly Pro Pro Arg Ala Ala Pro Leu His Thr Pro His Ala
1330                1335                1340

His His Val His His Gly Pro His Leu Ala His Arg His Arg His His
1345                1350                1355                1360

Arg Arg Thr Leu Ser Leu Asp Asn Arg Asp Ser Val Asp Leu Ala Glu
            1365                1370                1375

Leu Val Pro Ala Val Gly Ala His Pro Arg Ala Ala Trp Arg Ala Ala
        1380                1385                1390

Gly Pro Ala Pro Gly His Glu Asp Cys Asn Gly Arg Met Pro Ser Ile
    1395                1400                1405

Ala Lys Asp Val Phe Thr Lys Met Gly Asp Arg Gly Asp Arg Gly Glu
    1410                1415                1420

Asp Glu Glu Glu Ile Asp Tyr Val Ser Gly Gly Ala Glu Gly Asp
1425                1430                1435                1440

Leu Thr Leu Cys Phe Arg Val Arg Lys Met Ile Asp Val Tyr Lys Pro
            1445                1450                1455

Asp Trp Cys Glu Val Arg Glu Asp Trp Ser Val Tyr Leu Phe Ser Pro
        1460                1465                1470

Glu Asn Arg Leu Arg Asp Leu Gly Trp Val Ser Leu Glu Cys Gln Gly
    1475                1480                1485

Lys Val Gly Asp Leu Val Val Trp Val Tyr Gly Gln Arg Arg Gln Arg
    1490                1495                1500

Gln Thr Ile Ile Ala His Lys Leu Phe Asp Tyr Val Val Leu Ala Phe
1505                1510                1515                1520

Ile Phe Leu Asn Cys Ile Thr Ile Ala Leu Glu Arg Pro Gln Ile Glu
            1525                1530                1535

Ala Gly Ser Thr Glu Arg Ile Phe Leu Thr Val Ser Asn Tyr Ile Phe
        1540                1545                1550

Thr Ala Ile Phe Val Gly Glu Met Thr Leu Lys Val Val Ser Leu Gly
    1555                1560                1565

Leu Tyr Phe Gly Glu Gln Ala Tyr Leu Arg Ser Ser Trp Asn Val Leu
    1570                1575                1580

Asp Gly Phe Leu Val Phe Val Ser Ile Ile Asp Ile Val Val Ser Leu
1585                1590                1595                1600

Ala Ser Ala Gly Gly Ala Lys Ile Leu Gly Val Leu Arg Val Leu Arg
            1605                1610                1615

Leu Leu Arg Thr Leu Arg Pro Leu Arg Val Ile Ser Arg Ala Pro Gly
        1620                1625                1630

Leu Lys Leu Val Val Glu Thr Leu Ile Ser Ser Leu Lys Pro Ile Gly
    1635                1640                1645

Asn Ile Val Leu Ile Cys Cys Ala Phe Phe Ile Ile Phe Gly Ile Leu
1650                1655                1660

Gly Val Gln Leu Phe Lys Gly Lys Phe Tyr His Cys Leu Gly Val Asp
1665                1670                1675                1680

Thr Arg Asn Ile Thr Asn Arg Ser Asp Cys Met Ala Ala Asn Tyr Arg
            1685                1690                1695

Trp Val His His Lys Tyr Asn Phe Asp Asn Leu Gly Gln Ala Leu Met

-continued

```
                    1700                1705                1710
Ser Leu Phe Val Leu Ala Ser Lys Asp Gly Trp Val Asn Ile Met Tyr
            1715                1720                1725

Asn Gly Leu Asp Ala Val Ala Val Asp Gln Gln Pro Val Thr Asn His
        1730                1735                1740

Asn Pro Trp Met Leu Leu Tyr Phe Ile Ser Phe Leu Leu Ile Val Ser
    1745                1750                1755                1760

Phe Phe Val Leu Asn Met Phe Val Gly Val Val Glu Asn Phe His
                1765                1770                1775

Lys Cys Arg Gln His Gln Glu Ala Glu Ala Arg Arg Glu Glu
            1780                1785                1790

Lys Arg Leu Arg Arg Leu Glu Lys Lys Arg Arg Lys Ala Gln Arg Leu
            1795                1800                1805

Pro Tyr Tyr Ala Thr Tyr Cys His Thr Arg Leu Leu Ile His Ser Met
        1810                1815                1820

Cys Thr Ser His Tyr Leu Asp Ile Phe Ile Thr Phe Ile Ile Cys Leu
1825                1830                1835                1840

Asn Val Val Thr Met Ser Leu Glu His Tyr Asn Gln Pro Thr
            1845                1850
```

<210> SEQ ID NO 19
<211> LENGTH: 567
<212> TYPE: DNA
<213> ORGANISM: HUMAN
<220> FEATURE:
<223> OTHER INFORMATION: human alpha-I partial sequence

<400> SEQUENCE: 19

```
atgcggatcc tggtgaacct gctcctggac acactgccca tgctgggaa tgtcctgctg       60
ctctgcttct ttgtcttctt cacctttggc atcataggtg tgcagctctg ggcgggcctg      120
ctgcgtaacc gctgcttcct ggaggagaac ttcaccatac aagggatgt ggccttgccc       180
ccatactacc agccggagga ggatgatgag atgcccttca tctgctccct gtcgggcgac      240
aatgggataa tggctgcca tgagatcccc ccgctcaagg agcagggccg tgagtgctgc      300
ctgtccaagg acgacgtcta cgactttggg gcggggcgcc aggacctcaa tgccagcggc      360
ctctgtgtca actggaaccg ttactacaat gtgtgccgca cgggcagcgc caaccccac       420
aagggtgcca tcagctttga acacatcggt tatgcttgga ttgtcatctt ccaggtgatc      480
actctggaag ctgggtggc gatcatgtac tacgtgatgg atgctctctc cttctacaac      540
ttcgtctact tcatcctgct tatcata                                         567
```

<210> SEQ ID NO 20
<211> LENGTH: 189
<212> TYPE: PRT
<213> ORGANISM: HUMAN
<220> FEATURE:
<223> OTHER INFORMATION: human alpha-I partial sequence

<400> SEQUENCE: 20

```
Met Arg Ile Leu Val Asn Leu Leu Leu Asp Thr Leu Pro Met Leu Gly
  1               5                  10                  15

Asn Val Leu Leu Leu Cys Phe Phe Val Phe Phe Thr Phe Gly Ile Ile
                20                  25                  30

Gly Val Gln Leu Trp Ala Gly Leu Leu Arg Asn Arg Cys Phe Leu Glu
            35                  40                  45

Glu Asn Phe Thr Ile Gln Gly Asp Val Ala Leu Pro Pro Tyr Tyr Gln
```

-continued

```
                 50                   55                  60
Pro Glu Glu Asp Asp Glu Met Pro Phe Ile Cys Ser Leu Ser Gly Asp
 65                  70                  75                  80

Asn Gly Ile Met Gly Cys His Glu Ile Pro Pro Leu Lys Glu Gln Gly
                 85                  90                  95

Arg Glu Cys Cys Leu Ser Lys Asp Asp Val Tyr Asp Phe Gly Ala Gly
                100                 105                 110

Arg Gln Asp Leu Asn Ala Ser Gly Leu Cys Val Asn Trp Asn Arg Tyr
            115                 120                 125

Tyr Asn Val Cys Arg Thr Gly Ser Ala Asn Pro His Lys Gly Ala Ile
        130                 135                 140

Ser Phe Asp Asn Ile Gly Tyr Ala Trp Ile Val Ile Phe Gln Val Ile
145                 150                 155                 160

Thr Leu Glu Gly Trp Val Ala Ile Met Tyr Tyr Val Met Asp Ala Leu
                165                 170                 175

Ser Phe Tyr Asn Phe Val Tyr Phe Ile Leu Leu Ile Ile
            180                 185
```

<210> SEQ ID NO 21
<211> LENGTH: 567
<212> TYPE: DNA
<213> ORGANISM: rat
<220> FEATURE:
<223> OTHER INFORMATION: rat alpha-I partial sequence

<400> SEQUENCE: 21

```
atgcggatcc tggtgaacct gctgctcgac acgctgccca tgctggggaa cgtgctcctg      60
ctctgttttct tcgtcttctt catcttcggc atcattggcg tgcagctctg ggcaggcctg    120
ctacggaacc gctgcttcct ggaagaaaac ttcaccatac aaggggatgt ggccctgccc    180
ccttattacc aaccagagga ggatgacgag atgcccttta tctgctccct gactggggac    240
aatggcatca tgggctgcca cgagatcccc ccactgaagg agcagggccg ggaatgctgc    300
ctgtccaaag atgatgtgta tgacttcggg gcggggcgcc aggacctcaa cgccagcggt    360
ctgtgcgtca actggaaccg ctactacaac gtctgccgca cgggcaacgc caaccctcac    420
aagggcgcca tcaactttga caacattggc tatgcctgga ttgtgatttt ccaggtgatc    480
actctggaag gctgggtgga gatcatgtac tatgtgatgg acgcacattc tttctacaac    540
ttcatctact catcctgct tatcata                                          567
```

<210> SEQ ID NO 22
<211> LENGTH: 189
<212> TYPE: PRT
<213> ORGANISM: rat
<220> FEATURE:
<223> OTHER INFORMATION: rat alpha-I partial sequence

<400> SEQUENCE: 22

```
Met Arg Ile Leu Val Asn Leu Leu Leu Asp Thr Leu Pro Met Leu Gly
  1               5                  10                  15

Asn Val Leu Leu Cys Phe Phe Val Phe Phe Ile Phe Gly Ile Ile
                 20                  25                  30

Gly Val Gln Leu Trp Ala Gly Leu Leu Arg Asn Arg Cys Phe Leu Glu
            35                  40                  45

Glu Asn Phe Thr Ile Gln Gly Asp Val Ala Leu Pro Pro Tyr Tyr Gln
         50                  55                  60

Pro Glu Glu Asp Asp Glu Met Pro Phe Ile Cys Ser Leu Thr Gly Asp
```

```
                65                  70                  75                  80
Asn Gly Ile Met Gly Cys His Glu Ile Pro Pro Leu Lys Glu Gln Gly
                85                  90                  95

Arg Glu Cys Cys Leu Ser Lys Asp Asp Val Tyr Asp Phe Gly Ala Gly
            100                 105                 110

Arg Gln Asp Leu Asn Ala Ser Gly Leu Cys Val Asn Trp Asn Arg Tyr
        115                 120                 125

Tyr Asn Val Cys Arg Thr Gly Asn Ala Asn Pro His Lys Gly Ala Ile
    130                 135                 140

Asn Phe Asp Asn Ile Gly Tyr Ala Trp Ile Val Ile Phe Gln Val Ile
145                 150                 155                 160

Thr Leu Glu Gly Trp Val Glu Ile Met Tyr Tyr Val Met Asp Ala His
                165                 170                 175

Ser Phe Tyr Asn Phe Ile Tyr Phe Ile Leu Leu Ile Ile
                180                 185

<210> SEQ ID NO 23
<211> LENGTH: 7540
<212> TYPE: DNA
<213> ORGANISM: rat

<400> SEQUENCE: 23
ccgtctctgg cgcggagcgg gacgatgctg acccccttaga tcctgctcca gctgcgccga        60
gggaagaggg ggcgcccctc cccggacccc cgccctccat cgggtggccc cttttttttc       120
tcttcctctc gggggctgct cgccgaagg tagcgcctgt tacgggcaac cggagcctgg       180
gcgcgaacga agaagccgga acaaagtgag gggaagccgc ccggctagtc ggggagcccc       240
cgggaaccca ggggaagcgg gactctacgc caggcggggc ttccctgaga cccggcgccc       300
cgcgggcagc atgccctgag ggcaggggga gctgagctga actggccctc ctggggactc       360
agcaagctct ctagagcccc ccacatgctc ccccaccggg tcccccgttg cgtgaggaca       420
cctcctctga gggctccgc tcgcccctct tcggaccccc cggggccccg gctggccaga       480
ggatggacga ggaggaggat ggagcgggcg ccgaggagtc gggacagccc cgtagcttca       540
cgcagctcaa cgacctgtcc ggggccgggg gcggcagggg ccgggtcgac ggaaaaggac       600
ccgggcagcg cggactccga gcggaggggg ctgccgtacc cggcgctagc cccgtggtt       660 ttcttctact tgagccagga cagccgcccg cggagctggt gtctccgcac ggtctgtaac       720
ccgtggttcg agcgagtcag tatgctggtc attcttctca actgtgtgac tctgggtatg       780
ttcaggccgt gtgaggacat tgcctgtgac tcccagcgct gccggatcct gcaggccttc       840
gatgacttca tctttgcctt ctttgctgtg gaaatggtgg tgaagatggt ggccttgggc       900
atctttggga gaaatgttta cctgggagac acttggaacc ggcttgactt tttcattgtc       960
attgcaggga tgctggagta ttcgctggac ctgcagaacg tcagcttctc cgcagtcagg      1020
acagtccgtg tgctgcgacc gctcagggcc attaaccggg tgcccagcat gcgcattctc      1080
gtcacattac tgctggacac cttgcctatg ctgggcaacg tcctgctgct ctgtttcttc      1140 gtcttttca tctttggcat cgtgggcgtc cagctgtggg caggactgct cgcaaccgg      1200 tgcttcctcc ccgagaactt cagcctcccc ctgagcgtgg acctggagcc ttattaccag      1260
acagagaatg aggacgagag ccccttcatc tgctctcagc ctcgggagaa tggcatgaga      1320
tcctgcagga gtgtgcccac actgcgtggg gaaggcggtg gtgggccacc ctgcagtctg      1380
gactatgaga cctataacag ttccagcaac accacctgtg tcaactggaa ccagtactat      1440
```

```
accaactgct ctgcgggcga gcacaacccc ttcaaaggcg ccatcaactt tgacaacatt    1500
ggctatgcct ggatcgccat cttccaggtc atcacactgg agggctgggt cgacatcatg    1560
tacttcgtaa tggacgctca ctccttctac aacttcatct acttcattct tctcatcatc    1620
gtgggctcct tcttcatgat caacctgtgc ctggtggtga ttgccacgca gttctccgag    1680
accaaacagc gggagagtca gctgatgcgg gagcagcgtg tacgattcct gtccaatgct    1740 agcacctgg caagcttctc tgagccaggc agctgctatg aggagctact caagtacctg    1800
gtgtacatcc tccgaaaagc agcccgaagg ctggcccagg tctctagggc tataggcgtg    1860
cgggctgggc tgctcagcag cccagtggcc cgtagtgggc aggagcccca gcccagtggc    1920
agctgcactc gctcacaccg tcgtctgtct gtccaccacc tggtccacca ccatcaccac    1980
caccatcacc actaccacct gggtaatggg acgctcagac ttccccgggc cagcccagag    2040
atccaggaca gggatgccaa tgggtctcgc cggctcatgc taccaccacc ctctacaccc    2100
actccctctg ggggccctcc gagggtgcg gagtctgtac acagcttcta ccatgctgac    2160
tgccacttgg agccagtccg ttgccaggca ccccctccca gatgcccatc ggaggcatct    2220
ggtaggactg tgggtagtgg gaaggtgtac cccactgtgc ataccagccc tccaccagag    2280
atactgaagg ataaagcact agtggaggtg gcccccagcc ctgggccccc caccctcacc    2340
agcttcaaca tcccacctgg gcccttcagc tccatgcaca agctcctgga cacacagagt    2400
acgggagcct gccatagctc ctgcaaaatc tccagcccct tgctccaaggc agacagtgga    2460 gcctgcgggc cggacagttg tccctactgt gcccggacag gagcaggaga gccagagtcc    2520
gctgaccatg tcatgcctga ctcagacagc gaggctgtgt atgagttcac acaggacgct    2580
cagcacagtg acctccggga tccccacagc cggcggcgac agcggagcct gggcccagat    2640
gcagagccta gttctgtgct ggctttctgg aggctgatct gtgacacatt ccggaagatc    2700
gtagatagca aatactttgg ccggggaatc atgatcgcca tcctggtcaa tacactcagc    2760
atgggcatcg agtaccacga gcagcccgag gagctcacca acgccctgga aatcagcaac    2820
atcgtcttca ccagcctctt cgccttggag atgctgctga actgcttgt ctacggtccc    2880 tttggctaca ttaagaatcc ctacaacatc tttgatggtg tcattgtggt catcagtgtg    2940
tgggagattg tgggccagca gggaggtggc ctgtcggtgc tgcggacctt ccgcctgatg    3000
cgggtgctga agctggtgcg cttcctgccg gccctgcagc gccagctcgt ggtgctcatg    3060
aagaccatgg acaacgtggc caccttctgc atgctcctca tgctgttcat cttcatcttc    3120
agcatcctgg gcatgcatct ctttggttgc aagttcgcat ctgaacggga tgggacacag    3180
ttgccagacc ggaagaattt cgactccctg ctctgggcca tcgtcactgt ctttcagatt    3240
ctgactcagg aagactggaa taaagtcctc tacaacggca tggcctccac atcgtcttgg    3300
gctgctcttt acttcatcgc cctcatgact tttggcaact atgtgctctt taacctgctg    3360
gtggccattc ttgtggaagg attccaggca gagggagatg ccaccaagtc tgagtcagag    3420
cctgatttct tttcgcccag tgtggatggt gatgggggaca gaaagaagcg cttggccctg    3480
gtggcttttg gagaacacgc ggaactacga aagagccttt tgccacccct catcatccat    3540
acggctgcga caccaatgtc acaccccaag agctccagca caggtgtggg ggaagcactg    3600
ggctctggct ctcgacgtac cagtagcagt gggtccgctg agcctggagc tgcccaccat    3660
gagatgaaat gtccgccaag tgcccgcagc tccccgcaca gtccctggag tgcggcaagc    3720
agctggacca gcaggcgctc cagcaggaac agcctgggcc gggcccccag cctaaagcgg    3780
aggagcccga gcggggagcg gaggtccctg ctgtctggag agggccagga gagtcaggat    3840
```

-continued

```
gaggaggaaa gttcagaaga ggaccgggcc agcccagcag gcagtgacca tcgccacagg      3900
ggttccttgg aacgtgaggc caagagttcc tttgacctgc ctgacactct gcaggtgccg      3960
gggctgcacc gcacagccag cggccggagc tctgcctctg agcaccaaga ctgtaatggc      4020
aagtcggctt cagggcgttt ggcccgcacc ctgaggactg atgaccccca actggatggg      4080
gatgatgaca atgatgaggg aaatctgagc aaaggggaac gcatacaagc ctgggtcaga      4140
tcccggcttc ctgcctgttg ccgagagcga gattcctggt cggcctatat ctttcctcct      4200
cagtcaaggt ttcgtctcct gtgtcaccgg atcatcaccc acaagatgtt tgaccatgtg      4260
gtcctcgtca tcatcttcct caactgtatc accatcgcta tggagcgccc caaaattgac      4320
ccccacagcg ctgagcgcat cttcctgacc ctctccaact acatcttcac ggcagtcttt      4380
ctagctgaaa tgacagtgaa ggtggtggca ctgggctggt gctttgggga gcaggcctac      4440
ctgcgcagca gctggaatgt gctggacggc ttgctggtgc tcatctccgt catcgacatc      4500
ctggtctcca tggtctccga cagcggcacc aagatccttg gcatgctgag ggtgctgcgg      4560
ctgctgcgga ccctgcgtcc actcagggtc atcagccggg cccagggact gaagctggtg      4620
gtagagactc tgatgtcatc cctcaaaccc attggcaaca ttgtggtcat ttgctgtgcc      4680
ttcttcatca tttttggaat tctcggggtg cagctcttca agggaagtt cttcgtgtgt       4740 cagggtgagg acaccaggaa catcactaac aaatccgact cgcgctgaggc cagctaccga     4800 tgggtccggc acaagtacaa ctttgacaac ctgggccagg ctctgatgtc cctgtttgtg      4860
ctggcctcca aggatggttg ggttgacatc atgtatgatg gctggatgc tgtgggtgtg       4920 gatcagcagc ccatcatgaa ccacaacccc tggatgctgc tatacttcat ctccttcctc      4980
ctcatcgtgg ccttctttgt cctgaacatg tttgtgggcg tggtggtgga aacttccat      5040 aagtgcagac agcaccagga ggaggaggag gcgaggcggc gtgaggagaa gcgactacgg      5100
aggctggaga aaaagagaag gagtaaggag aagcagatgg ccgaagccca gtgcaagccc      5160
tactactctg actactcgag attccggctc cttgtccacc acctgtgtac cagccactac      5220
ctggacctct tcatcactgg tgtcatcggg ctgaacgtgg tcactatggc catgaacat      5280 taccagcagc cccagatcct ggacgaggct ctgaagatct gcaattacat ctttaccgtc      5340
atctttgtct ttgagtcagt tttcaaactt gtggcctttg cgttccgccg tttcttccag      5400
gacaggtgga accagctgga cctggctatt gtgcttctgt ccatcatggg catcacactg      5460
gaggagattg aggtcaatct gtcgctgccc atcaacccca ccatcatccg tatcatgagg      5520
gtgctccgca ttgctcgagt tctgaagctg ttgaagatgg ctgtgggcat gcgggcactg      5580
ctgcacacgg tgatgcaggc cctgcccag gtggggaacc tgggacttct cttcatgtta      5640
ttgtttttca tctttgcagc tctgggcgtg agctcttgg agacctgga gtgtgatgag       5700 acacacccctt gtgagggctt gggtcggcat gccacctta ggaactttgg tatggccttt      5760
ctgaccctct tccgagtctc cactggtgac aactggaatg gtattatgaa ggacccttcc      5820
cgggactgtg accaggagtc cacctgctac aacactgtca tctcccctat ctactttgtg      5880
tccttcgtgc tgacggccca gtttgtgctg gtcaacgtgg tcatagctgt gctgatgaag      5940
cacctggaag aaagcaacaa agaggccaag gaggaggccg agctcgaggc cgagctggag      6000
ctggagatga agacgctcag cccgcagccc cactccccgc tgggcagccc cttcctctgg      6060 cccgggtg agggtgtcaa cagtactgac agccctaagc ctggggctcc acacaccact       6120
gcccacattg gagcagcctc gggcttctcc cttgagcacc ccacgatggt accccacccc      6180
```

-continued

```
gaggaggtgc cagtcccct aggaccagac ctgctgactg tgaggaagtc tggtgtcagc    6240
cggacgcact ctctgcccaa tgacagctac atgtgccgca atgggagcac tgctgagaga    6300
tccctaggac acaggggctg ggggctcccc aaagcccagt caggctccat cttgtccgtt    6360
cactcccaac cagcagacac cagctgcatc ctacagcttc ccaaagatgt gcactatctg    6420
ctccagcctc atggggctcc cacctggggc gccatcccta aactaccccc acctggccgc    6480
tcccctctgg ctcagaggcc tctcaggcgc caggcagcaa taaggactga ctccctggat    6540
gtgcagggcc tggtagccg ggaagacctg ttgtcagagg tgagtgggcc ctcctgccct    6600
ctgacccggt cctcatcctt ctggggcggg tcgagcatcc aggtgcagca gcgttccggc    6660
atccagagca aagtctccaa gcacatccgc ctgccagccc cttgcccagg cctggaaccc    6720
agctgggcca aggaccctcc agagaccaga agcagcttag agctggacac ggagctgagc    6780
tggatttcag gagacctcct tcccagcagc caggaagaac ccctgttccc acgggacctg    6840
aagaagtgct acagtgtaga gacccagagc tgcaggcgca ggcctgggtt ctggctagat    6900
gaacagcgga gacactccat tgctgtcagc tgtctggaca gcggctccca accccgccta    6960
tgtccaagcc cctcaagcct cggggccaa cctcttgggg gtcctgggag ccggcctaag    7020
aaaaaactca gcccacccag tatctctata gacccccgg agagccaggg ctctcggccc    7080
ccatgcagtc ctggtgtctg cctcaggagg agggcgccgg ccagtgactc taaggatccc    7140
tcggtctcca gccccttga cagcacggct gcctcaccct cccaaagaa agacacgctg    7200 agtctctctg gtttgtcttc tgacccaaca gacatggacc cctgagtcct acccactctc    7260
ccccatcacc tttctccacc gggtgcagat cctacgtccg cctcctgggc agcgtttctg    7320
aaaagtccca cgtaagcagc aagcagccac gaggcacctc acctgccttc ttcagtggct    7380
ggtggggatg acgagcagaa cttccggaga gtcgatctga agagaacaca gccctggagc    7440
ccctgcctcc gggaagaagg aaaaggagaa gcccagtgtg gccaaggctc ccgacaccag    7500
gagctgttgg gagaagcaat acgtttgtgc agaatctcta                           7540
```

<210> SEQ ID NO 24
<211> LENGTH: 2287
<212> TYPE: PRT
<213> ORGANISM: rat

<400> SEQUENCE: 24

```
Met Leu Pro His Arg Val Pro Arg Cys Val Arg Thr Pro Pro Leu Arg
  1               5                  10                  15

Gly Ser Ala Arg Pro Ser Asp Pro Gly Pro Arg Leu Ala Arg
             20                  25                  30

Gly Trp Thr Arg Arg Met Glu Arg Ala Pro Arg Ser Arg Asp Ser
         35                  40                  45

Pro Val Ala Ser Arg Ser Thr Thr Cys Pro Gly Pro Gly Ala Ala
     50                  55                  60

Gly Ala Gly Ser Thr Glu Lys Asp Pro Gly Ser Ala Asp Ser Glu Ala
 65                  70                  75                  80

Glu Gly Leu Pro Tyr Pro Ala Leu Ala Pro Val Phe Phe Tyr Leu
                 85                  90                  95

Ser Gln Asp Ser Pro Arg Ser Trp Cys Leu Arg Thr Val Cys Asn
            100                 105                 110

Pro Trp Phe Glu Arg Val Ser Met Leu Val Ile Leu Leu Asn Cys Val
            115                 120                 125

Thr Leu Gly Met Phe Arg Pro Cys Glu Asp Ile Ala Cys Asp Ser Gln
```

-continued

```
            130                 135                 140
Arg Cys Arg Ile Leu Gln Ala Phe Asp Asp Phe Ile Phe Ala Phe Phe
145                 150                 155                 160

Ala Val Glu Met Val Val Lys Met Val Ala Leu Gly Ile Phe Gly Lys
                165                 170                 175

Lys Cys Tyr Leu Gly Asp Thr Trp Asn Arg Leu Asp Phe Phe Ile Val
                180                 185                 190

Ile Ala Gly Met Leu Glu Tyr Ser Leu Asp Leu Gln Asn Val Ser Phe
                195                 200                 205

Ser Ala Val Arg Thr Val Arg Val Leu Arg Pro Leu Arg Ala Ile Asn
    210                 215                 220

Arg Val Pro Ser Met Arg Ile Leu Val Thr Leu Leu Leu Asp Thr Leu
225                 230                 235                 240

Pro Met Leu Gly Asn Val Leu Leu Leu Cys Phe Phe Val Phe Phe Ile
                245                 250                 255

Phe Gly Ile Val Gly Val Gln Leu Trp Ala Gly Leu Leu Arg Asn Arg
                260                 265                 270

Cys Phe Leu Pro Glu Asn Phe Ser Leu Pro Leu Ser Val Asp Leu Glu
    275                 280                 285

Pro Tyr Tyr Gln Thr Glu Asn Glu Asp Glu Ser Pro Phe Ile Cys Ser
    290                 295                 300

Gln Pro Arg Glu Asn Gly Met Arg Ser Cys Arg Ser Val Pro Thr Leu
305                 310                 315                 320

Arg Gly Glu Gly Gly Gly Pro Pro Cys Ser Leu Asp Tyr Glu Thr
                325                 330                 335

Tyr Asn Ser Ser Ser Asn Thr Thr Cys Val Asn Trp Asn Gln Tyr Tyr
                340                 345                 350

Thr Asn Cys Ser Ala Gly Glu His Asn Pro Phe Lys Gly Ala Ile Asn
                355                 360                 365

Phe Asp Asn Ile Gly Tyr Ala Trp Ile Ala Ile Phe Gln Val Ile Thr
    370                 375                 380

Leu Glu Gly Trp Val Asp Ile Met Tyr Phe Val Met Asp Ala His Ser
385                 390                 395                 400

Phe Tyr Asn Phe Ile Tyr Phe Ile Leu Leu Ile Ile Val Gly Ser Phe
                405                 410                 415

Phe Met Ile Asn Leu Cys Leu Val Val Ile Ala Thr Gln Phe Ser Glu
                420                 425                 430

Thr Lys Gln Arg Glu Ser Gln Leu Met Arg Glu Gln Arg Val Arg Phe
                435                 440                 445

Leu Ser Asn Ala Ser Thr Leu Ala Ser Phe Ser Glu Pro Gly Ser Cys
    450                 455                 460

Tyr Glu Glu Leu Leu Lys Tyr Leu Val Tyr Ile Leu Arg Lys Ala Ala
465                 470                 475                 480

Arg Arg Leu Ala Gln Val Ser Arg Ala Ile Gly Val Arg Ala Gly Leu
                485                 490                 495

Leu Ser Ser Pro Val Ala Arg Ser Gly Gln Glu Pro Gln Pro Ser Gly
                500                 505                 510

Ser Cys Thr Arg Ser His Arg Arg Leu Ser Val His His Leu Val His
                515                 520                 525

His His His His His His His Tyr His Leu Gly Asn Gly Thr Leu
    530                 535                 540

Arg Val Pro Arg Ala Ser Pro Glu Ile Gln Asp Arg Asp Ala Asn Gly
545                 550                 555                 560
```

-continued

```
Ser Arg Arg Leu Met Leu Pro Pro Ser Thr Pro Thr Pro Ser Gly
            565                 570                 575

Gly Pro Pro Arg Gly Ala Glu Ser Val His Ser Phe Tyr His Ala Asp
            580                 585                 590

Cys His Leu Glu Pro Val Arg Cys Gln Ala Pro Pro Arg Cys Pro
            595                 600             605

Ser Glu Ala Ser Gly Arg Thr Val Gly Ser Gly Lys Val Tyr Pro Thr
    610                 615                 620

Val His Thr Ser Pro Pro Glu Ile Leu Lys Asp Lys Ala Leu Val
625                 630                 635                 640

Glu Val Ala Pro Ser Pro Gly Pro Pro Thr Leu Thr Ser Phe Asn Ile
                645                 650                 655

Pro Pro Gly Pro Phe Ser Ser Met His Lys Leu Leu Glu Thr Gln Ser
            660                 665                 670

Thr Gly Ala Cys His Ser Ser Cys Lys Ile Ser Ser Pro Cys Ser Lys
            675                 680                 685

Ala Asp Ser Gly Ala Cys Gly Pro Asp Ser Cys Pro Tyr Cys Ala Arg
690                 695                 700

Thr Gly Ala Gly Glu Pro Glu Ser Ala Asp His Val Met Pro Asp Ser
705                 710                 715                 720

Asp Ser Glu Ala Val Tyr Glu Phe Thr Gln Asp Ala Gln His Ser Asp
                725                 730                 735

Leu Arg Asp Pro His Ser Arg Arg Gln Arg Ser Leu Gly Pro Asp
            740                 745                 750

Ala Glu Pro Ser Ser Val Leu Ala Phe Trp Arg Leu Ile Cys Asp Thr
            755                 760                 765

Phe Arg Lys Ile Val Asp Ser Lys Tyr Phe Gly Arg Gly Ile Met Ile
            770                 775                 780

Ala Ile Leu Val Asn Thr Leu Ser Met Gly Ile Glu Tyr His Glu Gln
785                 790                 795                 800

Pro Glu Glu Leu Thr Asn Ala Leu Glu Ile Ser Asn Ile Val Phe Thr
                805                 810                 815

Ser Leu Phe Ala Leu Glu Met Leu Leu Lys Leu Leu Val Tyr Gly Pro
            820                 825                 830

Phe Gly Tyr Ile Lys Asn Pro Tyr Asn Ile Phe Asp Gly Val Ile Val
            835                 840                 845

Val Ile Ser Val Trp Glu Ile Val Gly Gln Gln Gly Gly Gly Leu Ser
850                 855                 860

Val Leu Arg Thr Phe Arg Leu Met Arg Val Leu Lys Leu Val Arg Phe
865                 870                 875                 880

Leu Pro Ala Leu Gln Arg Gln Leu Val Val Leu Met Lys Thr Met Asp
                885                 890                 895

Asn Val Ala Thr Phe Cys Met Leu Leu Met Leu Phe Ile Phe Ile Phe
                900                 905                 910

Ser Ile Leu Gly Met His Leu Phe Gly Cys Lys Phe Ala Ser Glu Arg
            915                 920                 925

Asp Gly Asp Thr Leu Pro Asp Arg Lys Asn Phe Asp Ser Leu Leu Trp
    930                 935                 940

Ala Ile Val Thr Val Phe Gln Ile Leu Thr Gln Glu Asp Trp Asn Lys
945                 950                 955                 960

Val Leu Tyr Asn Gly Met Ala Ser Thr Ser Ser Trp Ala Ala Leu Tyr
                965                 970                 975
```

```
Phe Ile Ala Leu Met Thr Phe Gly Asn Tyr Val Leu Phe Asn Leu Leu
            980                 985                 990

Val Ala Ile Leu Val Glu Gly Phe Gln Ala Glu Gly Asp Ala Thr Lys
        995                 1000                1005

Ser Glu Ser Glu Pro Asp Phe Ser Pro Ser Val Asp Gly Asp Gly
    1010                1015                1020

Asp Arg Lys Lys Arg Leu Ala Leu Val Ala Leu Gly Glu His Ala Glu
1025                1030                1035                1040

Leu Arg Lys Ser Leu Leu Pro Pro Leu Ile Ile His Thr Ala Ala Thr
            1045                1050                1055

Pro Met Ser His Pro Lys Ser Ser Thr Gly Val Gly Glu Ala Leu
        1060                1065                1070

Gly Ser Gly Ser Arg Arg Thr Ser Ser Gly Ser Ala Glu Pro Gly
    1075                1080                1085

Ala Ala His His Glu Met Lys Cys Pro Pro Ser Ala Arg Ser Ser Pro
1090                1095                1100

His Ser Pro Trp Ser Ala Ala Ser Ser Trp Thr Ser Arg Arg Ser Ser
1105                1110                1115                1120

Arg Asn Ser Leu Gly Arg Ala Pro Ser Leu Lys Arg Ser Pro Ser
        1125                1130                1135

Gly Glu Arg Arg Ser Leu Leu Ser Gly Glu Gly Gln Glu Ser Gln Asp
            1140                1145                1150

Glu Glu Glu Ser Ser Glu Glu Asp Arg Ala Ser Pro Ala Gly Ser Asp
        1155                1160                1165

His Arg His Arg Gly Ser Leu Glu Arg Glu Ala Lys Ser Ser Phe Asp
1170                1175                1180

Leu Pro Asp Thr Leu Gln Val Pro Gly Leu His Arg Thr Ala Ser Gly
1185                1190                1195                1200

Arg Ser Ser Ala Ser Glu His Gln Asp Cys Asn Gly Lys Ser Ala Ser
            1205                1210                1215

Gly Arg Leu Ala Arg Thr Leu Arg Thr Asp Asp Pro Gln Leu Asp Gly
        1220                1225                1230

Asp Asp Asp Asn Asp Glu Gly Asn Leu Ser Lys Gly Glu Arg Ile Gln
    1235                1240                1245

Ala Trp Val Arg Ser Arg Leu Pro Ala Cys Cys Arg Glu Arg Asp Ser
    1250                1255                1260

Trp Ser Ala Tyr Ile Phe Pro Pro Gln Ser Arg Phe Arg Leu Leu Cys
1265                1270                1275                1280

His Arg Ile Ile Thr His Lys Met Phe Asp His Val Val Leu Val Ile
            1285                1290                1295

Ile Phe Leu Asn Cys Ile Thr Ile Ala Met Glu Arg Pro Lys Ile Asp
            1300                1305                1310

Pro His Ser Ala Glu Arg Ile Phe Leu Thr Leu Ser Asn Tyr Ile Phe
        1315                1320                1325

Thr Ala Val Phe Leu Ala Glu Met Thr Val Lys Val Val Ala Leu Gly
    1330                1335                1340

Trp Cys Phe Gly Glu Gln Ala Tyr Leu Arg Ser Ser Trp Asn Val Leu
1345                1350                1355                1360

Asp Gly Leu Leu Val Leu Ile Ser Val Ile Asp Ile Leu Val Ser Met
            1365                1370                1375

Val Ser Asp Ser Gly Thr Lys Ile Leu Gly Met Leu Arg Val Leu Arg
        1380                1385                1390

Leu Leu Arg Thr Leu Arg Pro Leu Arg Val Ile Ser Arg Ala Gln Gly
```

-continued

```
            1395                1400                1405
Leu Lys Leu Val Val Glu Thr Leu Met Ser Ser Leu Lys Pro Ile Gly
    1410                1415                1420

Asn Ile Val Val Ile Cys Cys Ala Phe Phe Ile Ile Phe Gly Ile Leu
1425                1430                1435                1440

Gly Val Gln Leu Phe Lys Gly Lys Phe Phe Val Cys Gln Gly Glu Asp
            1445                1450                1455

Thr Arg Asn Ile Thr Asn Lys Ser Asp Cys Ala Glu Ala Ser Tyr Arg
        1460                1465                1470

Trp Val Arg His Lys Tyr Asn Phe Asp Asn Leu Gly Gln Ala Leu Met
    1475                1480                1485

Ser Leu Phe Val Leu Ala Ser Lys Asp Gly Trp Val Asp Ile Met Tyr
    1490                1495                1500

Asp Gly Leu Asp Ala Val Gly Val Asp Gln Gln Pro Ile Met Asn His
1505                1510                1515                1520

Asn Pro Trp Met Leu Leu Tyr Phe Ile Ser Phe Leu Leu Ile Val Ala
            1525                1530                1535

Phe Phe Val Leu Asn Met Phe Val Gly Val Val Glu Asn Phe His
        1540                1545                1550

Lys Cys Arg Gln His Gln Glu Glu Glu Ala Arg Arg Arg Glu Glu
    1555                1560                1565

Lys Arg Leu Arg Arg Leu Glu Lys Lys Arg Arg Ser Lys Glu Lys Gln
    1570                1575                1580

Met Ala Glu Ala Gln Cys Lys Pro Tyr Tyr Ser Asp Tyr Ser Arg Phe
1585                1590                1595                1600

Arg Leu Leu Val His His Leu Cys Thr Ser His Tyr Leu Asp Leu Phe
            1605                1610                1615

Ile Thr Gly Val Ile Gly Leu Asn Val Val Thr Met Ala Met Glu His
        1620                1625                1630

Tyr Gln Gln Pro Gln Ile Leu Asp Glu Ala Leu Lys Ile Cys Asn Tyr
    1635                1640                1645

Ile Phe Thr Val Ile Phe Val Phe Glu Ser Val Phe Lys Leu Val Ala
    1650                1655                1660

Phe Ala Phe Arg Arg Phe Phe Gln Asp Arg Trp Asn Gln Leu Asp Leu
1665                1670                1675                1680

Ala Ile Val Leu Leu Ser Ile Met Gly Ile Thr Leu Glu Glu Ile Glu
            1685                1690                1695

Val Asn Leu Ser Leu Pro Ile Asn Pro Thr Ile Ile Arg Ile Met Arg
        1700                1705                1710

Val Leu Arg Ile Ala Arg Val Leu Lys Leu Leu Lys Met Ala Val Gly
    1715                1720                1725

Met Arg Ala Leu Leu His Thr Val Met Gln Ala Leu Pro Gln Val Gly
    1730                1735                1740

Asn Leu Gly Leu Leu Phe Met Leu Leu Phe Phe Ile Phe Ala Ala Leu
1745                1750                1755                1760

Gly Val Glu Leu Phe Gly Asp Leu Glu Cys Asp Glu Thr His Pro Cys
            1765                1770                1775

Glu Gly Leu Gly Arg His Ala Thr Phe Arg Asn Phe Gly Met Ala Phe
        1780                1785                1790

Leu Thr Leu Phe Arg Val Ser Thr Gly Asp Asn Trp Asn Gly Ile Met
    1795                1800                1805

Lys Asp Pro Ser Arg Asp Cys Asp Gln Glu Ser Thr Cys Tyr Asn Thr
    1810                1815                1820
```

```
Val Ile Ser Pro Ile Tyr Phe Val Ser Phe Val Leu Thr Ala Gln Phe
1825                1830                1835                1840

Val Leu Val Asn Val Val Ile Ala Val Leu Met Lys His Leu Glu Glu
                1845                1850                1855

Ser Asn Lys Glu Ala Lys Glu Glu Ala Glu Leu Glu Ala Glu Leu Glu
            1860                1865                1870

Leu Glu Met Lys Thr Leu Ser Pro Gln Pro His Ser Pro Leu Gly Ser
        1875                1880                1885

Pro Phe Leu Trp Pro Gly Val Glu Gly Val Asn Ser Thr Asp Ser Pro
    1890                1895                1900

Lys Pro Gly Ala Pro His Thr Thr Ala His Ile Gly Ala Ala Ser Gly
1905                1910                1915                1920

Phe Ser Leu Glu His Pro Thr Met Val Pro His Pro Glu Glu Val Pro
                1925                1930                1935

Val Pro Leu Gly Pro Asp Leu Leu Thr Val Arg Lys Ser Gly Val Ser
            1940                1945                1950

Arg Thr His Ser Leu Pro Asn Asp Ser Tyr Met Cys Arg Asn Gly Ser
        1955                1960                1965

Thr Ala Glu Arg Ser Leu Gly His Arg Gly Trp Gly Leu Pro Lys Ala
   1970                1975                1980

Gln Ser Gly Ser Ile Leu Ser Val His Ser Gln Pro Ala Asp Thr Ser
1985                1990                1995                2000

Cys Ile Leu Gln Leu Pro Lys Asp Val His Tyr Leu Leu Gln Pro His
                2005                2010                2015

Gly Ala Pro Thr Trp Gly Ala Ile Pro Lys Leu Pro Pro Pro Gly Arg
            2020                2025                2030

Ser Pro Leu Ala Gln Arg Pro Leu Arg Arg Gln Ala Ala Ile Arg Thr
        2035                2040                2045

Asp Ser Leu Asp Val Gln Gly Leu Gly Ser Arg Glu Asp Leu Leu Ser
    2050                2055                2060

Glu Val Ser Gly Pro Ser Cys Pro Leu Thr Arg Ser Ser Ser Phe Trp
2065                2070                2075                2080

Gly Gly Ser Ser Ile Gln Val Gln Gln Arg Ser Gly Ile Gln Ser Lys
                2085                2090                2095

Val Ser Lys His Ile Arg Leu Pro Ala Pro Cys Pro Gly Leu Glu Pro
            2100                2105                2110

Ser Trp Ala Lys Asp Pro Pro Glu Thr Arg Ser Ser Leu Glu Leu Asp
        2115                2120                2125

Thr Glu Leu Ser Trp Ile Ser Gly Asp Leu Leu Pro Ser Ser Gln Glu
    2130                2135                2140

Glu Pro Leu Phe Pro Arg Asp Leu Lys Lys Cys Tyr Ser Val Glu Thr
2145                2150                2155                2160

Gln Ser Cys Arg Arg Arg Pro Gly Phe Trp Leu Asp Glu Gln Arg Arg
                2165                2170                2175

His Ser Ile Ala Val Ser Cys Leu Asp Ser Gly Ser Gln Pro Arg Leu
            2180                2185                2190

Cys Pro Ser Pro Ser Ser Leu Gly Gly Gln Pro Leu Gly Gly Pro Gly
        2195                2200                2205

Ser Arg Pro Lys Lys Lys Leu Ser Pro Pro Ser Ile Ser Ile Asp Pro
    2210                2215                2220

Pro Glu Ser Gln Gly Ser Arg Pro Pro Cys Ser Pro Gly Val Cys Leu
2225                2230                2235                2240
```

```
Arg Arg Arg Ala Pro Ala Ser Asp Ser Lys Asp Pro Ser Val Ser Ser
            2245                2250                2255
Pro Leu Asp Ser Thr Ala Ala Ser Pro Ser Pro Lys Lys Asp Thr Leu
            2260                2265                2270
Ser Leu Ser Gly Leu Ser Ser Asp Pro Thr Asp Met Asp Pro Glx
        2275                2280                2285

<210> SEQ ID NO 25
<211> LENGTH: 8447
<212> TYPE: DNA
<213> ORGANISM: rat

<400> SEQUENCE: 25
cgggataatt ctgtctcatt accataggca cacaataaaa catctttacc atttctctaa      60
actcagccat tggccaaagc cagaaggaag acctgtgcat ttgcatctgg ggatccgatc     120
ctgactgatg ctctaggttg ctgcgtatac agtggaggag actgtgagaa aggaccatag     180
tagtcaagga agaaagcatc ctgggacaga gccacaatca cgagatgatt cctaccaatg     240
aacctcttcg gactgggtcc cagtgacagc gccgccgggg ctatgccacg ggacgccgc      300
tagccaccgg agcgaggtga gatgcggagg gtacgcgcgc ttactgcgcg cctgggaccc     360
tttgaacttg agctctgtgg gctccgagcc cctagggctc ccgcaaccct tcgcctcggc     420
cttggggtg gggctgccag gctttgccgg cgggaggggg cggggggcgc atttgtctct     480
aataaggaga gacaaagaca tcccggcggc cgcggctgtt cccgcagctc cgctccgcct     540
gaggcgggc ggggggcgtcg ttcctgggcc agggtcacct cctgccctct ctccgcaggt     600
gctgccctcc gccaccatga ccagggcac gctggcagcg acgaagtcc gggtgcccct     660
gggcgcttcg ccgccggccc ctgcagcgcc ggtgagagct tccccagcga gccctggggc     720
gccggggcgc gaggagcagg gaggatccgg gtcgggagtg ttggctcccg agagcccagg     780
gaccgagtgt ggtgcggacc tgggcgccga cgaggaacag ccggtcccat acccagctct     840
ggctgccaca gtcttcttct gcctcgggca accacgcgg ccgcgcagct ggtgcctccg     900
actggtttgt aaacccgtggt tcgagcacgt cagcatgctg gtcatcatgc tgaactgcgt     960
gacactgggc atgttcaggc cctgtgagga tgttgagtgc cgctccgaac gttgcagcat    1020
cttggaggcc ttcgacgact tcatctttgc cttcttcgcc gtggagatgg tgatcaagat    1080
ggtggctttg gggctgtttg gcaaaaatg ctacctgggt gacacctgga caggctgga     1140
cttcttcatt gtcatggcgg gcatgatgga gtactctctg gacggacaca aggtgagcct    1200
ctctgccatc cgaaccgtgc gtgtgctgcg gcccctccgc gccatcaacc gagtccccag    1260
tatgcggatc ctggtcactc tgctgctgga cacgctgccc atgcttggga atgtcctcct    1320
cctctgcttc ttcgtcttct tcatcttcgg cattgttggg gtccagctct gggctggcct    1380
gcttcggaac cgatgcttcc tggacagcgc cttcgtcagg aacaacaacc tgaccttctt    1440
gcggccatac taccagacgg aggagggtga ggagaaccct ttcatctgct cctcccgccg    1500
tgacaacgtc atgcagaagt gctcgcacat ccccagccgc cgtgagcttc gagtgcagtg    1560
cacactcggc tgggaggcct atgggcagcc acaggctgag gatgggggtg ctggccgcaa    1620
cgcctgtatc aactgaacc agtattacaa cgtgtgccgc tcgggggaat caaccctca    1680
caacggtgcc atcaacttcg acaacattgg ctacgcttgg attgccatct tccaggtcat    1740
cacactggag ggctggtgg acatcatgta ctacgtcatg gatgcccact cgttctacaa    1800
cttcatctac ttcatcctcc tcatcattat gggctccttc ttcatgatca acctgtgcct    1860
```

-continued

| | | |
|---|---|---|
| ggtggtgata gccacacagt tctcagagac aaagcaaagg gaaaaccagc tgatgcgaga | 1920 | |
| acagcgggcc cgctatctgt ccaacgacag cactctggcc agcttctcag agcccggcag | 1980 | |
| ctgctacgag gagctcctca agtatgtagg ccacatcttc cggaaggtta aacgccgtag | 2040 | |
| cctgcgtctt tatgcccgct ggcagagccg ctggcgtaag aaggtggatc ccagcagtac | 2100 | |
| cgtgcatggc caaggccctg gcggcggcc acgacgggca ggcaggcgta cagcttcagt | 2160 | |
| gcaccatctg gtctaccacc accaccacca ccatcaccac cattaccact ttagccacgg | 2220 | |
| tggcccacgc aggcccagcc cagagccagg tgctggtgac aacaggttgg tcagggcctg | 2280 | |
| tgcgccaccc tcgccgccat ccccaggcca tgggccacca gactctgagt ctgtgcacag | 2340 | |
| tatctaccat gctgactgcc acgtggaggg gccgcaggaa cgagcccgag tggcacactc | 2400 | |
| catagccact gctgctagcc tcaagctggc ctcaggtttg ggtaccatga actaccccac | 2460 | |
| catcctacct tcaggaacag tcaacagcaa aggtggcacc agctcacgac ccaaggggct | 2520 | |
| acgaggtgct ggcgccccag gggctgcagt acacagccct ctgagcctgg gaagcccag | 2580 | |
| accctatgag aagatccagg atgtggtggg agaacaagga ctaggccgag cctctagcca | 2640 | |
| cctgtcaggc ctgagtgtgc cttgccccct gcccagcccc caggctggca cgctgacctg | 2700 | |
| tgagctgaag agctgcccat attgtgccag cgccctggag gaccccgagt ttgaattcag | 2760 | |
| tggctcagag agcggggact cggatgccca cggagtctat gagtttaccc aggatgtacg | 2820 | |
| gcatggggat tgtcgggacc ctgtgcagca gccccatgaa gtgggcacac caggccacag | 2880 | |
| caatgagcgg cggcggacac cactgcggaa ggcctcacaa ccaggaggga taggccacct | 2940 | |
| ctgggcatcc ttcagtggca agctacgtcg cattgtagac agcaagtact caaccgagg | 3000 | |
| catcatggca gccatcctcg tcaatactct gagcatgggc gttgagtatc atgaacagcc | 3060 | |
| tgaggagctg accaacgccc tggagataag caacatcgtg ttcaccagca tgtttgcctt | 3120 | |
| ggagatgcta ctgaagctgc tggcctgcgg cccactggga tacatccgga cccctacaa | 3180 | |
| catcttcgat ggcattgttg tcgtcataag tgtctgggag atcgtggggc aggcagacgg | 3240 | |
| tggccagtct gtgctgcgca ccttcaggct gctgcgggtg ctgaagctgg tgcgcttcct | 3300 | |
| gccggccctg cggcgccagc tcgtggtgct catgaggacc atggacaacg tggccacctt | 3360 | |
| ctgcatgctc ctcatgctgt tcatcttcat cttcagcatc ctgggcatgc acctgttcgg | 3420 | |
| ctgtaagttc agcctgaaga cagactctgg agacaccgtc cctgacagga gaacttcga | 3480 | |
| ctccctactg tgggccatcg tcaccgtgtt tcagatcttg acacaggaag actggaacgt | 3540 | |
| ggttctgtac aacggcatgg cctccacttc gtcctgggcc gcccttact ttgtggccct | 3600 | |
| catgaccttt gggaactatg tgctcttcaa cctgctggta gccatcctgg tggaaggttt | 3660 | |
| ccaggcagag ggtgacgcca ccagatctga caccgacgag gataagacgt ctacccagct | 3720 | |
| agagggagat ttcgataagc tcagagatct tcgagccaca gagatgaaga tgtattcact | 3780 | |
| ggcagtgacc cctaacgggc acctagaggg ccgaggcagc ctgccgccgc ccctcatcac | 3840 | |
| tcacacggca gctacgccta tgcctactcc caaaagctcc ccaaacctgg acgtggccca | 3900 | |
| tgctctcctg gactctcggc gcagcagcag cggctctgtg gaccccagc tggggaccca | 3960 | |
| gaagtctctg gccagcctcc gcagctcccc ttgcacccca tggggcccca acagcgctgg | 4020 | |
| gagcagcagg cgctccagtt ggaacagcct gggccgcgca cccagcctca acgccgcag | 4080 | |
| ccagtgtggg gagcgcgagt ccctgctctc tggagagggg aagggcagca ccgatgacga | 4140 | |
| ggccgaggac agcagaccaa gcacgggaac ccacccaggg gcctcgccag gccccgagc | 4200 | |
| cacgccactg cggcgtgccg agtcattgga ccaccgcagc acgctggacc tgtgtccacc | 4260 | |

```
acggcctgcg cctcctgccg tccaagttca tgactgcaac gggcagatgg tggccctgcc   4320
cagcgagttc tttctgcgca tcgacagcca caaggaggat gcagcggagt tgatgatga    4380
catagaggat agctgctgct ccgtctaca caaagtgctg aaccctatg caccccagtg     4440
gtgccgtagc cgggagtcct gggccctgta tctcttccca ccgcagaaca ggctacgcgt   4500
ctcctgccag aaagtcatcg cacacaagat gtttgaccac gtggtccttg tcttcatctt   4560
cctcaactgt atcaccattg ctctggagag ccagacatt gacccaggca gcactgagcg    4620
ggccttcctc agcgtctcca actacatctt cacagccatc ttcgtggtgg agatgatggt   4680
gaaggtggta gccctgggac tgctgtgggg tgaacatgcc tacctacaga gcagttggaa   4740
tgtgctggac gggctgcttg tcctggtatc cctggttgac atcatcgtgg ccatggcctc   4800
agctggcggt gccaagatcc taggcgtcct gcgtgtcgtg cgcctgctgc ggaccctgag   4860
gcctctgagg gtcatcagcc gagctccagg cctcaagctg gttgtagaga ctctgatatc   4920
atcgctcagg cccattggga acatcgtcct catctgctgc gccttcttca tcatctttgg   4980
catcctcggg gtgcagcttt tcaagggcaa attctactac tgcgagggca cagataccag   5040
gaatatcacc accaaggccg agtgccatgc tgcccactac cgctgggtga ggcgcaaata   5100
caactttgac aacctgggtc aggcgctgat gtctctgttc gtgctgtcat ctaaggatgg   5160
ctgggtaaac atcatgtatg acgggctgga tgccgtgggc atcgaccagc agcccgtgca   5220
gaaccacaac ccctgatgc tgctctactt catctccttc ctgctcatcg tcagcttctt    5280
cgtgctcaac atgtttgtgg gcgtggtggt ggagaacttc cacaagtgcc ggcagcacca   5340
ggaggctgag gaggctcggc gccgggagga gaaacggctg cggcgcctgg agaggaggcg   5400
caggaaggcc cagcgccggc cctactacgc agactattca cacactcgcc gctccatcca   5460
ttcgctgtgc accagccact acctggacct cttcatcacc ttcatcatct gcctcaatgt   5520
catcaccatg tccatggagc actacaacca gcccaagtcc ctggatgagg ccctcaagta   5580
ctgcaactac gtcttttacca tcgtcttcgt ctttgaggct gcactgaagc tggtggcctt   5640
tgggttccgg aggttcttca aggacaggtg gaaccagctg gacttggcca tcgtcctcct   5700
atccatcatg ggcattgcgc tggaggagat tgagatgaac gccgccctgc ccatcaatcc   5760
caccatcatc cgcatcatgc gtgtgcttcg aatcgcccgt gtgctgaagc tactgaagat   5820
ggccacaggc atgcgcgcct gctggatac tgtggttcaa gctctgcctc aggtagggaa    5880
ccttggtctt cttttcatgc tcctgttttt tatctatgct gccctgggag tggagctgtt   5940
tgggaggcta gagtgcagcg aggataaccc ctgcgagggc ctgagcaggc acgctacctt   6000
caccaacttc ggcatggcct tcctcacact gttccgagtg tccactgggg acaactggaa   6060
tgggattatg aaggataccc tccgtgagtg tacccgtgag acaagcact gcctcagcta    6120
cctgcccgcg ctctcacccg tctacttcgt caccttcatg ctggtggctc agttcgtgct   6180
ggtcaatgtg gtggtggccg tgctcatgaa gcacctggag gagagcaaca aggaggcccg   6240
cgaggatgca gagatggacg ccgagatcga gctggagatg gcacagggt ccacagccca    6300
gccccccacct acagcacagg aaagccaagg tacccagcca gacaccccga acctcctggt   6360
cgtgcgaaaa gtatctgtgt ccaggatgct ctcgctgccc aatgacagct acatgttcag   6420
gccggtggct cccgcggctg ccccacattc ccacccactg caggaagtgg agatggagac   6480
ctacacaggc ccggtcacct ctgctcactc gccacccctg gagccccgcg cctctttcca   6540
ggtcccatca gccgcgtcct ccccagccag ggtcagtgac cccccttgtg cccttcacc    6600
```

```
ccggggtaca ccccgctctc tgagtctctc acggatactc tgcagacagg aggccatgca    6660
ctctgagtcc ctggaaggga aggttgatga tgttggagga gacagcatcc agactacac     6720
agagcctgct gaaatatgt ccacgagcca ggcatcaaca ggtgccccga ggtcccctcc     6780
gtgctccccg cgacctgcca gcgtccgtac ccgcaagcac acgtttgggc aacgctgcat    6840
ctccagccgc cctcccaccc tgggaggaga tgaggctgaa gcagcagacc cagcagatga    6900
ggaggtcagc cacatcacca gctcagccca ccctggccg gctacagagc ccacagccc      6960
tgaggcctcc ccaacagcct ctcctgtgaa aggcacaatg ggcagtgggc gggacccacg    7020
caggttctgc agtgtagatg ctcagagctt cctggacaaa ccaggtcggc cagatgcaca    7080
acggtggtcc tcagtggaac tggataacgg agaaagccac ctagagtccg gggaagtgag    7140
gggccgggcc tcagagctcg aaccagctct tgggtcacga aggaagaaga agatgagccc    7200
tccctgcatc tccattgaac ctcccactaa ggatgagggc tcttcccggc ccctgcagc     7260
cgaaggaggc aacactaccc tgaggcgccg aacccatcc tgtgaggctg ccctccatag     7320
ggactgccca gagcctacag aaggcccagg caccggaggg gaccctgtag ccaagggtga    7380
gcgctggggc caggcctctt gccgagcaga gcatctgact gtccccaact ttgcctttga    7440
gcctctggac atgggcggac ctggtggaga ctgtttcttg gacagtgacc aaagtgtgac    7500
cccagaaccc agagtttcct cttttggggc tatagtgcct ctgatactag aaactgaact    7560
ttctatgccc tctcctgact gcccagagaa ggaacaagga ctgtacctca ctgtgcccca    7620
gacccccttg aagaaaccag ggtctacccc agccactcct gccccagatg acagtggaga    7680
tgagcctgtg tagatggggc tgcgtgtcca cagggctttg gcattgaggt tgttggctcc    7740
tgcagggtgg tagggccatg agtggaccct gcttaggccc cactaaggca gagggaccgg    7800
gagataacca tcccaggaga ggcagcagac atcccgtctc tgcaccatga cacaggagca    7860
gcctcgggcc ccacgagcct ccctcgtggt gattcaggtt tgggttttcc tgagttttaa    7920
ccaccaccag aagctgtacc aggaccaggt catcagtctc aggaggagag gctgtgtcct    7980
gggaaggacc agtaattcct cacaggcacc acagctccat ccatgtgaca cacaggtttc    8040
cgacagggag tacagcttga gcctgtgtac attgggtcct gcagccaccg cacccaatat    8100
caccttcgtt cacagtcctg tttctgtcca ccactcggca tccttccctc tcacagtgcc    8160
cctcccccat tccatcccct tagatggtct agaactttgc agtgaccctg ggaagtactg    8220
acccatgcaa taagacattg cagtcccaac tgaggtgggg cttcccatcc attccaggct    8280
gttgggctca acattcattt gacatccatt tgctttatgt catccgtttc tacaaattca    8340
ggttaaatgt tgcaataatc tgatgcagaa aacttggctt cctaagtcaa agctgagggg    8400
aggggagggg aggggcaagg caaatctgaa taaacactaa cttattg                  8447
```

<210> SEQ ID NO 26
<211> LENGTH: 2359
<212> TYPE: PRT
<213> ORGANISM: rat

<400> SEQUENCE: 26

Met Thr Glu Gly Thr Leu Ala Ala Asp Glu Val Arg Val Pro Leu Gly
1               5                   10                  15

Ala Ser Pro Pro Ala Pro Ala Ala Pro Val Arg Ala Ser Pro Ala Ser
            20                  25                  30

Pro Gly Ala Pro Gly Arg Glu Glu Gln Gly Gly Ser Gly Ser Gly Val
        35                  40                  45

```
Leu Ala Pro Glu Ser Pro Gly Thr Glu Cys Gly Ala Asp Leu Gly Ala
    50                  55                  60

Asp Glu Glu Gln Pro Val Pro Tyr Pro Ala Leu Ala Ala Thr Val Phe
65                  70                  75                  80

Phe Cys Leu Gly Gln Thr Thr Arg Pro Arg Ser Trp Cys Leu Arg Leu
                85                  90                  95

Val Cys Asn Pro Trp Phe Glu His Val Ser Met Leu Val Ile Met Leu
            100                 105                 110

Asn Cys Val Thr Leu Gly Met Phe Arg Pro Cys Glu Asp Val Glu Cys
            115                 120                 125

Arg Ser Glu Arg Cys Ser Ile Leu Glu Ala Phe Asp Asp Phe Ile Phe
    130                 135                 140

Ala Phe Phe Ala Val Glu Met Val Ile Lys Met Val Ala Leu Gly Leu
145                 150                 155                 160

Phe Gly Gln Lys Cys Tyr Leu Gly Asp Thr Trp Asn Arg Leu Asp Phe
                165                 170                 175

Phe Ile Val Met Ala Gly Met Met Glu Tyr Ser Leu Asp Gly His Lys
                180                 185                 190

Val Ser Leu Ser Ala Ile Arg Thr Val Arg Val Leu Arg Pro Leu Arg
            195                 200                 205

Ala Ile Asn Arg Val Pro Ser Met Arg Ile Leu Val Thr Leu Leu Leu
    210                 215                 220

Asp Thr Leu Pro Met Leu Gly Asn Val Leu Leu Leu Cys Phe Phe Val
225                 230                 235                 240

Phe Phe Ile Phe Gly Ile Val Gly Val Gln Leu Trp Ala Gly Leu Leu
                245                 250                 255

Arg Asn Arg Cys Phe Leu Asp Ser Ala Phe Val Arg Asn Asn Asn Leu
                260                 265                 270

Thr Phe Leu Arg Pro Tyr Tyr Gln Thr Glu Glu Gly Glu Glu Asn Pro
    275                 280                 285

Phe Ile Cys Ser Ser Arg Arg Asp Asn Gly Met Gln Lys Cys Ser His
    290                 295                 300

Ile Pro Ser Arg Arg Glu Leu Arg Val Gln Cys Thr Leu Gly Trp Glu
305                 310                 315                 320

Ala Tyr Gly Gln Pro Gln Ala Glu Asp Gly Gly Ala Gly Arg Asn Ala
                325                 330                 335

Cys Ile Asn Trp Asn Gln Tyr Tyr Asn Val Cys Arg Ser Gly Glu Phe
                340                 345                 350

Asn Pro His Asn Gly Ala Ile Asn Phe Asp Asn Ile Gly Tyr Ala Trp
        355                 360                 365

Ile Ala Ile Phe Gln Val Ile Thr Leu Glu Gly Trp Val Asp Ile Met
    370                 375                 380

Tyr Tyr Val Met Asp Ala His Ser Phe Tyr Asn Phe Ile Tyr Phe Ile
385                 390                 395                 400

Leu Leu Ile Ile Met Gly Ser Phe Phe Met Ile Asn Leu Cys Leu Val
                405                 410                 415

Val Ile Ala Thr Gln Phe Ser Glu Thr Lys Gln Arg Glu Asn Gln Leu
            420                 425                 430

Met Arg Glu Gln Arg Ala Arg Tyr Leu Ser Asn Asp Ser Thr Leu Ala
    435                 440                 445

Ser Phe Ser Glu Pro Gly Ser Cys Tyr Glu Glu Leu Leu Lys Tyr Val
    450                 455                 460

Gly His Ile Phe Arg Lys Val Lys Arg Arg Ser Leu Arg Leu Tyr Ala
```

```
                465                 470                 475                 480
Arg Trp Gln Ser Arg Trp Arg Lys Lys Val Asp Pro Ser Ser Thr Val
                    485                 490                 495
His Gly Gln Gly Pro Gly Arg Arg Pro Arg Ala Gly Arg Arg Thr
                500                 505                 510
Ala Ser Val His His Leu Val Tyr His His His His His His His
            515                 520                 525
His Tyr His Phe Ser His Gly Gly Pro Arg Arg Pro Ser Pro Glu Pro
        530                 535                 540
Gly Ala Gly Asp Asn Arg Leu Val Arg Ala Cys Ala Pro Pro Ser Pro
545                 550                 555                 560
Pro Ser Pro Gly His Gly Pro Pro Asp Ser Glu Ser Val His Ser Ile
                565                 570                 575
Tyr His Ala Asp Cys His Val Glu Gly Pro Gln Glu Arg Ala Arg Val
            580                 585                 590
Ala His Ser Ile Ala Thr Ala Ala Ser Leu Lys Leu Ala Ser Gly Leu
        595                 600                 605
Gly Thr Met Asn Tyr Pro Thr Ile Leu Pro Ser Gly Thr Val Asn Ser
    610                 615                 620
Lys Gly Gly Thr Ser Ser Arg Pro Lys Gly Leu Arg Gly Ala Gly Ala
625                 630                 635                 640
Pro Gly Ala Ala Val His Ser Pro Leu Ser Leu Gly Ser Pro Arg Pro
                645                 650                 655
Tyr Glu Lys Ile Gln Asp Val Val Gly Glu Gln Gly Leu Gly Arg Ala
            660                 665                 670
Ser Ser His Leu Ser Gly Leu Ser Val Pro Cys Pro Leu Pro Ser Pro
        675                 680                 685
Gln Ala Gly Thr Leu Thr Cys Glu Leu Lys Ser Cys Pro Tyr Cys Ala
    690                 695                 700
Ser Ala Leu Glu Asp Pro Glu Phe Glu Phe Ser Gly Ser Glu Ser Gly
705                 710                 715                 720
Asp Ser Asp Ala His Gly Val Tyr Glu Phe Thr Gln Asp Val Arg His
                725                 730                 735
Gly Asp Cys Arg Asp Pro Val Gln Gln Pro His Glu Val Gly Thr Pro
            740                 745                 750
Gly His Ser Asn Glu Arg Arg Thr Pro Leu Arg Lys Ala Ser Gln
        755                 760                 765
Pro Gly Gly Ile Gly His Leu Trp Ala Ser Phe Ser Gly Lys Leu Arg
    770                 775                 780
Arg Ile Val Asp Ser Lys Tyr Phe Asn Arg Gly Ile Met Ala Ala Ile
785                 790                 795                 800
Leu Val Asn Thr Leu Ser Met Gly Val Glu Tyr His Glu Gln Pro Glu
                805                 810                 815
Glu Leu Thr Asn Ala Leu Glu Ile Ser Asn Ile Val Phe Thr Ser Met
            820                 825                 830
Phe Ala Leu Glu Met Leu Leu Lys Leu Leu Ala Cys Gly Pro Leu Gly
        835                 840                 845
Tyr Ile Arg Asn Pro Tyr Asn Ile Phe Asp Gly Ile Val Val Ile
    850                 855                 860
Ser Val Trp Glu Ile Val Gly Gln Ala Asp Gly Gly Gln Ser Val Leu
865                 870                 875                 880
Arg Thr Phe Arg Leu Leu Arg Val Leu Lys Leu Val Arg Phe Leu Pro
                885                 890                 895
```

-continued

```
Ala Leu Arg Arg Gln Leu Val Val Leu Met Arg Thr Met Asp Asn Val
            900                 905                 910

Ala Thr Phe Cys Met Leu Leu Met Leu Phe Ile Phe Ile Phe Ser Ile
        915                 920                 925

Leu Gly Met His Leu Phe Gly Cys Lys Phe Ser Leu Lys Thr Asp Ser
    930                 935                 940

Gly Asp Thr Val Pro Asp Arg Lys Asn Phe Asp Ser Leu Leu Trp Ala
945                 950                 955                 960

Ile Val Thr Val Phe Gln Ile Leu Thr Gln Glu Asp Trp Asn Val Val
                965                 970                 975

Leu Tyr Asn Gly Met Ala Ser Thr Ser Ser Trp Ala Ala Leu Tyr Phe
            980                 985                 990

Val Ala Leu Met Thr Phe Gly Asn Tyr Val Leu Phe Asn Leu Leu Val
        995                 1000                1005

Ala Ile Leu Val Glu Gly Phe Gln Ala Glu Gly Asp Ala Thr Arg Ser
    1010                1015                1020

Asp Thr Asp Glu Asp Lys Thr Ser Thr Gln Leu Glu Gly Asp Phe Asp
1025                1030                1035                1040

Lys Leu Arg Asp Leu Arg Ala Thr Glu Met Lys Met Tyr Ser Leu Ala
                1045                1050                1055

Val Thr Pro Asn Gly His Leu Glu Gly Arg Gly Ser Leu Pro Pro Pro
            1060                1065                1070

Leu Ile Thr His Thr Ala Ala Thr Pro Met Pro Thr Pro Lys Ser Ser
        1075                1080                1085

Pro Asn Leu Asp Val Ala His Ala Leu Leu Asp Ser Arg Arg Ser Ser
    1090                1095                1100

Ser Gly Ser Val Asp Pro Gln Leu Gly Asp Gln Lys Ser Leu Ala Ser
1105                1110                1115                1120

Leu Arg Ser Ser Pro Cys Thr Pro Trp Gly Pro Asn Ser Ala Gly Ser
                1125                1130                1135

Ser Arg Arg Ser Ser Trp Asn Ser Leu Gly Arg Ala Pro Ser Leu Lys
            1140                1145                1150

Arg Arg Ser Gln Cys Gly Glu Arg Glu Ser Leu Leu Ser Gly Glu Gly
        1155                1160                1165

Lys Gly Ser Thr Asp Asp Glu Ala Glu Asp Ser Arg Pro Ser Thr Gly
    1170                1175                1180

Thr His Pro Gly Ala Ser Pro Gly Pro Arg Ala Thr Pro Leu Arg Arg
1185                1190                1195                1200

Ala Glu Ser Leu Asp His Arg Ser Thr Leu Asp Leu Cys Pro Pro Arg
                1205                1210                1215

Pro Ala Pro Pro Ala Val Gln Val His Asp Cys Asn Gly Gln Met Val
            1220                1225                1230

Ala Leu Pro Ser Glu Phe Phe Leu Arg Ile Asp Ser His Lys Glu Asp
        1235                1240                1245

Ala Ala Glu Phe Asp Asp Asp Ile Glu Asp Ser Cys Cys Phe Arg Leu
    1250                1255                1260

His Lys Val Leu Glu Pro Tyr Ala Pro Gln Trp Cys Arg Ser Arg Glu
1265                1270                1275                1280

Ser Trp Ala Leu Tyr Leu Phe Pro Pro Gln Asn Arg Leu Arg Val Ser
                1285                1290                1295

Cys Gln Lys Val Ile Ala His Lys Met Phe Asp His Val Val Leu Val
            1300                1305                1310
```

-continued

```
Phe Ile Phe Leu Asn Cys Ile Thr Ile Ala Leu Glu Arg Pro Asp Ile
    1315                1320                1325
Asp Pro Gly Ser Thr Glu Arg Ala Phe Leu Ser Val Ser Asn Tyr Ile
1330                1335                1340
Phe Thr Ala Ile Phe Val Val Glu Met Met Val Lys Val Val Ala Leu
1345                1350                1355                1360
Gly Leu Leu Trp Gly Glu His Ala Tyr Leu Gln Ser Ser Trp Asn Val
                1365                1370                1375
Leu Asp Gly Leu Leu Val Leu Val Ser Leu Val Asp Ile Ile Val Ala
            1380                1385                1390
Met Ala Ser Ala Gly Gly Ala Lys Ile Leu Gly Val Leu Arg Val Val
        1395                1400                1405
Arg Leu Leu Arg Thr Leu Arg Pro Leu Arg Val Ile Ser Arg Ala Pro
    1410                1415                1420
Gly Leu Lys Leu Val Val Glu Thr Leu Ile Ser Ser Leu Arg Pro Ile
1425                1430                1435                1440
Gly Asn Ile Val Leu Ile Cys Cys Ala Phe Phe Ile Ile Phe Gly Ile
                1445                1450                1455
Leu Gly Val Gln Leu Phe Lys Gly Lys Phe Tyr Tyr Cys Glu Gly Thr
            1460                1465                1470
Asp Thr Arg Asn Ile Thr Thr Lys Ala Glu Cys His Ala Ala His Tyr
        1475                1480                1485
Arg Trp Val Arg Arg Lys Tyr Asn Phe Asp Asn Leu Gly Gln Ala Leu
    1490                1495                1500
Met Ser Leu Phe Val Leu Ser Ser Lys Asp Gly Trp Val Asn Ile Met
1505                1510                1515                1520
Tyr Asp Gly Leu Asp Ala Val Gly Ile Asp Gln Gln Pro Val Gln Asn
                1525                1530                1535
His Asn Pro Trp Met Leu Leu Tyr Phe Ile Ser Phe Leu Leu Ile Val
            1540                1545                1550
Ser Phe Phe Val Leu Asn Met Phe Val Gly Val Val Val Glu Asn Phe
        1555                1560                1565
His Lys Cys Arg Gln His Gln Glu Ala Glu Glu Ala Arg Arg Arg Glu
    1570                1575                1580
Glu Lys Arg Leu Arg Arg Leu Glu Arg Arg Arg Arg Lys Ala Gln Arg
1585                1590                1595                1600
Arg Pro Tyr Tyr Ala Asp Tyr Ser His Thr Arg Arg Ser Ile His Ser
                1605                1610                1615
Leu Cys Thr Ser His Tyr Leu Asp Leu Phe Ile Thr Phe Ile Ile Cys
            1620                1625                1630
Leu Asn Val Ile Thr Met Ser Met Glu His Tyr Asn Gln Pro Lys Ser
        1635                1640                1645
Leu Asp Glu Ala Leu Lys Tyr Cys Asn Tyr Val Phe Thr Ile Val Phe
    1650                1655                1660
Val Phe Glu Ala Ala Leu Lys Leu Val Ala Phe Gly Phe Arg Arg Phe
1665                1670                1675                1680
Phe Lys Asp Arg Trp Asn Gln Leu Asp Leu Ala Ile Val Leu Leu Ser
                1685                1690                1695
Ile Met Gly Ile Ala Leu Glu Glu Ile Glu Met Asn Ala Ala Leu Pro
            1700                1705                1710
Ile Asn Pro Thr Ile Ile Arg Ile Met Arg Val Leu Arg Ile Ala Arg
        1715                1720                1725
Val Leu Lys Leu Leu Lys Met Ala Thr Gly Met Arg Ala Leu Leu Asp
```

-continued

```
                1730                1735                1740
Thr Val Val Gln Ala Leu Pro Gln Val Gly Asn Leu Gly Leu Leu Phe
1745                1750                1755                1760

Met Leu Leu Phe Phe Ile Tyr Ala Ala Leu Gly Val Glu Leu Phe Gly
                1765                1770                1775

Arg Leu Glu Cys Ser Glu Asp Asn Pro Cys Glu Gly Leu Ser Arg His
                1780                1785                1790

Ala Thr Phe Thr Asn Phe Gly Met Ala Phe Leu Thr Leu Phe Arg Val
            1795                1800                1805

Ser Thr Gly Asp Asn Trp Asn Gly Ile Met Lys Asp Thr Leu Arg Glu
        1810                1815                1820

Cys Thr Arg Glu Asp Lys His Cys Leu Ser Tyr Leu Pro Ala Leu Ser
1825                1830                1835                1840

Pro Val Tyr Phe Val Thr Phe Met Leu Val Ala Gln Phe Val Leu Val
                1845                1850                1855

Asn Val Val Val Ala Val Leu Met Lys His Leu Glu Glu Ser Asn Lys
                1860                1865                1870

Glu Ala Arg Glu Asp Ala Glu Met Asp Ala Glu Ile Glu Leu Glu Met
            1875                1880                1885

Ala Gln Gly Ser Thr Ala Gln Pro Pro Thr Ala Gln Glu Ser Gln
        1890                1895                1900

Gly Thr Gln Pro Asp Thr Pro Asn Leu Leu Val Val Arg Lys Val Ser
1905                1910                1915                1920

Val Ser Arg Met Leu Ser Leu Pro Asn Asp Ser Tyr Met Phe Arg Pro
                1925                1930                1935

Val Ala Pro Ala Ala Ala Pro His Ser His Pro Leu Gln Glu Val Glu
            1940                1945                1950

Met Glu Thr Tyr Thr Gly Pro Val Thr Ser Ala His Ser Pro Pro Leu
        1955                1960                1965

Glu Pro Arg Ala Ser Phe Gln Val Pro Ser Ala Ala Ser Ser Pro Ala
1970                1975                1980

Arg Val Ser Asp Pro Leu Cys Ala Leu Ser Pro Arg Gly Thr Pro Arg
1985                1990                1995                2000

Ser Leu Ser Leu Ser Arg Ile Leu Cys Arg Gln Glu Ala Met His Ser
            2005                2010                2015

Glu Ser Leu Glu Gly Lys Val Asp Asp Val Gly Gly Asp Ser Ile Pro
            2020                2025                2030

Asp Tyr Thr Glu Pro Ala Glu Asn Met Ser Thr Ser Gln Ala Ser Thr
        2035                2040                2045

Gly Ala Pro Arg Ser Pro Pro Cys Ser Pro Arg Pro Ala Ser Val Arg
    2050                2055                2060

Thr Arg Lys His Thr Phe Gly Gln Arg Cys Ile Ser Ser Arg Pro Pro
2065                2070                2075                2080

Thr Leu Gly Gly Asp Glu Ala Glu Ala Ala Asp Pro Ala Asp Glu Glu
            2085                2090                2095

Val Ser His Ile Thr Ser Ser Ala His Pro Trp Pro Ala Thr Glu Pro
            2100                2105                2110

His Ser Pro Glu Ala Ser Pro Thr Ala Ser Pro Val Lys Gly Thr Met
        2115                2120                2125

Gly Ser Gly Arg Asp Pro Arg Arg Phe Cys Ser Val Asp Ala Gln Ser
    2130                2135                2140

Phe Leu Asp Lys Pro Gly Arg Pro Asp Ala Gln Arg Trp Ser Ser Val
2145                2150                2155                2160
```

-continued

```
Glu Leu Asp Asn Gly Glu Ser His Leu Glu Ser Gly Glu Val Arg Gly
            2165                2170                2175
Arg Ala Ser Glu Leu Glu Pro Ala Leu Gly Ser Arg Arg Lys Lys Lys
        2180                2185                2190
Met Ser Pro Pro Cys Ile Ser Ile Glu Pro Pro Thr Lys Asp Glu Gly
    2195                2200                2205
Ser Ser Arg Pro Ala Ala Glu Gly Gly Asn Thr Thr Leu Arg Arg
    2210                2215                2220
Arg Thr Pro Ser Cys Glu Ala Ala Leu His Arg Asp Cys Pro Glu Pro
2225                2230                2235                2240
Thr Glu Gly Pro Gly Thr Gly Gly Asp Pro Val Ala Lys Gly Glu Arg
            2245                2250                2255
Trp Gly Gln Ala Ser Cys Arg Ala Glu His Leu Thr Val Pro Asn Phe
        2260                2265                2270
Ala Phe Glu Pro Leu Asp Met Gly Gly Pro Gly Gly Asp Cys Phe Leu
    2275                2280                2285
Asp Ser Asp Gln Ser Val Thr Pro Glu Pro Arg Val Ser Ser Leu Gly
        2290                2295                2300
Ala Ile Val Pro Leu Ile Leu Glu Thr Glu Leu Ser Met Pro Ser Pro
2305                2310                2315                2320
Asp Cys Pro Glu Lys Glu Gln Gly Leu Tyr Leu Thr Val Pro Gln Thr
            2325                2330                2335
Pro Leu Lys Lys Pro Gly Ser Thr Pro Ala Thr Pro Ala Pro Asp Asp
        2340                2345                2350
Ser Gly Asp Glu Pro Val Glx
    2355
```

<210> SEQ ID NO 27
<211> LENGTH: 5735
<212> TYPE: DNA
<213> ORGANISM: rat

<400> SEQUENCE: 27

```
ccggcttcgg cgccgtgccc ggccacgtcc atgccaaggg ctccctgctc cacgctgaca    60
tggctgacag caacttaccg ccctcatctg cagcagcccc ggcccccgag ccggaaatca   120
ctgagcagcc ggggccccgg agtccccctc catcccctcc aggcctggag gagccattgg   180
aaggaaccaa ccctgacgtc ccacatccag acctggctcc tgttgctttc ttctgcctgc   240
gccagaccac gagcccacgg aactggtgca tcaagatggt ttgtaacccg tggttcgagt   300
gtgtgagcat gctggttatt ctgctgaact gtgtgaccct gggcatgtac cagccatgtg   360
atgacatgga gtgcctgtcg gaccgttgca agatcctgca ggtcttcgat gacttcatct   420
tcatcttctt tgccatggag atggtgctta agatggtggc cctgggcatt tttggcaaga   480
agtgctacct cggagacaca tggaaccgcc tggatttctt cattgtcatg caggggatgg   540
ttgagtactc tctggaccta cagaacatca acctgtcagc catccgcact gtgcgtgtcc   600
tgaggcctct caaagccatc aaccgtgtac cagcctgcg gatcctggtg aacctgctgc   660
tcgacacgct gcccatgctg gggaacgtgc tcctgctctg tttcttcgtc ttcttcatct   720
tcggcatcat tggcgtgcag ctctgggcag gctgctacg gaaccgctgc ttcctggaag   780
aaaacttcac catacaaggg gatgtggccc tgccccctta ttaccaacca gaggaggatg   840
acgagatgcc ctttatctgc tcctgactg gggacaatgg catcatgggc tgccacgaga   900
tcccccccact gaaggagcag ggccgggaag tctgcctgtc caaagatgat gtgtatgact   960
```

```
tcggggcggg gcgccaggac ctcaacgcca gcggtctgtg cgtcaactgg aaccgctact    1020
acaacgtctg ccgcacgggc aacgccaacc ctcacaaggg cgccatcaac tttgacaaca    1080
ttggctatgc ctggattgtg attttccagg tgatcactct ggaaggctgg gtggagatca    1140
tgtactatgt gatggacgca cattctttct acaacttcat tctgctcatc atagtgggct    1200
ccttcttcat gatcaacttg tgcctcgttc tcatagcaac ccagttctct gagaccaagc    1260
aacggaacca ccggctgatg ctggagcaac gccagcgcta cctgtcctcc agcacggtgg    1320
ccagttacgc tgagcccggt gattgctatg aggagatctt ccaatatgtc tgtcacatcc    1380
ttcgcaaagc caagcgccgt gccctaggcc tctaccaggc cctgcagaac cggcgccagg    1440
ccatgggccc ggggacacca gcccctgcca agcctgggcc ccatgccaag gagcccagcc    1500
actcgaagct gtgcccacga cacagccccc tggacccac tccccacaca ctggtgcagc    1560
ccatctctgc cattctggcc tcttacccca gcagctgccc tcactgccag cacgaggcag    1620
gcaggcggcc ctctggcctg gcagcactg actcaggcca ggaaggctca ggttctggtg    1680
gctctgcaga ggccgaagcc aatggggatg actccagag cagagaggat ggggtctcct    1740
cggacctggg gaaggaggag gaacaggagg acggggcagc ccgactgtgt ggggatgtat    1800
ggcgcgagac acgaaaaaag ctgcggggca tcgtggacag caagtacttc aacagaggta    1860
tcatgatggc tatcctggtg aacacagtca gcatgggcat cgagcaccac gaacagcccg    1920
aggagctgac caacatcctg gagatctgca atgtggtctt caccagtatg tttgccctgg    1980
agatgatcct gaaactggcc gcctttgggc tcttcgacta cctgcggaac ccttacaaca    2040
tctttgacag catcatcgtc atcatcagca tctgggaaat cgtggggcag gcggacagtg    2100
gcctgtctgt gctgcgcact tcccggttgc tgcgggtgct gaagctagtg cgcttcatgc    2160
cggcgctgcg ccagctcgtg gtgctcatga agaccatgga caacgtggcc accttctgca    2220
tgctactcat gctgttcatc ttcatcttca gcatccttgg gatcgatatc tttggctgca    2280
aattcagcct ccgcacggac acgggagaca ccgttcctga caggaagaac ttcgattcct    2340
tactgtgggc catcgtcaca gtgttccaga tcctcactca ggaggactgg aacgttgtcc    2400
tgtacaatgg catggcctcc accacccct gggcctccct ctattttgtt gccctcatga    2460 cctttgcaa ctacgttctc ttcaatctcc tggtggctat cctggtagag ggtttccagg    2520
ctgagggtga tgctaatcgt tcctactctg atgaggacca gagctcatcc aatttagagg    2580
agttagacaa gctcccagag ggcctggaca acaggagaga tctcaagctc tgcccaatac    2640
ccatgacacc caatggacac ctggaccca gcctccctct gggtgcgcat ctgggtcctg    2700
ctggtaccat gggtactgcc ccccgcctct cactgcagcc agacccggta ctggtggccc    2760
gggactctcg gaaaagcagt tactggtccc tgggcaggat gagctatgat cagcgatcct    2820
tgtccagctc ccggagctcc tactacggcc tgggggccg cagtgggacc tgggctagcc    2880
gccgctccag ctggaacagc ctgaaacaca agccgccctc agctgagcat gagtccttac    2940
tgtctgggga gggtggaggt agctgcgtca gggcctgtga aggcgcccgg gaggaggcgc    3000
caactcgcac cgcacccctg catgctccac accggcacca cgcgcaccat ggaccccacc    3060
tggcacaccg tcaccgacac caccgccgga ctctgtccct cgataccagg gactctgttg    3120
acctgggaga gctggtgccc gtggtgggtg cccactcacg ggccgcttgg aggggggcgg    3180
gtcaggcccc tggcacgag gactgcaatg gcagaatgcc caacatggcc aaggatgtct    3240
tcaccaagat ggatgaccgc cgcgaccgcg gggaggacga ggaggagatc gactataccc    3300
```

-continued

| | |
|---|---|
| tgtgtttccg ggtccgcaag atgatttgct gtgtgtacaa gccggactgg tgcgaagtcc | 3360 |
| gcgaggactg gtcggtctac ctcttctccc ccgagaacaa gttccggatc ctgtgtcaga | 3420 |
| ctatcattgc tcacaagctt tttgactacg tggtcttggc ctttatcttc ctcaactgta | 3480 |
| tcaccattgc tctggagaga ccccagattg aagctggtag cactgagcgc atcttcctca | 3540 |
| cggtgtctaa ctacatcttc acagccatct tcgtgggcga gatgacactg aaggtggttt | 3600 |
| ctctgggcct gtactttggt gagcaggcgt acctgcgtac ggactggaat gtactggatg | 3660 |
| gtttcctggt ctttgtgtcc atcatcgata tcgtagtgtc cgtggcctct gctggggag | 3720 |
| ccaagattct gggggtcctg cggctcctgc gtaccttacg tcctttgaga gttatcagcc | 3780 |
| gggcccctgg gctgaagctg gtggtagaga cgctcatctc ctccctcaag cccattggga | 3840 |
| acatcgtcct catctgctgt gccttcttca tcatcttcgg catcctgggg gtgcagcttt | 3900 |
| tcaaaggcaa gttctaccat tgtttgggag tggacacccg aaacatcacc aaccgatctg | 3960 |
| actgcgtggc ggccaactac cgctgggtgc atcacaaata caactttgac aacctgggcc | 4020 |
| aggcattgat gtccctcttt gtcttggcct ccaaggacgg ctgggtgaac atcatgtata | 4080 |
| atggattaga tgctgttgct gtggaccagc agcccgtgac gaaccacaac ccctggatgc | 4140 |
| tactgtactt catttcgttc ctgctcatcg tcagcttctt tgtgctcaac atgtttgtgg | 4200 |
| gcgtggtcgt ggagaacttc cacaagtgcc ggcagcacca ggaggctgag gaggcgcgga | 4260 |
| ggcgtgagga gaaacggctg cggcgcctgg aaaagaagcg ccgttacgct cagaggctgc | 4320 |
| cctactatgc tacctactgt cccacaaggc tgctcatcca ctccatgtgc accagccact | 4380 |
| acctggacat cttcattacc ttcatcatct gcctcaatgt tgtcaccatg tccctggagc | 4440 |
| actacaacca gctacatcc ctagagacag cccttaagta ctgcaactac atgttcacca | 4500 |
| ctgtgtttgt gctggaggct gtgctgaagc tggtggcatt tggcctgagg cgtttcttca | 4560 |
| aggaccgatg gaaccagctg gacctggcca ttgtgctgct gtccgtcatg ggcatcacac | 4620 |
| tggaggagat cgagatcaat gccgcccttc ccatcaaccc caccatcatc cgtatcatgc | 4680 |
| gtgttctgcg tatcgcccgg gtgttgaagc tattgaagat ggccacagga atgcgggccc | 4740 |
| tgctggacac agtggtacag gctctgcccc aggtgggcaa cctgggcctg ctcttcatgc | 4800 |
| tgctcttctt catctatgct gctctgggag tggagctctt cggaaagctg gtctgcaatg | 4860 |
| acgagaaccc gtgtgagggt atgagccggc acgccacctt tgaaaactct gctagggcct | 4920 |
| tcctcacgct cttccaggtc tccacaggcg ataactggaa tggaattatg aaggacaccc | 4980 |
| tgcgagactg tacccatgat gagcgcacgt gcctaagcag cctgcagttt gtgtcaccgc | 5040 |
| tctactttgt gagcttcgtg ctcacagctc agttcgtgct catcaacgtg gtggtggccg | 5100 |
| tgctgatgaa acatctggat gacagcaaca aggaggccca ggaggatgca gagatggatg | 5160 |
| ctgagatcga gctggagatg gcccatggct ccggcccctg ccctggcccc tgccctggtc | 5220 |
| cctgccctg cccctgcccc tgcccctgtt ctggcccgag gtgcccacta gttacctggg | 5280 |
| gctcgggggc gatggatcgg gaggggcagg tgctggaggc acaccgagag tcacctgtgc | 5340 |
| gcactgctat caggtgctgg acaccgagag tcacctgtgc cggcactgct attctccagc | 5400 |
| ccaggagacc ctgtggctgg acagggtctc tttaatcatc aaggactcct ggaggggga | 5460 |
| gctgaccatc attgacaacc tgtctgggtc cgtcttccac cactacgcct cactgacggc | 5520 |
| tgtggcaagt gtcaccatga caagcaagag gtgcagctgg ctgagacaga ggccttctcc | 5580 |
| ctgaactcag acaggtcttc atccatcctg ctggggatg acctgagtct tgaggacccc | 5640 |
| acggcctcgc acagggcccc aaaggagagc aagggtgaac aataaagagc ctccggagcc | 5700 |

```
catgcaggct ggagacctgg atgaatgcaa aaaaa                              5735
```

<210> SEQ ID NO 28
<211> LENGTH: 1792
<212> TYPE: PRT
<213> ORGANISM: rat

<400> SEQUENCE: 28

```
Met Ala Asp Ser Asn Leu Pro Pro Ser Ala Ala Pro Ala Pro
 1               5                  10                  15

Glu Pro Gly Ile Thr Glu Gln Pro Gly Pro Arg Ser Pro Pro Ser
                20                  25                  30

Pro Pro Gly Leu Glu Glu Pro Leu Gly Thr Asn Pro Asp Val Pro
            35                  40                  45

His Pro Asp Leu Ala Pro Val Ala Phe Phe Cys Leu Arg Gln Thr Thr
        50                  55                  60

Ser Pro Arg Asn Trp Cys Ile Lys Met Val Cys Asn Pro Trp Phe Glu
 65                  70                  75                  80

Cys Val Ser Met Leu Val Ile Leu Leu Asn Cys Val Thr Leu Gly Met
                85                      90                  95

Tyr Gln Pro Cys Asp Asp Met Glu Cys Leu Ser Asp Arg Cys Lys Ile
                100                 105                 110

Leu Gln Val Phe Asp Asp Phe Ile Phe Ile Phe Phe Ala Met Glu Met
            115                 120                 125

Val Leu Lys Met Val Ala Leu Gly Ile Phe Gly Lys Lys Cys Tyr Leu
        130                 135                 140

Gly Asp Thr Trp Asn Arg Leu Asp Phe Phe Ile Val Met Ala Gly Met
145                 150                 155                 160

Val Glu Tyr Ser Leu Asp Leu Gln Asn Ile Asn Leu Ser Ala Ile Arg
                165                 170                 175

Thr Val Arg Val Leu Arg Pro Leu Lys Ala Ile Asn Arg Val Pro Ser
            180                 185                 190

Leu Arg Ile Leu Val Asn Leu Leu Leu Asp Thr Leu Pro Met Leu Gly
        195                 200                 205

Asn Val Leu Leu Leu Cys Phe Phe Val Phe Phe Ile Phe Gly Ile Ile
    210                 215                 220

Gly Val Gln Leu Trp Ala Gly Leu Leu Arg Asn Arg Cys Phe Leu Glu
225                 230                 235                 240

Glu Asn Phe Thr Ile Gln Gly Asp Val Ala Leu Pro Pro Tyr Tyr Gln
                245                 250                 255

Pro Glu Glu Asp Asp Glu Met Pro Phe Ile Cys Ser Leu Thr Gly Asp
            260                 265                 270

Asn Gly Ile Met Gly Cys His Glu Ile Pro Pro Leu Lys Glu Gln Gly
        275                 280                 285

Arg Glu Val Cys Leu Ser Lys Asp Val Tyr Asp Phe Gly Ala Gly
    290                 295                 300

Arg Gln Asp Leu Asn Ala Ser Gly Leu Cys Val Asn Trp Asn Arg Tyr
305                 310                 315                 320

Tyr Asn Val Cys Arg Thr Gly Asn Ala Asn Pro His Lys Gly Ala Ile
                325                 330                 335

Asn Phe Asp Asn Ile Gly Tyr Ala Trp Ile Val Ile Phe Gln Val Ile
            340                 345                 350

Thr Leu Glu Gly Trp Val Glu Ile Met Tyr Tyr Val Met Asp Ala His
        355                 360                 365
```

-continued

```
Ser Phe Tyr Asn Phe Ile Leu Leu Ile Ile Val Gly Ser Phe Phe Met
    370                 375                 380

Ile Asn Leu Cys Leu Val Leu Ile Ala Thr Gln Phe Ser Glu Thr Lys
385                 390                 395                 400

Gln Arg Asn His Arg Leu Met Leu Glu Gln Arg Gln Arg Tyr Leu Ser
                405                 410                 415

Ser Ser Thr Val Ala Ser Tyr Ala Glu Pro Gly Asp Cys Tyr Glu Glu
                420                 425                 430

Ile Phe Gln Tyr Val Cys His Ile Leu Arg Lys Ala Lys Arg Arg Ala
                435                 440                 445

Leu Gly Leu Tyr Gln Ala Leu Gln Asn Arg Arg Gln Ala Met Gly Pro
    450                 455                 460

Gly Thr Pro Ala Pro Ala Lys Pro Gly Pro His Ala Lys Glu Pro Ser
465                 470                 475                 480

His Ser Lys Leu Cys Pro Arg His Ser Pro Leu Asp Pro Thr Pro His
                485                 490                 495

Thr Leu Val Gln Pro Ile Ser Ala Ile Leu Ala Ser Tyr Pro Ser Ser
                500                 505                 510

Cys Pro His Cys Gln His Glu Ala Gly Arg Arg Pro Ser Gly Leu Gly
                515                 520                 525

Ser Thr Asp Ser Gly Gln Glu Gly Ser Gly Ser Gly Ser Ala Glu
    530                 535                 540

Ala Glu Ala Asn Gly Asp Gly Leu Gln Ser Arg Glu Asp Gly Val Ser
545                 550                 555                 560

Ser Asp Leu Gly Lys Glu Glu Gln Glu Asp Gly Ala Ala Arg Leu
                565                 570                 575

Cys Gly Asp Val Trp Arg Glu Thr Arg Lys Lys Leu Arg Gly Ile Val
                580                 585                 590

Asp Ser Lys Tyr Phe Asn Arg Gly Ile Met Met Ala Ile Leu Val Asn
                595                 600                 605

Thr Val Ser Met Gly Ile Glu His His Glu Gln Pro Glu Glu Leu Thr
    610                 615                 620

Asn Ile Leu Glu Ile Cys Asn Val Val Phe Thr Ser Met Phe Ala Leu
625                 630                 635                 640

Glu Met Ile Leu Lys Leu Ala Ala Phe Gly Leu Phe Asp Tyr Leu Arg
                645                 650                 655

Asn Pro Tyr Asn Ile Phe Asp Ser Ile Ile Val Ile Ile Ser Ile Trp
                660                 665                 670

Glu Ile Val Gly Gln Ala Asp Ser Gly Leu Ser Val Leu Arg Thr Ser
                675                 680                 685

Arg Leu Leu Arg Val Leu Lys Leu Val Arg Phe Met Pro Ala Leu Arg
    690                 695                 700

Gln Leu Val Val Leu Met Lys Thr Met Asp Asn Val Ala Thr Phe Cys
705                 710                 715                 720

Met Leu Leu Met Leu Phe Ile Phe Ile Phe Ser Ile Leu Gly Ile Asp
                725                 730                 735

Ile Phe Gly Cys Lys Phe Ser Leu Arg Thr Asp Thr Gly Asp Thr Val
                740                 745                 750

Pro Asp Arg Lys Asn Phe Asp Ser Leu Leu Trp Ala Ile Val Thr Val
                755                 760                 765

Phe Gln Ile Leu Thr Gln Glu Asp Trp Asn Val Val Leu Tyr Asn Gly
    770                 775                 780
```

```
Met Ala Ser Thr Thr Pro Trp Ala Ser Leu Tyr Phe Val Ala Leu Met
785                 790                 795                 800

Thr Phe Gly Asn Tyr Val Leu Phe Asn Leu Leu Val Ala Ile Leu Val
            805                 810                 815

Glu Gly Phe Gln Ala Glu Gly Asp Ala Asn Arg Ser Tyr Ser Asp Glu
        820                 825                 830

Asp Gln Ser Ser Ser Asn Leu Glu Glu Leu Asp Lys Leu Pro Glu Gly
    835                 840                 845

Leu Asp Asn Arg Arg Asp Leu Lys Leu Cys Pro Ile Pro Met Thr Pro
850                 855                 860

Asn Gly His Leu Asp Pro Ser Leu Pro Leu Gly Ala His Leu Gly Pro
865                 870                 875                 880

Ala Gly Thr Met Gly Thr Ala Pro Arg Leu Ser Leu Gln Pro Asp Pro
            885                 890                 895

Val Leu Val Ala Arg Asp Ser Arg Lys Ser Ser Tyr Trp Ser Leu Gly
        900                 905                 910

Arg Met Ser Tyr Asp Gln Arg Ser Leu Ser Ser Ser Arg Ser Ser Tyr
    915                 920                 925

Tyr Gly Pro Gly Gly Arg Ser Gly Thr Trp Ala Ser Arg Arg Ser Ser
930                 935                 940

Trp Asn Ser Leu Lys His Lys Pro Pro Ser Ala Glu His Glu Ser Leu
945                 950                 955                 960

Leu Ser Gly Glu Gly Gly Ser Cys Val Arg Ala Cys Glu Gly Ala
            965                 970                 975

Arg Glu Glu Ala Pro Thr Arg Thr Ala Pro Leu His Ala Pro His Arg
        980                 985                 990

His His Ala His His Gly Pro His Leu Ala His Arg His Arg His His
    995                 1000                1005

Arg Arg Thr Leu Ser Leu Asp Thr Arg Asp Ser Val Asp Leu Gly Glu
    1010                1015                1020

Leu Val Pro Val Val Gly Ala His Ser Arg Ala Ala Trp Arg Gly Ala
1025                1030                1035                1040

Gly Gln Ala Pro Gly His Glu Asp Cys Asn Gly Arg Met Pro Asn Met
                1045                1050                1055

Ala Lys Asp Val Phe Thr Lys Met Asp Asp Arg Arg Asp Arg Gly Glu
            1060                1065                1070

Asp Glu Glu Glu Ile Asp Tyr Thr Leu Cys Phe Arg Val Arg Lys Met
        1075                1080                1085

Ile Cys Cys Val Tyr Lys Pro Asp Trp Cys Glu Val Arg Glu Asp Trp
1090                1095                1100

Ser Val Tyr Leu Phe Ser Pro Glu Asn Lys Phe Arg Ile Leu Cys Gln
1105                1110                1115                1120

Thr Ile Ile Ala His Lys Leu Phe Asp Tyr Val Val Leu Ala Phe Ile
            1125                1130                1135

Phe Leu Asn Cys Ile Thr Ile Ala Leu Glu Arg Pro Gln Ile Glu Ala
        1140                1145                1150

Gly Ser Thr Glu Arg Ile Phe Leu Thr Val Ser Asn Tyr Ile Phe Thr
    1155                1160                1165

Ala Ile Phe Val Gly Glu Met Thr Leu Lys Val Val Ser Leu Gly Leu
    1170                1175                1180

Tyr Phe Gly Glu Gln Ala Tyr Leu Arg Thr Asp Trp Asn Val Leu Asp
1185                1190                1195                1200

Gly Phe Leu Val Phe Val Ser Ile Ile Asp Ile Val Val Ser Val Ala
```

-continued

```
               1205                1210                1215
Ser Ala Gly Gly Ala Lys Ile Leu Gly Val Leu Arg Leu Leu Arg Thr
        1220                1225                1230
Leu Arg Pro Leu Arg Val Ile Ser Arg Ala Pro Gly Leu Lys Leu Val
        1235                1240                1245
Val Glu Thr Leu Ile Ser Ser Leu Lys Pro Ile Gly Asn Ile Val Leu
        1250                1255                1260
Ile Cys Cys Ala Phe Phe Ile Ile Phe Gly Ile Leu Gly Val Gln Leu
1265                1270                1275                1280
Phe Lys Gly Lys Phe Tyr His Cys Leu Gly Val Asp Thr Arg Asn Ile
        1285                1290                1295
Thr Asn Arg Ser Asp Cys Val Ala Ala Asn Tyr Arg Trp Val His His
        1300                1305                1310
Lys Tyr Asn Phe Asp Asn Leu Gly Gln Ala Leu Met Ser Leu Phe Val
        1315                1320                1325
Leu Ala Ser Lys Asp Gly Trp Val Asn Ile Met Tyr Asn Gly Leu Asp
        1330                1335                1340
Ala Val Ala Val Asp Gln Gln Pro Val Thr Asn His Asn Pro Trp Met
1345                1350                1355                1360
Leu Leu Tyr Phe Ile Ser Phe Leu Leu Ile Val Ser Phe Phe Val Leu
        1365                1370                1375
Asn Met Phe Val Gly Val Val Glu Asn Phe His Lys Cys Arg Gln
        1380                1385                1390
His Gln Glu Ala Glu Glu Ala Arg Arg Arg Glu Glu Lys Arg Leu Arg
        1395                1400                1405
Arg Leu Glu Lys Lys Arg Arg Tyr Ala Gln Arg Leu Pro Tyr Tyr Ala
        1410                1415                1420
Thr Tyr Cys Pro Thr Arg Leu Leu Ile His Ser Met Cys Thr Ser His
1425                1430                1435                1440
Tyr Leu Asp Ile Phe Ile Thr Phe Ile Ile Cys Leu Asn Val Val Thr
        1445                1450                1455
Met Ser Leu Glu His Tyr Asn Gln Pro Thr Ser Leu Glu Thr Ala Leu
        1460                1465                1470
Lys Tyr Cys Asn Tyr Met Phe Thr Thr Val Phe Val Leu Glu Ala Val
        1475                1480                1485
Leu Lys Leu Val Ala Phe Gly Leu Arg Arg Phe Phe Lys Asp Arg Trp
        1490                1495                1500
Asn Gln Leu Asp Leu Ala Ile Val Leu Leu Ser Val Met Gly Ile Thr
1505                1510                1515                1520
Leu Glu Glu Ile Glu Ile Asn Ala Ala Leu Pro Ile Asn Pro Thr Ile
        1525                1530                1535
Ile Arg Ile Met Arg Val Leu Arg Ile Ala Arg Val Leu Lys Leu Leu
        1540                1545                1550
Lys Met Ala Thr Gly Met Arg Ala Leu Leu Asp Thr Val Val Gln Ala
        1555                1560                1565
Leu Pro Gln Val Gly Asn Leu Gly Leu Leu Phe Met Leu Leu Phe Phe
        1570                1575                1580
Ile Tyr Ala Ala Leu Gly Val Glu Leu Phe Gly Lys Leu Val Cys Asn
1585                1590                1595                1600
Asp Glu Asn Pro Cys Glu Gly Met Ser Arg His Ala Thr Phe Glu Asn
        1605                1610                1615
Ser Ala Arg Ala Phe Leu Thr Leu Phe Gln Val Ser Thr Gly Asp Asn
        1620                1625                1630
```

```
Trp Asn Gly Ile Met Lys Asp Thr Leu Arg Asp Cys Thr His Asp Glu
       1635                1640                1645

Arg Thr Cys Leu Ser Ser Leu Gln Phe Val Ser Pro Leu Tyr Phe Val
   1650                1655                1660

Ser Phe Val Leu Thr Ala Gln Phe Val Leu Ile Asn Val Val Val Ala
1665                1670                1675                1680

Val Leu Met Lys His Leu Asp Asp Ser Asn Lys Glu Ala Gln Glu Asp
           1685                1690                1695

Ala Glu Met Asp Ala Glu Ile Glu Leu Glu Met Ala His Gly Ser Gly
       1700                1705                1710

Pro Cys Pro Gly Pro Cys Pro Gly Pro Cys Pro Cys Pro Cys Pro Cys
   1715                1720                1725

Pro Cys Ser Gly Pro Arg Cys Pro Leu Val Thr Trp Gly Ser Gly Ala
       1730                1735                1740

Met Asp Arg Glu Gly Gln Val Leu Glu Ala His Arg Glu Ser Pro Val
1745                1750                1755                1760

Arg Thr Ala Ile Arg Cys Trp Thr Pro Arg Val Thr Cys Ala Gly Thr
           1765                1770                1775

Ala Ile Leu Gln Pro Arg Arg Pro Cys Gly Trp Thr Gly Ser Leu Glx
       1780                1785                1790

<210> SEQ ID NO 29
<211> LENGTH: 540
<212> TYPE: DNA
<213> ORGANISM: rat

<400> SEQUENCE: 29
aagcttctct gagccaggca gctgctatga ggagctactc aagtacctgg tgtacatcct    60
ccgaaaagca gcccgaaggc tggcccaggt ctctagggct ataggcgtgc gggctgggct   120
gctcagcagc ccagtggccc gtagtgggca ggagccccag cccagtggca gctgcactcg   180
ctcacaccgt cgtctgtctg tccaccacct ggtccaccac catcaccacc accatcacca   240
ctaccacctg gtaatgggga cgctcagagt tccccgggcc agcccagaga tccaggacag   300
ggatgccaat gggtctcgcc ggctcatgct accaccaccc tctacaccca ctccctctgg   360
gggccctccg aggggtgcgg agtctgtaca cagcttctac catgctgact gccacttgga   420
gccagtccgt tgccaggcac cccctcccag atgcccatcg gaggcatctg gtaggactgt   480
gggtagtggg aaggtgtacc ccactgtgca taccagccct ccaccagaga tactgaagga   540

<210> SEQ ID NO 30
<211> LENGTH: 2212
<212> TYPE: DNA
<213> ORGANISM: HUMAN

<400> SEQUENCE: 30
gtgaggggga gccggccggc tgcccgggaa gccccaggg gcgcagggga agcgggactc     60
gcgccgggcg gggtttccct gcgccccggc gcccgcggg cagcatgccc ctgcgggcag    120
ggggagctgg gctgaactgg ccctcccggg ggctcagctt gcgccctaga gcccaccaga   180 tgtgccccg ccggggcccc cggggttgcgt gaggacacct cctctgaggg gcgccgcttg    240
cccctctccg gatcgcccgg ggccccggct ggccagagga tggacgagga ggaggatgga   300 gcggcgccg aggagtcggg acagccccg agcttcatgc ggctcaacga cctgtcgggg    360
gccgggggcc ggccggggcc ggggtcagca gaaaaggacc cgggcagcgc ggactccgag   420
```

-continued

```
gcggaggggc tgccgtaccc ggcgctggcc ccggtggttt tcttctactt gagccaggac    480
agccgcccgc ggagctggtg tctccgcacg gtctgtaacc cctggtttga gcgcatcagc    540
atgttggtca tccttctcaa ctgcgtgacc ctgggcatgt tccggccatg cgaggacatc    600
gcctgtgact cccagcgctg ccggatcctg caggcctttg atgacttcat ctttgccttc    660
tttgccgtgg agatggtggt gaagatggtg gccttgggca tctttgggaa aaagtgttac    720
ctgggagaca cttggaaccg gcttgacttt ttcatcgtca tcgcagggat gctggagtac    780
tcgctggacc tgcagaacgt cagcttctca gctgtcagga cagtccgtgt gctgcgaccg    840
ctcagggcca ttaaccgggt gcccagcatg cgcatccttg tcacgttgct gctggatacg    900
ctgcccatgc tgggcaacgt cctgctgctc tgcttcttcg tcttcttcat cttcggcatc    960
gtcggcgtcc agctgtgggc agggctgctt cggaaccgat gcttcctacc tgagaatttc   1020
agcctccccc tgagcgtgga cctggagcgc tattaccaga cagagaacga ggatgagagc   1080
cccttcatct gctcccagcc acgcgagaac ggcatgcggt cctgcagaag cgtgcccacg   1140
ctgcgcgggg acggggcgg tggcccacct tgcggtctgg actatgaggc ctacaacagc   1200
tccagcaaca ccacctgtgt caactggaac cagtactaca ccaactgctc agcggggag   1260 cacaaccct tcaagggcgc catcaacttt gacaacattg ctatgcctg atcgccatc   1320 ttccaggtca tcacgctgga gggctgggtc gacatcatgt actttgtgat ggatgctcat   1380
tccttctaca atttcatcta cttcatcctc ctcatcatcg tgggctcctt cttcatgatc   1440
aacctgtgcc tggtggtgat tgccacgcag ttctcagaga ccaagcagcg ggaaagccag   1500
ctgatgcggg agcagcgtgt gcggttcctg tccaacgcca gcaccctggc tagcttctct   1560
gagcccggca gctgctatga ggagctgctc aagtacctgg tgtacatcct tcgtaaggca   1620
gcccgcaggc tggctcaggt ctctcgggca gcaggtgtgc gggttgggct gctcagcagc   1680
ccagcacccc tcgggggcca ggagacccag cccagcagca gctgctctcg ctcccaccgc   1740
cgcctatccg tccaccacct ggtgcaccac caccaccacc atcaccacca ctaccacctg   1800
ggcaatggga cgctcaggga ccccgggc agcccggaga tccaggacag ggatgccaat   1860
gggtcccgcc ggctcatgct gccaccaccc tcgacgcctg ccctctccgg ggcccccct   1920 ggtggcgcag agtctgtgca cagcttctac catgccgact gccacttaga gccagtccgc   1980
tgccaggcgc ccctcccag gtccccatct gaggcatccg gcaggactgt gggcagcggg   2040 aagtgtatc ccaccgtgca caccagcccct ccaccggaga cgctgaagga gaaggcacta   2100
gtagaggtgg ctgccagctc tgggccccca accctcacca gcctcaacat cccacccggg   2160
ccctacagct ccatgcacaa gctgctggag acacagagta caggtgcctg cc           2212
```

<210> SEQ ID NO 31
<211> LENGTH: 644
<212> TYPE: PRT
<213> ORGANISM: HUMAN

<400> SEQUENCE: 31

```
Met Asp Glu Glu Glu Asp Gly Ala Gly Ala Glu Glu Ser Gly Gln Pro
  1               5                  10                  15

Arg Ser Phe Met Arg Leu Asn Asp Leu Ser Gly Ala Gly Gly Arg Pro
             20                  25                  30

Gly Pro Gly Ser Ala Glu Lys Asp Pro Gly Ser Ala Asp Ser Glu Ala
         35                  40                  45

Glu Gly Leu Pro Tyr Pro Ala Leu Ala Pro Val Val Phe Phe Tyr Leu
     50                  55                  60
```

-continued

```
Ser Gln Asp Ser Arg Pro Arg Ser Trp Cys Leu Arg Thr Val Cys Asn
 65                  70                  75                  80

Pro Trp Phe Glu Arg Ile Ser Met Leu Val Ile Leu Leu Asn Cys Val
                 85                  90                  95

Thr Leu Gly Met Phe Arg Pro Cys Glu Asp Ile Ala Cys Asp Ser Gln
            100                 105                 110

Arg Cys Arg Ile Leu Gln Ala Phe Asp Asp Phe Ile Phe Ala Phe Phe
        115                 120                 125

Ala Val Glu Met Val Val Lys Met Val Ala Leu Gly Ile Phe Gly Lys
    130                 135                 140

Lys Cys Tyr Leu Gly Asp Thr Trp Asn Arg Leu Asp Phe Phe Ile Val
145                 150                 155                 160

Ile Ala Gly Met Leu Glu Tyr Ser Leu Asp Leu Gln Asn Val Ser Phe
                165                 170                 175

Ser Ala Val Arg Thr Val Arg Val Leu Arg Pro Leu Arg Ala Ile Asn
            180                 185                 190

Arg Val Pro Ser Met Arg Ile Leu Val Thr Leu Leu Leu Asp Thr Leu
        195                 200                 205

Pro Met Leu Gly Asn Val Leu Leu Leu Cys Phe Phe Val Phe Phe Ile
    210                 215                 220

Phe Gly Ile Val Gly Val Gln Leu Trp Ala Gly Leu Leu Arg Asn Arg
225                 230                 235                 240

Cys Phe Leu Pro Glu Asn Phe Ser Leu Pro Leu Ser Val Asp Leu Glu
                245                 250                 255

Arg Tyr Tyr Gln Thr Glu Asn Glu Asp Glu Ser Pro Phe Ile Cys Ser
            260                 265                 270

Gln Pro Arg Glu Asn Gly Met Arg Ser Cys Arg Ser Val Pro Thr Leu
        275                 280                 285

Arg Gly Asp Gly Gly Gly Pro Pro Cys Gly Leu Asp Tyr Glu Ala
    290                 295                 300

Tyr Asn Ser Ser Ser Asn Thr Thr Cys Val Asn Trp Asn Gln Tyr Tyr
305                 310                 315                 320

Thr Asn Cys Ser Ala Gly Glu His Asn Pro Phe Lys Gly Ala Ile Asn
                325                 330                 335

Phe Asp Asn Ile Gly Tyr Ala Trp Ile Ala Ile Phe Gln Val Ile Thr
            340                 345                 350

Leu Glu Gly Trp Val Asp Ile Met Tyr Phe Val Met Asp Ala His Ser
        355                 360                 365

Phe Tyr Asn Phe Ile Tyr Phe Ile Leu Leu Ile Ile Val Gly Ser Phe
    370                 375                 380

Phe Met Ile Asn Leu Cys Leu Val Val Ile Ala Thr Gln Phe Ser Glu
385                 390                 395                 400

Thr Lys Gln Arg Glu Ser Gln Leu Met Arg Glu Gln Arg Val Arg Phe
                405                 410                 415

Leu Ser Asn Ala Ser Thr Leu Ala Ser Phe Ser Glu Pro Gly Ser Cys
            420                 425                 430

Tyr Glu Glu Leu Leu Lys Tyr Leu Val Tyr Ile Leu Arg Lys Ala Ala
        435                 440                 445

Arg Arg Leu Ala Gln Val Ser Arg Ala Ala Gly Val Arg Val Gly Leu
    450                 455                 460

Leu Ser Ser Pro Ala Pro Leu Gly Gly Gln Glu Thr Gln Pro Ser Ser
465                 470                 475                 480
```

-continued

```
Ser Cys Ser Arg Ser His Arg Arg Leu Ser Val His His Leu Val His
                485                 490                 495
His His His His His His His His Tyr His Leu Gly Asn Gly Thr Leu
            500                 505                 510
Arg Ala Pro Arg Ala Ser Pro Glu Ile Gln Asp Arg Asp Ala Asn Gly
            515                 520                 525
Ser Arg Arg Leu Met Leu Pro Pro Ser Thr Pro Ala Leu Ser Gly
        530                 535                 540
Ala Pro Pro Gly Gly Ala Glu Ser Val His Ser Phe Tyr His Ala Asp
545                 550                 555                 560
Cys His Leu Glu Pro Val Arg Cys Gln Ala Pro Pro Arg Ser Pro
                565                 570                 575
Ser Glu Ala Ser Gly Arg Thr Val Gly Ser Gly Lys Val Tyr Pro Thr
            580                 585                 590
Val His Thr Ser Pro Pro Glu Thr Leu Lys Glu Lys Ala Leu Val
        595                 600                 605
Glu Val Ala Ala Ser Ser Gly Pro Pro Thr Leu Thr Ser Leu Asn Ile
    610                 615                 620
Pro Pro Gly Pro Tyr Ser Ser Met His Lys Leu Leu Glu Thr Gln Ser
625                 630                 635                 640
Thr Gly Ala Cys
```

<210> SEQ ID NO 32
<211> LENGTH: 1608
<212> TYPE: DNA
<213> ORGANISM: HUMAN

<400> SEQUENCE: 32

| | | | | | |
|---|---|---|---|---|---|
| atgcccgcgg | ggacgccgcc | ggccagcaga | gcgaggtgct | gccggccgcc | accatgaccg | 60 |
| agggcgcacg | ggccgccgac | gaggtccggg | tgcccctggg | cgcgccgccc | cctggccctg | 120 |
| cggcgttggt | gggggcgtcc | ccggagagcc | ccggggcgcc | gggacgcgag | gcggagcggg | 180 |
| ggtccgagct | cggcgtgtca | ccctccgaga | gcccggcggc | cgagcgcggc | gcggagctgg | 240 |
| gtgccgacga | ggagcagcgc | gtcccgtacc | cggccttggc | ggccacggtc | ttcttctgcc | 300 |
| tcggtcagac | cacgcggccg | cgcagctggt | gcctccggct | ggtctgcaac | ccatggttcg | 360 |
| agcacgtgag | catgctggta | atcatgctca | actgcgtgac | cctgggcatg | ttccggccct | 420 |
| gtgaggacgt | tgagtgcggc | tccgagcgct | gcaacatcct | ggaggccttt | gacgccttca | 480 |
| ttttcgcctt | ttttgcggtg | gagatggtca | tcaagatggt | ggccttgggg | ctgttcgggc | 540 |
| agaagtgtta | cctgggtgac | acgtggaaca | ggctggattt | cttcatcgtc | gtggcgggca | 600 |
| tgatggagta | ctcgttggac | ggacacaacg | tgagcctctc | ggctatcagg | accgtgcggg | 660 |
| tgctgcggcc | cctccgcgcc | atcaaccgcg | tgcctagcat | gcggatcctg | gtcactctgc | 720 |
| tgctggatac | gctgcccatg | ctcgggaacg | tccttctgct | gtgcttcttc | gtcttcttca | 780 |
| ttttcggcat | cgttggcgtc | agctctgggc | tggcctcct | gcggaaccgc | tgcttcctgg | 840 |
| acagtgcctt | tgtcaggaac | aacaacctga | ccttcctgcg | gccgtactac | agacggagg | 900 |
| agggcgagga | gaacccgttc | atctgctcct | cacgccgaga | caacggcatg | cagaagtgct | 960 |
| cgcacatccc | cggccgccgc | gagctgcgca | tgcctgcac | cctgggctgg | aggcctaca | 1020 |
| cgcagccgca | ggccgagggg | gtgggcgctg | cacgcaacgc | ctgcatcaac | tggaaccagt | 1080 |
| actacaacgt | gtgccgctcg | ggtgactcca | accccacaa | cggtgccatc | aacttcgaca | 1140 |
| acatcggcta | cgcctggatc | gccatcttcc | aggtgatcac | gctggaaggc | tgggtggaca | 1200 |

-continued

```
tcatgtacta cgtcatggac gcccactcat tctacaactt catctatttc atcctgctca    1260
tcatcgtggg ctccttcttc atgatcaacc tgtgcctggt ggtgattgcc acgcagttct    1320
cggagacgaa gcagcgggag agtcagctga tgcgggagca gcgggcacgc cacctgtcca    1380
acgacagcac gctggccagc ttctccgagc ctggcagctg ctacgaagag ctgctgaagt    1440
acgtgggcca catattccgc aaggtcaagc ggcgcagctt gcgcctctac gcccgctggc    1500
agagccgctg gcgcaagaag gtggacccca gtgctgtgca aggccagggt cccgggcacc    1560
gccagcgccg ggcaggcagg cacacagcct cggtgcacca cctggtct                 1608
```

<210> SEQ ID NO 33
<211> LENGTH: 518
<212> TYPE: PRT
<213> ORGANISM: HUMAN

<400> SEQUENCE: 33

```
Met Thr Glu Gly Ala Arg Ala Ala Asp Glu Val Arg Val Pro Leu Gly
 1               5                  10                  15

Ala Pro Pro Gly Pro Ala Ala Leu Val Gly Ala Ser Pro Glu Ser
            20                  25                  30

Pro Gly Ala Pro Gly Arg Glu Ala Glu Arg Gly Ser Glu Leu Gly Val
        35                  40                  45

Ser Pro Ser Glu Ser Pro Ala Ala Glu Arg Gly Ala Glu Leu Gly Ala
    50                  55                  60

Asp Glu Glu Gln Arg Val Pro Tyr Pro Ala Leu Ala Ala Thr Val Phe
65                  70                  75                  80

Phe Cys Leu Gly Gln Thr Thr Arg Pro Arg Ser Trp Cys Leu Arg Leu
                85                  90                  95

Val Cys Asn Pro Trp Phe Glu His Val Ser Met Leu Val Ile Met Leu
            100                 105                 110

Asn Cys Val Thr Leu Gly Met Phe Arg Pro Cys Glu Asp Val Glu Cys
        115                 120                 125

Gly Ser Glu Arg Cys Asn Ile Leu Glu Ala Phe Asp Ala Phe Ile Phe
    130                 135                 140

Ala Phe Phe Ala Val Glu Met Val Ile Lys Met Val Ala Leu Gly Leu
145                 150                 155                 160

Phe Gly Gln Lys Cys Tyr Leu Gly Asp Thr Trp Asn Arg Leu Asp Phe
                165                 170                 175

Phe Ile Val Val Ala Gly Met Met Glu Tyr Ser Leu Asp Gly His Asn
            180                 185                 190

Val Ser Leu Ser Ala Ile Arg Thr Val Arg Val Leu Arg Pro Leu Arg
        195                 200                 205

Ala Ile Asn Arg Val Pro Ser Met Arg Ile Leu Val Thr Leu Leu Leu
    210                 215                 220

Asp Thr Leu Pro Met Leu Gly Asn Val Leu Leu Leu Cys Phe Phe Val
225                 230                 235                 240

Phe Phe Ile Phe Gly Ile Val Gly Val Gln Leu Trp Ala Gly Leu Leu
                245                 250                 255

Arg Asn Arg Cys Phe Leu Asp Ser Ala Phe Val Arg Asn Asn Asn Leu
            260                 265                 270

Thr Phe Leu Arg Pro Tyr Tyr Gln Thr Glu Glu Gly Glu Glu Asn Pro
        275                 280                 285

Phe Ile Cys Ser Ser Arg Arg Asp Asn Gly Met Gln Lys Cys Ser His
    290                 295                 300
```

```
Ile Pro Gly Arg Arg Glu Leu Arg Met Pro Cys Thr Leu Gly Trp Glu
305                 310                 315                 320

Ala Tyr Thr Gln Pro Gln Ala Glu Gly Val Gly Ala Ala Arg Asn Ala
                325                 330                 335

Cys Ile Asn Trp Asn Gln Tyr Tyr Asn Val Cys Arg Ser Gly Asp Ser
            340                 345                 350

Asn Pro His Asn Gly Ala Ile Asn Phe Asp Asn Ile Gly Tyr Ala Trp
        355                 360                 365

Ile Ala Ile Phe Gln Val Ile Thr Leu Glu Gly Trp Val Asp Ile Met
    370                 375                 380

Tyr Tyr Val Met Asp Ala His Ser Phe Tyr Asn Phe Ile Tyr Phe Ile
385                 390                 395                 400

Leu Leu Ile Ile Val Gly Ser Phe Phe Met Ile Asn Leu Cys Leu Val
                405                 410                 415

Val Ile Ala Thr Gln Phe Ser Glu Thr Lys Gln Arg Glu Ser Gln Leu
            420                 425                 430

Met Arg Glu Gln Arg Ala Arg His Leu Ser Asn Asp Ser Thr Leu Ala
        435                 440                 445

Ser Phe Ser Glu Pro Gly Ser Cys Tyr Glu Glu Leu Leu Lys Tyr Val
    450                 455                 460

Gly His Ile Phe Arg Lys Val Lys Arg Arg Ser Leu Arg Leu Tyr Ala
465                 470                 475                 480

Arg Trp Gln Ser Arg Trp Arg Lys Lys Val Asp Pro Ser Ala Val Gln
                485                 490                 495

Gly Gln Gly Pro Gly His Arg Gln Arg Arg Ala Gly Arg His Thr Ala
            500                 505                 510

Ser Val His His Leu Val
        515

<210> SEQ ID NO 34
<211> LENGTH: 1080
<212> TYPE: DNA
<213> ORGANISM: HUMAN

<400> SEQUENCE: 34
gcagtgtcat gtctctaggg aggatgagct atgaccagcg ctccctgtcc agctcccgga      60
gctcctacta cgggccatgg ggccgcagcg cggcctgggc cagccgtcgc tccagctgga     120
acagcctcaa gcacaagccg ccgtcggcgc agcatgagtc cctgctctct gcggagcgcg     180
gcggcggcgc ccgggtctgc gaggttgccg cggacgaggg gccgccgcgg gccgcacccc     240
tgcacacccc acacgcccac acattcatc acgggcccca tctggcgcac cgccaccgcc     300
accaccgccg gacgctgtcc ctcgacaaca gggactcggt ggacctggcc gagctggtgc     360
ccgcggtggg cgcccacccc cgggccgcct ggagggcggc aggcccggcc ccgggcatg     420 aggactgcaa tggcaggatg cccagcatcg ccaaagacgt cttcaccaag atgggcgacc     480
gcggggatcg cggggaggat gaggaggaaa tcgactacac cctgtgcttc gcgtccgca     540 agatgatcga cgtctataag cccgactggt gcgaggtccg cgaagactgg tctgtctacc     600
tcttctctcc cgagaacagg ttccgggtcc tgtgtcagac cattattgcc cacaaactct     660
tcgactacgt cgtcctggcc ttcatctttc tcaactgcat caccatcgcc ctggagcggc     720
ctcagatcga ggccggcagc accgaacgca tctttctcac cgtgtccaac tacatcttca     780
cggccatctt cgtgggcgag atgacattga aggtagtctc gctgggcctg tacttcggcg     840
```

-continued

```
agcaggcgta cctacgcagc agctggaacg tgctggatgg ctttcttgtc ttcgtgtcca      900
tcatcgacat cgtggtgtcc ctggcctcag ccggggggagc caagatcttg ggggtcctcc      960
gagtcttgcg ctcctgcgc accctacgcc cctgcgtgt catcagccgg gcgccgggcc      1020
tgaagctggt ggtggagaca ctcatctcct ccctcaagcc catcggcaac atcgtgctca      1080
```

<210> SEQ ID NO 35
<211> LENGTH: 359
<212> TYPE: PRT
<213> ORGANISM: HUMAN

<400> SEQUENCE: 35

```
Ser Val Met Ser Leu Gly Arg Met Ser Tyr Asp Gln Arg Ser Leu Ser
 1               5                  10                  15

Ser Ser Arg Ser Ser Tyr Tyr Gly Pro Trp Gly Arg Ser Ala Ala Trp
             20                  25                  30

Ala Ser Arg Arg Ser Ser Trp Asn Ser Leu Lys His Lys Pro Pro Ser
         35                  40                  45

Ala Glu His Glu Ser Leu Leu Ser Ala Glu Arg Gly Gly Gly Ala Arg
     50                  55                  60

Val Cys Glu Val Ala Ala Asp Glu Gly Pro Pro Arg Ala Ala Pro Leu
 65                  70                  75                  80

His Thr Pro His Ala His His Ile His His Gly Pro His Leu Ala His
                 85                  90                  95

Arg His Arg His His Arg Arg Thr Leu Ser Leu Asp Asn Arg Asp Ser
            100                 105                 110

Val Asp Leu Ala Glu Leu Val Pro Ala Val Gly Ala His Pro Arg Ala
        115                 120                 125

Ala Trp Arg Ala Ala Gly Pro Ala Pro Gly His Glu Asp Cys Asn Gly
    130                 135                 140

Arg Met Pro Ser Ile Ala Lys Asp Val Phe Thr Lys Met Gly Asp Arg
145                 150                 155                 160

Gly Asp Arg Gly Glu Asp Glu Glu Ile Asp Tyr Thr Leu Cys Phe
                165                 170                 175

Arg Val Arg Lys Met Ile Asp Val Tyr Lys Pro Asp Trp Cys Glu Val
            180                 185                 190

Arg Glu Asp Trp Ser Val Tyr Leu Phe Ser Pro Glu Asn Arg Phe Arg
        195                 200                 205

Val Leu Cys Gln Thr Ile Ile Ala His Lys Leu Phe Asp Tyr Val Val
    210                 215                 220

Leu Ala Phe Ile Phe Leu Asn Cys Ile Thr Ile Ala Leu Glu Arg Pro
225                 230                 235                 240

Gln Ile Glu Ala Gly Ser Thr Glu Arg Ile Phe Leu Thr Val Ser Asn
                245                 250                 255

Tyr Ile Phe Thr Ala Ile Phe Val Gly Glu Met Thr Leu Lys Val Val
            260                 265                 270

Ser Leu Gly Leu Tyr Phe Gly Glu Gln Ala Tyr Leu Arg Ser Ser Trp
        275                 280                 285

Asn Val Leu Asp Gly Phe Leu Val Phe Val Ser Ile Asp Ile Val
    290                 295                 300

Val Ser Leu Ala Ser Ala Gly Gly Ala Lys Ile Leu Gly Val Leu Arg
305                 310                 315                 320

Val Leu Arg Leu Leu Arg Thr Leu Arg Pro Leu Arg Val Ile Ser Arg
                325                 330                 335
```

```
-continued

Ala Pro Gly Leu Lys Leu Val Val Glu Thr Leu Ile Ser Ser Leu Lys
            340                 345                 350

Pro Ile Gly Asn Ile Val Leu
            355
```